US012735719B2

(12) United States Patent
Ni et al.

(10) Patent No.: US 12,735,719 B2
(45) Date of Patent: Sep. 15, 2026

(54) NON-VIRAL TRANSGENESIS

(71) Applicant: THE REGENTS OF THE UNIVERSITY OF CALIFORNIA, Oakland, CA (US)

(72) Inventors: Chih-Wen Ni, Merced, CA (US); Chang-Ying Chiang, Merced, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1156 days.

(21) Appl. No.: 17/597,997

(22) PCT Filed: Jul. 31, 2020

(86) PCT No.: PCT/US2020/070344
§ 371 (c)(1),
(2) Date: Feb. 1, 2022

(87) PCT Pub. No.: WO2021/022308
PCT Pub. Date: Feb. 4, 2021

(65) Prior Publication Data

US 2022/0307050 A1 Sep. 29, 2022

Related U.S. Application Data

(60) Provisional application No. 62/881,822, filed on Aug. 1, 2019.

(51) Int. Cl.

| | |
|---|---|
| ***C12N 15/85*** | (2006.01) |
| ***C12N 15/86*** | (2006.01) |
| ***C12N 15/90*** | (2006.01) |

(52) U.S. Cl.
CPC ......... *C12N 15/8509* (2013.01); *C12N 15/86* (2013.01); *C12N 15/90* (2013.01); *A01K 2217/05* (2013.01); *A01K 2227/40* (2013.01); *C12N 2740/16022* (2013.01); *C12N 2740/16043* (2013.01); *C12N 2830/46* (2013.01)

(58) Field of Classification Search
CPC .... C12N 15/8509; C12N 15/86; C12N 15/90; C12N 2740/16022; C12N 2740/16043; C12N 2830/46; A01K 2217/05; A01K 2227/40
See application file for complete search history.

(56) References Cited

U.S. PATENT DOCUMENTS

| | | | | |
|---|---|---|---|---|
| 2006/0019393 | A1* | 1/2006 | Cannon | C12N 15/86 435/456 |
| 2012/0039932 | A1 | 2/2012 | Allen et al. | |
| 2012/0263754 | A1 | 10/2012 | Dubensky, Jr. et al. | |

FOREIGN PATENT DOCUMENTS

| | | | | |
|---|---|---|---|---|
| EP | 1250453 B1 | | 4/2008 | |
| WO | WO-0142509 A1 | * | 6/2001 | C12N 15/10 |
| WO | WO-2011011584 A1 | * | 1/2011 | A61P 37/04 |

OTHER PUBLICATIONS

Li, M. and Craigie, R., The Journal of Biological Chemistry, vol. 280, No. 32, p. 29334-29339, Aug. 12, 2005 (Year: 2005).*
Andreas, S., et al., Nucleic Acids Research, vol. 30, No. 11, p. 2299-2306, Jun. 1, 2002. (Year: 2002).*
Wu, X., et al., Molecular Therapy, vol. 2, Issue 1, p. 47-55, Jul. 2000 (Year: 2000).*
Art Choudhury, R., et al., Nature Communications, vol. 3, Issue 1147, p. 1-8, Oct. 23, 2012 (Year: 2012).*
Rothweiler, U. et al., Nuclelic Acids Research, vol. 52, p. 1-10, published online Sep. 13, 2024. (Year: 2024).*
Bouabe et al. A protocol for construction of gene targeting vectors and generation of homologous recombinant ES cells. Methods in Molecular Biology. 2013, vol. 1064.
Chiang et al. Efficient Nonviral Stable Transgenesis Mediated by Retroviral Integrase. Molecular Therapy Methods & Clinical Development. Jun. 12, 2020, vol. 17.
ISR and Written Opinion of ISA/US of PCT/US2020/070344 dated Apr. 9, 2021.
Li et al. Processing of Viral DNA Ends Channels the HIV-1 Integration Reaction to Concerted Integration. Journal of Biological Chemistry. Aug. 12, 2005, vol. 280, No. 32.

* cited by examiner

*Primary Examiner* — Neil P Hammell
*Assistant Examiner* — Krishna N Ravindra
(74) *Attorney, Agent, or Firm* — Platinum Intellectual Property, PC

(57) ABSTRACT

Provided herein are new compositions and methods for use in introducing transgenes into cells. The compositions are non-viral but achieve levels of transgene integration comparable to those obtained with viral-mediated methods, and can be used for targeted integration of a transgene at a specific genomic locus.

12 Claims, 21 Drawing Sheets

Specification includes a Sequence Listing.

FIG. 7

5'-TGGAAGGGCTAATTCACTCCCAACGAAGACAAGATAT
CCTTGATCTGTGGATCTACCACACACAAGGCTACTTCCC
TGATTGGCAGAACTACACACCAGGGCCAGGGGTCAGAT
ATCCACTGACCTTTGGATGGTGCTACAAGCTAGTACCA
GTTGAGCCAGATAAGGTAGAAGAGGCCAATAAAGGAGA
GAACACCAGCTTGTTACACCCTGTGAGCCTGCATGGAA
TGGATGACCCTGAGAGAGAAGTGTTAGAGTGGAGGTTT
GACAGCCGCCTAGCATTTCATCACGTGGCCCGAGAGCT
GCATCCGGAGTACTTCAAGAACTGCTGACATCGAGCTT
GCTACAAGGGACTTTCCGCTGGGGACTTTCCAGGGAGG
CGTGGCCTGGGCGGGACTGGGGAGTGGCGAGCCCTCA
GATGCTGCATATAAGCAGCTGCTTTTTGCCTGTACTGGG
TCTCTCTGGTTAGACCAGATTTGAGCCTGGGAGCTCTCT
GGCTAACTAGGGAACCCACTGCTTAAGCCTCAATAAAG
CTTGCCTTGAGTGCTTCAAGTAGTGTGTGCCCGTCTGTT
GTGTGACTCTGGTAACTAGAGATCCCTCAGACCCTTTTA
GTCAGTGTGGAAAATCTCTAGCA-3' (SEQ ID NO. 1)

HIV-1 LTR

<u>TGGAAGGGCTAATTCACTCCCAACGAAGACAAGAT</u>ATC
CTTGATCTGTGGATCTACCACACACAAGGCTACTTCCCT
GATTGGCAGAACTACACACCAGGGCCAGGGGTCAGATA
TCCACTGACCTTTGGATGGTGCTACAAGCTAGTACCAGT
TGAGCCAGATAAGGTAGAAGAGGCCAATAAAGGAGAGA
ACACCAGCTTGTTACACCCTGTGAGCCTGCATGGAATG
GATGACCCTGAGAGAGAAGTGTTAGAGTGGAGGTTTGA
CAGCCGCCTAGCATTTCATCACGTGGCCCGAGAGCTGC
ATCCGGAGTACTTCAAGAACTGCTGACATCGAGCTTGC
TACAAGGGACTTTCCGCTGGGGACTTTCCAGGGAGGCG
TGGCCTGGGCGGGACTGGGGAGTGGCGAGCCCTCAGA
TGCTGCATATAAGCAG<u>CTGCTTTTTGCCTGTACTG</u>
(SEQ ID NO. 2)

HIV-1 U3

B

TGGAAGGGCTAATTCACTCCCAACGAAGACAAGATCTG
CTTTTTGCCTGTACTG (SEQ ID NO. 3)

HIV-1 dU3

TGGAAGGGCTAATTCACTCCCAACGAAGACAAGATATCCTTGATCTG
TGGATCTACCACACACAAGGCTACTTCCCTGATTGGCAGAACTACAC
ACCAGGGCCAGGGGTCAGATATCCACTGACCTTTGGATGGTGCTAC
AAGCTAGTACCAGTTGAGCCAGATAAGGTAGAAGAGGCCAATAAAGG
AGAGAACACCAGCTTGTTACACCCTGTGAGCCTGCATGGAATGGATG
ACCCTGAGAGAGAAGTGTTAGAGTGGAGGTTTGACAGCCGCCTAGC
ATTTCATCACGTGGCCCGAGAGCTGCATCCGGAGTACTTCAAGAACT
GCTGACATCGAGCTTGCTACAAGGGACTTTCCGCTGGGGACTTTCCA
GGGAGGCGTGGCCTGGGCGGGACTGGGGAGTGGCGAGCCCTCAGA
TGCTGCATATAAGCAGCTGCTTTTTGCCTGTACTGGGTCTCTCTGGTT
AGACCAGATTTGAGCCTGGGAGCTCTCTGGCTAACTAGGGAACCCA
CTGCTTAAGCCTCAATAAAGCTTGCCTTGAGTGCTTCAAGTAGTGTGT
GCCCGTCTGTTGTGTGACTCTGGTAACTAGAGATCCCTCAGACCCTT
TTAGTCAGTGTGGAAAATCTCTAGCA (SEQ ID NO. 1)

HIV-1 LTR

B

GGTCTCTCTGGTTAGACCAGATTTGAGCCTGGGAGCTCTCTGGCTAA
CTAGGGAACCCACTGCTTAAGCCTCAATAAAGCTTGCCTTGAGTGCT
TCAAGTAGTGTGTGCCCGTCTGTTGTGTGACTCTGGTAACTAGAGAT
CCCTCAGACCCTTTTAGTCAGTGTGGAAAATCTCTAGCA
(SEQ ID NO. 4)

5' dLTR

TGGAAGGGCTAATTCACTCCCAACGAAGACAAGATATCCTTGATCTG
TGGATCTACCACACACAAGGCTACTTCCCTGATTGGCAGAACTACAC
ACCAGGGCCAGGGGTCAGATATCCACTGACCTTTGGATGGTGCTAC
AAGCTAGTACCAGTTGAGCCAGATAAGGTAGAAGAGGCCAATAAAGG
AGAGAACACCAGCTTGTTACACCCTGTGAGCCTGCATGGAATGGATG
ACCCTGAGAGAGAAGTGTTAGAGTGGAGGTTTGACAGCCGCCTAGC
ATTTCATCACGTGGCCCGAGAGCTGCATCCGGAGTACTTCAAGAACT
GCTGACATCGAGCTTGCTACAAGGGACTTTCCGCTGGGGACTTTCCA
GGGAGGCGTGGCCTGGGCGGGACTGGGGAGTGGCGAGCCCTCAGA
TGCTGCATATAAGCAGCTGCTTTTTGCCTGTACTGGGTCTCTCTGGTT
AGACCAGATTTGAGCCTGGGAGCTCTCTGGCTAACTAGGGAACCCA
CTGCTTAAGCCTCAATAAAGCTTGCCTTGAGTGCTTCAAGTAGTGTGT
GCCCGTCTGTTGTGTGACTCTGGTAACTAGAGATCCCTCAGACCCTT
TTAGTCAGTGTGGAAAATCTCTAGCA (SEQ ID NO. 1)

HIV-1 LTR

B

TGGAAGGGCTAATTCACTCCCAACGAAGACAAGATCTGCTTTTTGCC
TGTACTGGGTCTCTCTGGTTAGACCAGATTTGAGCCTGGGAGCTCTC
TGGCTAACTAGGGAACCCACTGCTTAAGCCTCAATAAAGCTTGCCTT
GAGTGCTTCAAGTAGTGTGTGCCCGTCTGTTGTGTGACTCTGGTAAC
TAGAGATCCCTCAGACCCTTTTAGTCAGTGTGGAAAATCTCTAGCA
(SEQ ID NO. 5)

3' dLTR

NON-VIRAL TRANSGENESIS

RELATED APPLICATIONS

This application is a United States National Stage Application filed under 35 U.S.C 371 of PCT Patent Application Serial No. PCT/US2020/070344, filed Jul. 31, 2020, which claims Provisional Patent Application No. 62/881,822, filed Aug. 1, 2019, the disclosure of all of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jul. 29, 2020, is named M2-PCT_SL.txt and is 54,500 bytes in size.

TECHNICAL FIELD

The present disclosure is in the field of transgenesis. New compositions for use in inserting a transgene into a cell; and methods utilizing said new compositions, are provided herein.

BACKGROUND OF THE INVENTION

Methods for insertion of exogenous genes (transgenes) into cells are increasingly important in the fields of genetic research and gene therapy. Although a number of methods for introducing transgenes into cells exist; all are beset with problems of one sort or another. Transfection methods (i.e., simply contacting cells with naked DNA or a DNA conjugate) have a low efficiency and often result in the exogenous sequences undergoing rearrangement in the recipient cell.

Viral vectors; including adenovirus, adeno-associated virus (AAV), retrovirus, foamy virus, herpesvirus, and poxvirus vectors; have also been used for inserting transgenes into cells. Viral transgenesis is more efficient than simple transfection, and can provide stable transgenesis if the virally-introduced transgene is integrated into the recipient cell genome, or maintained in the recipient cell as an episome. However, viral vectors require modification of the viral genome so that replication is blocked or inefficient; which, in turn, requires that the debilitated vector virus be propagated in the presence of a helper virus (which supplies, in trans, the functions missing in the vector virus), requiring complicated culture systems.

An additional drawback associated with the use of viral vectors is the limitations on the size of the transgene that can be inserted into a viral vector; since even vector viruses must retain a certain amount of viral sequences to work effectively as a delivery vehicle; and most viruses are unable to package DNA molecules any larger that about 110% of viral genome size.

Another problem with the use of viral vectors in gene therapy is the ability of the capsid proteins of the vector virus to induce an immune response, which can destroy or damage the vector before the transgene is stably introduced into the recipient cell.

One class of viral vectors is retroviruses. Retroviruses (which include the genus of lentiviruses) have a single-stranded RNA genome. A repeated sequence (R) is present at the extreme 5' and 3' ends of the retroviral genome. Immediately interior to the R sequence, at the 5' end of viral RNA, is a sequence known as U5. Immediately interior to the R sequence, at the 3' end of viral RNA, is a sequence known as U3. A schematic diagram of a generic retroviral RNA genome, showing the location of the R, U5 and U3 sequences, is shown in FIG. 1.

During the retroviral infectious cycle, the RNA genome is copied into a single-stranded DNA molecule (by a process of reverse transcription, catalyzed by the reverse transcriptase enzyme, product of the viral pol gene). The single-stranded DNA product of reverse transcription is then copied (again by reverse transcriptase) to form a double-stranded viral DNA molecule. Due to the nature of the copying processes (e.g., requirements for primers), the U3 sequence becomes appended to the 5' end of the double-stranded viral DNA genome (exterior to the R sequence); and the U5 sequence is appended to the 3' end of the double-stranded viral DNA genome (exterior to the R sequence), forming identical long terminal repeat (LTR) sequences at the termini of the double-stranded DNA genome. A schematic diagram of a generic retroviral double-stranded DNA genome, showing the location of the LTRs, and their constituent R, U5 and U3 sequences, is shown in FIG. 2.

Following conversion of the single-stranded RNA genome to a double-stranded DNA genome; the double-stranded DNA genome, flanked by its LTRs, is inserted into the host cell genome. This insertion reaction is catalyzed by the viral integrase protein (also a product of the pol gene), and requires a double-stranded, blunt-ended DNA molecule, with the inverted terminal repeat sequence 5'-ACTG-3' (for HIV-1) as a substrate. The integrase protein removes the terminal TG residues on each strand, generating a double-stranded DNA molecule with a two-nucleotide 5' overhang (5'-AC-3') at each end. This molecule serves as a substrate for strand transfer by the int protein and is integrated into the host cell genome.

Retrovirus genomes are generally 8 kb or more in length and because, in most cases, all viral structural genes can be removed and replaced with exogenous sequences, retroviral vectors have a high capacity; requiring only that the transgene be flanked by viral LTRs to facilitate integration. However, the efficiency of stable transgenesis using retroviruses is comparatively low, and most retroviruses (excepting lentiviruses) are unable to infect dividing cells. Furthermore, when retrovirus vectors are used in gene therapy applications, retroviral capsid proteins can trigger immune responses.

For the reasons discussed above, there remains a need for transgenesis systems which have the benefits of viral vectors, such as high efficiency of genomic integration; but that do not suffer from the drawbacks associated with viral vectors, such as limited capacity and immunogenicity.

SUMMARY OF THE INVENTION

Disclosed herein are nucleic acid compositions, and methods for their manufacture and use, that promote highly efficient insertion of transgenes, at levels commonly achieved with viral vectors, but without the use of virus particles. The compositions include transgene cassettes, which have a linear double-stranded DNA structure that resembles a retroviral pre-integration substrate, characterized by blunt ends, a terminal 5'-ACTG-3' sequence and truncated retroviral long terminal repeat (LTR) sequences. Nucleic acid vectors (insertion vectors) comprising transgene cassettes are also provided.

Transgene cassettes can be released from an insertion vector (e.g., a double-stranded circular plasmid DNA molecule) by cleavage with a restriction enzyme that generates blunt ends. Insertion vectors comprise one or more pairs of att sites, optionally with a negative selection marker disposed therebetween, for convenient insertion of transgenes using gateway cloning methods. Exterior to the att sites, insertion cassettes contain truncated retroviral long terminal repeat (LTR) sequences, a 5'-ACTG-3' sequence and recognition sites for a blunt end-generating restriction enzyme.

Integration of a transgene into the genome of a cell is accomplished by contacting the cell with a transgene cassette and a source of retroviral integrase (e.g., DNA or mRNA encoding a retroviral integrase (int) enzyme. The integrase protein recognizes the transgene cassette as a substrate for integration, and integrates the transgene cassette into the genome of the recipient cell.

Accordingly, in certain embodiments, provided herein is a polynucleotide (i.e., a transgene cassette) comprising: (a) one or more selection markers, wherein the selection markers are flanked by (b) first and second att sites, wherein the att sites are flanked by (c) first and second truncated retroviral long terminal repeats (LTRs), wherein the first truncated LTR is upstream of the first att site, the second truncated LTR is downstream of the second att site, and wherein the first and second truncated retroviral LTRs are flanked by recognition sites for a restriction enzyme, wherein cleavage of the recognition sites generates blunt ends, and wherein the sequence 5'-ACTG-3' is present at or near the termini of the polynucleotide.

In certain embodiments, the polynucleotide described in the preceding paragraph is a double-stranded DNA molecule. In additional embodiments, the polynucleotide is single-stranded DNA or RNA.

Selection markers can be positive selection markers (i.e., the presence of the marker promotes cell viability in the presence of a selective agent) or negative selection markers (e.g., a marker that is inhibitory to cell viability so that cells survive when the marker is removed or replaced by exogenous sequences). Exemplary positive selection markers include those encoding resistance to antibiotics such as, for example, penicillin, ampicillin, tetracycline and chloramphenicol. Exemplary negative selection markers include the DNA gyrase inhibitor ccdB.

In certain embodiments, the att sites present in the transgene cassette are attR sites. In further embodiments, the first att site is attR4 and the second att site is attR3. In additional embodiments, the att sites are attL sites, attP sites or attB sites. Mutants and variants of att sites such as, for example, attP3, attP4, attR1, attR2 attR3 attR4, attL1, attL2 attL3 and attL4 are known in the art.

Truncated retroviral LTR sequences can be obtained from the genome of any retrovirus, as known in the art. In certain embodiments, the retrovirus is a lentivirus and the transgene cassette contains truncated lentiviral LTRs. In additional embodiments, the lentivirus is HIV, and the transgene cassette contains truncated HIV LTRs. In further embodiments, the lentivirus is HIV-1, and the transgene cassette contains truncated HIV-1 LTRs.

In certain embodiments, a truncated retroviral LTR is one in which one or more transcriptional regulatory sequences, normally present in the U3 region, are removed. Accordingly, certain truncated LTRs contain deleted U3 (dU3) R and U5 sequences. In additional embodiments of a truncated retroviral LTR, all U3 sequences are removed. Accordingly, certain truncated LTRS contain R and U5 sequences, but no U3 sequences. In certain embodiments, the first truncated LTR comprises R and U5 sequence elements and the second truncated LTR comprises dU3, R and U5 sequence elements.

In additional embodiments, the first truncated LTR comprises the nucleotide sequence:

```
                                            (SEQ. ID NO. 4)
GGTCTCTCTGGTTAGACCAGATCTGAGCCTGGGAGCTCTCTGGCTAACTA

GGGAACCCACTGCTTAAGCCTCAATAAAGCTTGCCTTGAGTGCTTCAAGT

AGTGTGTGCCCGTCTGTTGTGTGACTCTGGTAACTAGAGATCCCTCAGAC

CCTTTTAGTCAGTGTGGAAAATCTCTAGCA
```

In additional embodiments, the second truncated LTR sequence comprises the nucleotide sequence:

```
                                            (SEQ. ID NO. 5)
TGGAAGGGCTAATTCACTCCCAACGAAGACAAGATCTGCTTTTTGCTTGT

ACTGGGTCTCTCTGGTTAGACCAGATCTGAGCCTGGGAGCTCTCTGGCTA

ACTAGGGAACCCACTGCTTAAGCCTCAATAAAGCTTGCCTTGAGTGCTTC

AAGTAGTGTGTGCCCGTCTGTTGTGTGACTCTGGTAACTAGAGATCCCTC

AGACCCTTTTAGTCAGTGTGGAAAATCTCTAGCA
```

In further embodiments, the first truncated LTR comprises the nucleotide sequence:

```
                                            (SEQ. ID NO. 4)
GGTCTCTCTGGTTAGACCAGATCTGAGCCTGGGAGCTCTCTGGCTAACTA

GGGAACCCACTGCTTAAGCCTCAATAAAGCTTGCCTTGAGTGCTTCAAGT

AGTGTGTGCCCGTCTGTTGTGTGACTCTGGTAACTAGAGATCCCTCAGAC

CCTTTTAGTCAGTGTGGAAAATCTCTAGCA
```

and the second truncated LTR sequence comprises the nucleotide sequence:

```
                                            (SEQ. ID NO. 5)
TGGAAGGGCTAATTCACTCCCAACGAAGACAAGATCTGCTTTTTGCTTGT

ACTGGGTCTCTCTGGTTAGACCAGATCTGAGCCTGGGAGCTCTCTGGCTA

ACTAGGGAACCCACTGCTTAAGCCTCAATAAAGCTTGCCTTGAGTGCTTC

AAGTAGTGTGTGCCCGTCTGTTGTGTGACTCTGGTAACTAGAGATCCCTC

AGACCCTTTTAGTCAGTGTGGAAAATCTCTAGCA
```

The termini of the transgene cassette comprise recognition sites for a restriction enzyme whose cleavages results in production of blunt ends. In certain embodiments, the recognition sites comprise six or more nucleotide pairs (i.e., six, seven, eight, nine, ten, twelve or more nucleotide pairs). The longer the recognition site, the less likely it is that the restriction enzyme that recognizes that site will also recognize a site in the transgene insert (thereby destroying the integrity of the transgene). Generally both recognition sites will be recognized by the same restriction enzyme, but it is also possible to have recognition sites for different restriction enzymes at each end of the cassette, as long as both enzymes generate blunt ends after cleavage. In certain embodiments, the recognition sites are the same at both ends of the cassette and are recognized by a restriction enzyme selected from the group consisting of PmeI, ScaI and Bst Z17I.

Transgene cassettes also contain the sequence 5'-ACTG-3' at or near the termini of the polynucleotide. In certain embodiments, the sequence 5'-ACTG-3' is present exactly at the termini of the transgene cassette, such that the transgene cassette terminates in blunt ends having the sequence

```
5'-ACTG-3'

3'-TGAC-3'.
```

In other embodiments, one additional nucleotide pair is present, outside the sequence 5'-ACTG-3', at the termini of the transgene cassette. In additional embodiments, two additional nucleotide pairs are present, outside the sequence 5'-ACTG-3', at the termini of the transgene cassette. In further embodiments, three, four or five additional nucleotide pairs are present, outside the sequence 5'-ACTG-3', at the termini of the transgene cassette.

In certain embodiments, provided herein is a transgene cassette comprising (a) sequences encoding chloramphenicol resistance and the ccdB locus, wherein the sequences encoding chloramphenicol resistance and the ccdB locus are flanked by (b) an upstream attR4 site and a downstream attR3 site, wherein the att sites are flanked by (c) a 5' dLTR sequence comprising R and U5 sequence elements upstream of the attR4 site and a 3' dLTR sequence comprising dU3, R and U5 sequence elements downstream of the attR3 site, wherein the 5' and 3' dLTR sequences are flanked by (e) recognition sites for a restriction enzyme selected from the group consisting of PmeI, ScaI and BstZ17I and wherein all or part of the sequence 5'-ACTG-3' is present within or near the recognition site for the restriction enzyme.

In certain embodiments of the transgene cassette described in the preceding paragraph, the 5' dLTR sequence comprises SEQ ID NO:4, and the 3' dLTR sequence comprises SEQ ID NO:5.

In additional embodiments, polynucleotides whose nucleotide sequences are homologous to that of the transgene cassette are provided. The nucleotide sequences of the homologous polynucleotides are at least 50% homologous, at least 60% homologous, at least 70% homologous, at least 75% homologous, at least 80% homologous, at least 85% homologous, at least 90% homologous, at least 95% homologous, at least 96% homologous, at least 97% homologous, at least 98% homologous, or at least 99% homologous to the sequence of the transgene cassettes described herein. Such homologous polynucleotides can be DNA or RNA and can be single-stranded or double-stranded.

In additional embodiments, polynucleotides having nucleotide sequences complementary to the sequence of either strand of the transgene cassette are provided. Such polynucleotides can be DNA or RNA. In further embodiments, this disclosure provides polynucleotides that hybridize under stringent conditions to a transgene cassette as disclosed herein.

Also provided are nucleic acid vectors (e.g., plasmid vectors) comprising a transgene cassette as disclosed herein; i.e., transgene vectors. Accordingly, in certain embodiments, provided herein is a plasmid comprising: (a) one or more selection markers, wherein the selection markers are flanked by (b) first and second att sites, wherein the att sites are flanked by (c) first and second truncated retroviral long terminal repeats (LTRs), wherein the first truncated LTR is upstream of the first att site, the second truncated LTR is downstream of the second att site, and wherein the first and second truncated retroviral LTRs are flanked by recognition sites for a restriction enzyme, wherein cleavage of the recognition sites generates blunt ends and wherein all or part of the sequence 5'-ACTG-3' is present within or near the recognition site for the restriction enzyme.

In additional embodiments, provided herein is a plasmid comprising (a) sequences encoding chloramphenicol resistance and the ccdB locus, wherein the sequences encoding chloramphenicol resistance and the ccdB locus are flanked by (b) an upstream attR4 site and a downstream attR3 site, wherein the att sites are flanked by (c) a 5' dLTR sequence comprising R and U5 sequence elements upstream of the attR4 site and a 3' dLTR sequence comprising dU3, R and U5 sequence elements downstream of the attR3 site, wherein the 5' and 3' dLTR sequences are flanked by (d) first and second 5'-ACTG-3' sequences, wherein all or part of the first and second 5'-ACTG-3' sequences are within or near (e) recognition sites for a restriction enzyme selected from the group consisting of PmeI, ScaI and BstZ17I.

Also provided are plasmid vectors comprising a transgene cassette and a transgene. In certain embodiments, the transgene is located between the att sites of the transgene cassette, having been inserted by gateway cloning methodology, and optionally replacing one or more selection markers that were present between the att sites prior to insertion of the transgene. In certain embodiments, att sites present in the transgene vector (e.g., attR4 and attR3) are converted into different att sites (e.g., attP4 and attP3) in the process of transgene insertion. Transgenes are introduced by one-way, two-way or three-way gateway cloning, as known in the art. See, for example, Hartley et al. (2000) Genome Research 10:1788-1795.

Any sequence, coding or noncoding, can serve as a transgene. For example, a transgene can encode a detectable moiety; e.g., a fluorescent protein, such as green fluorescent protein (GFP), enhanced green fluorescent protein (EGFP), red fluorescent protein, yellow fluorescent protein, tdTomato and the like. A transgene can also encode an enzymatic activity (e.g., β-galactosidase, β-glucuronidase, luciferase, or an oxidorecuctase). A transgene can also be a therapeutic protein, such as globin or a coagulation factor.

Accordingly, in certain embodiments, provided herein is a polynucleotide comprising: (a) a transgene, wherein the transgene is flanked by (b) first and second att sites, wherein the att sites are flanked by (c) first and second truncated retroviral long terminal repeats (LTRs), wherein the first truncated LTR is upstream of the first att site, the second truncated LTR is downstream of the second att site, and wherein the first and second truncated retroviral LTRs are flanked by recognition sites for a restriction enzyme, wherein cleavage of the recognition sites generates blunt ends; the polynucleotide further comprising the sequence 5'-ACTG-3' at or near its termini (i.e., at the termini of the polynucleotide, or within one, two, three four or five nucleotide pairs of the termini of the polynucleotide); and optionally wherein a selection marker is not present between the two att sites. In certain embodiments, the 5' dLTR sequence comprises SEQ ID NO:4, and the 3' dLTR sequence comprises SEQ ID NO:5. In further embodiments, this polynucleotide is present in a plasmid. In additional embodiments, this polynucleotide is a linear, double-stranded DNA molecule.

In additional embodiments, provided herein is a polynucleotide comprising (a) a transgene, wherein the transgene is flanked by (b) an upstream attP4 site and a downstream attP3 site, wherein the att sites are flanked by (c) a 5' dLTR sequence comprising R and U5 sequence elements upstream of the attP4 site and a 3' dLTR sequence comprising dU3, R and U5 sequence elements downstream of the attP3 site, wherein the 5' and 3' dLTR sequences are flanked by recognition sites for a restriction enzyme selected from the group consisting of PmeI, ScaI and BstZ17I, wherein the sequence 5'-ACTG-3' is present within or near the recognition site for the restriction enzyme, and optionally wherein a selection marker is not present between the attP4 and attP3 sites. In certain embodiments, the 5' dLTR sequence comprises SEQ ID NO:4, and the 3' dLTR sequence comprises SEQ ID NO:5. In further embodiments, this polynucleotide is present in a plasmid. In additional embodiments, this polynucleotide is a linear, double-stranded DNA molecule.

In certain embodiments, the compositions disclosed herein comprise a plurality of DNA molecules resulting from cleavage of a plasmid with a restriction enzyme that generates blunt ends, wherein the plasmid comprises a transgene-containing transgene cassette. In additional embodiments, the restriction enzyme is selected from the group consisting of PmeI, ScaI and BstZ17I.

Accordingly, in certain embodiments, provided herein is a plurality of DNA molecules, one of which comprises: (a) transgene, wherein the transgene is flanked by (b) first and second att sites, wherein the att sites are flanked by (c) first and second truncated retroviral long terminal repeats (LTRs), wherein the first truncated LTR is upstream of the first att site, the second truncated LTR is downstream of the second att site, and wherein the first and second truncated retroviral LTRs are flanked by (d) partial restriction enzyme recognition sites generated by cleavage with a restriction enzyme that generates blunt ends; and further comprising all or part of the sequence 5'-ACTG-3' at or near its termini (i.e., at its terminus, or within one, two, three four or five nucleotide pairs of its terminus). In further embodiments, the restriction enzyme is selected from the group consisting of PmeI, ScaI and BstZ17I. In certain embodiments, the 5' dLTR sequence comprises SEQ ID NO:4, and the 3' dLTR sequence comprises SEQ ID NO:5.

In additional embodiments, this disclosure provides a plurality of DNA molecules, one of which comprises (a) a transgene, wherein the transgene is flanked by (b) an upstream attP4 site and a downstream attP3 site, wherein the att sites are flanked by (c) a 5' dLTR sequence comprising R and U5 sequence elements upstream of the attR4 site and a 3' dLTR sequence comprising dU3, R and U5 sequence elements downstream of the attR3 site, wherein the 5' and 3' dLTR sequences are flanked by (d) partial restriction enzyme recognition sites generated by cleavage with a restriction enzyme that generates blunt ends; and further comprising all or part of the sequence 5'-ACTG-3' at or near its termini (i.e., at its terminus, or within one, two, three four or five nucleotide pairs of its terminus). In further embodiments, the restriction enzyme is selected from the group consisting of PmeI, ScaI and BstZ17I. In certain embodiments, the 5' dLTR sequence comprises SEQ ID NO:4, and the 3' dLTR sequence comprises SEQ ID NO:5.

Also provided are nucleic acids (double-stranded DNA, single-stranded DNA and/or RNA) encoding a retroviral integrase protein. If the integrase-encoding nucleic acid is DNA, it can be present in a DNA vector, (e.g., a plasmid) in either double-stranded or single-stranded form. The integrase can further comprise one or more additional nuclear localization signals (NLS) in addition to the endogenous integrase NLS.

Also provided are combinations of a nucleic acid (DNA or RNA) encoding a retroviral (e.g., lentiviral; e.g., HIV; e.g., HIV-1) integrase and a transgene-containing transgene cassette (as described above). Further provided are combinations of a nucleic acid (DNA or RNA) encoding a retroviral (e.g., HIV; e.g., HIV-1) integrase and a plurality of DNA molecules (e.g., linear double stranded DNA molecules) comprising a transgene-containing transgene cassette as described above. For use in methods for targeted integration of a transgene, any of the combinations described previously in this paragraph can further comprise a polynucleotide encoding a fusion between dCas9 and psip1a (or a polypeptide comprising a fusion between dCas9 and psip1a); and a guide RNA comprising (i) a hairpin sequence that binds to Cas9 or dCas9, and (ii) a sequence complementary to a genomic target sequence.

Additionally provided herein are methods for introducing a transgene into the genome of a cell, wherein the methods comprise contacting the cell with a combination of a transgene-containing transgene cassette and a nucleic acid encoding a retroviral integrase protein. Contacting can be by, for example, transfection, electroporation, injection or any other method of introducing nucleic acids into a cell. Transgene-containing transgene cassettes have been described above and can be one of a plurality of the products of digestion of a plasmid with a blunt end-generating restriction enzyme. Alternatively, a transgene-containing transgene cassette can be an isolated DNA (or RNA) molecule.

The integrase-encoding nucleic acid can be DNA or mRNA. The retroviral integrase protein can be from any retrovirus. In certain embodiments, the retrovirus is a lentivirus. In additional embodiments, the lentivirus is HIV. In further embodiments, the HIV is HIV-1.

In certain embodiments, provided herein is a plasmid comprising (a) a first recognition site for a restriction enzyme selected from the group consisting of PmeI, ScaI and BstZ17I; (b) the sequence 5'-ACTG-3'; (c) a first truncated long terminal repeat (LTR) sequence comprising SEQ ID NO:4 that is interior to the first recognition site and the 5'-ACTG-3' sequence; (d) an attR4 site that is interior to the first truncated LTR sequence; (e) the ccdB locus; (f) an attR3 site that is exterior to the ccdB locus; (g) a second truncated long terminal repeat (LTR) sequence comprising SEQ ID NO:5 that is exterior to the attR3 site; (h) the sequence 5'-CAGT-3'; and (i) a second recognition site for a restriction enzyme selected from the group consisting of PmeI, ScaI and BstZ17I, wherein the second recognition site is the same as the first recognition site; and wherein the 5'-CAGT-3' sequence and the second recognition site are exterior to the second truncated LTR sequence. In certain embodiments, the 5'-ACTG-3' sequence overlaps with the first recognition site and the 5'-CAGT-3' sequence overlaps with the second recognition site.

In additional embodiments, provided herein is a plasmid comprising, in sequence (a) a first recognition site for a restriction enzyme selected from the group consisting of PmeI, ScaI and BstZ17I; (b) the sequence 5'-ACTG-3'; (c) a first truncated long terminal repeat (LTR) sequence comprising SEQ ID NO:4 that is interior to the first recognition site and the 5'-ACTG-3' sequence; (d) an attP4 site that is interior to the first truncated LTR sequence; (e) a transgene; (f) an attP3 site that is exterior to the transgene; (g) a second truncated long terminal repeat (LTR) sequence comprising SEQ ID NO:5 that is exterior to the attP3 site; (h) the sequence 5'-CAGT-3'; and (i) a second recognition site for a restriction enzyme selected from the group consisting of PmeI, ScaI and BstZ17I, wherein the second recognition site is the same as the first recognition site and wherein the 5'-CAGT-3' sequence and the second recognition site are exterior to the second truncated LTR sequence. In certain embodiments, the 5'-ACTG-3' sequence overlaps with the first recognition site and the 5'-CAGT-3' sequence overlaps with the second recognition site.

In additional embodiments, methods and compositions for targeted integration of transgenes are provided. The methods utilize a fusion protein in which psip1a (LEDGF/p75) amino acid sequences are joined to amino acid sequences of dCas9, optionally through a flexible linker such as $(GGS)_5$. Nucleic acids (i.e., polynucleotides) encoding these fusion proteins are also provided. Also utilized in methods for targeted integration is a guide RNA comprising a portion that is complementary to a target genomic sequence and a portion comprising a RNA hairpin that binds to dCas9. The guide RNA tethers the fusion protein to the target genomic sequence (via its interaction with dCas9) and the psip1A portion of the fusion protein binds to a preintegration complex comprising integrase protein and a transgene cassette.

Accordingly, also provided are combinations of a nucleic acid (DNA or RNA) encoding a retroviral (e.g., lentiviral; e.g., HIV; e.g., HIV-1) integrase, a transgene-containing transgene cassette (as described above), a nucleic acid encoding a fusion between dCas9 and psip1a; and a guide RNA comprising (i) a hairpin sequence that binds to Cas9 or dCas9, and (ii) a sequence complementary to a genomic target sequence.

Additional embodiments provide combinations of a nucleic acid (DNA or RNA) encoding a retroviral (e.g., HIV; e.g., HIV-1) integrase, a plurality of DNA molecules (e.g., linear double stranded DNA molecules) comprising a transgene-containing transgene cassette (as described above), a nucleic acid encoding a fusion between dCas9 and psip1a; and a guide RNA comprising (i) a hairpin sequence that binds to Cas9 or dCas9, and (ii) a sequence complementary to a genomic target sequence.

The disclosure also provides methods for targeted insertion of a transgene into the genome of a cell, the method comprising contacting the cell with a combination comprising a nucleic acid (DNA or RNA) encoding a retroviral (e.g., lentiviral; e.g., HIV; e.g., HIV-1) integrase, a transgene-containing transgene cassette (as described above), a nucleic acid encoding a fusion between dCas9 and psip1a; and a guide RNA comprising (i) a hairpin sequence that binds to Cas9 or dCas9, and (ii) a sequence complementary to a genomic target sequence.

In additional embodiments, the disclosure provides methods for targeted insertion of a transgene into the genome of a cell, the method comprising contacting the cell with a combination comprising a nucleic acid (DNA or RNA) encoding a retroviral (e.g., HIV; e.g., HIV-1) integrase, a plurality of DNA molecules (e.g., linear double stranded DNA molecules) comprising a transgene-containing transgene cassette (as described above), a nucleic acid encoding a fusion between dCas9 and psip1a; and a guide RNA comprising (i) a hairpin sequence that binds to Cas9 or dCas9, and (ii) a sequence complementary to a genomic target sequence.

BRIEF DESCRIPTION OF THE DRAWINGS

FIG. 7 shows the nucleotide sequence of the HIV-1 long terminal repeat (SEQ ID NO:1). The sequence of the R region is underlined. Sequences upstream of the R region constitute the U3 region. Sequences downstream of the R region constitute the U5 region.

FIG. 8A shows the nucleotide sequence of the HIV-1 U3 region (SEQ ID NO:2). Underlining indicates the portions of the U3 region that are retained in the deleted U3 (dU3) sequence. FIG. 8B shows the nucleotide sequence of dU3 (SEQ ID NO:3).

FIG. 9A shows the nucleotide sequence of the HIV-1 LTR (SEQ ID NO:1). The R region is underlined, and the sequences present in 5' dLTR are shaded. FIG. 9B shows the nucleotide sequence of 5' dLTR (SEQ ID NO:4).

FIG. 10A shows the nucleotide sequence of the HIV-1 LTR (SEQ ID NO:1). The R region is underlined, and the sequences present in 3' dLTR are shaded. FIG. 10B shows the nucleotide sequence of 3' dLTR (SEQ ID NO:5).

"AmpR" refers to sequences encoding resistance to ampicillin; "ColE1 origin" refers to the replication origin for Col E1 plasmid; "5' . . . 83" refers to the 5' dLTR sequence; "3' L . . . 319" refers to the 3' dLTR sequence. Recognition sites for the BstZ17I restriction enzyme are also shown.

Figure 11:
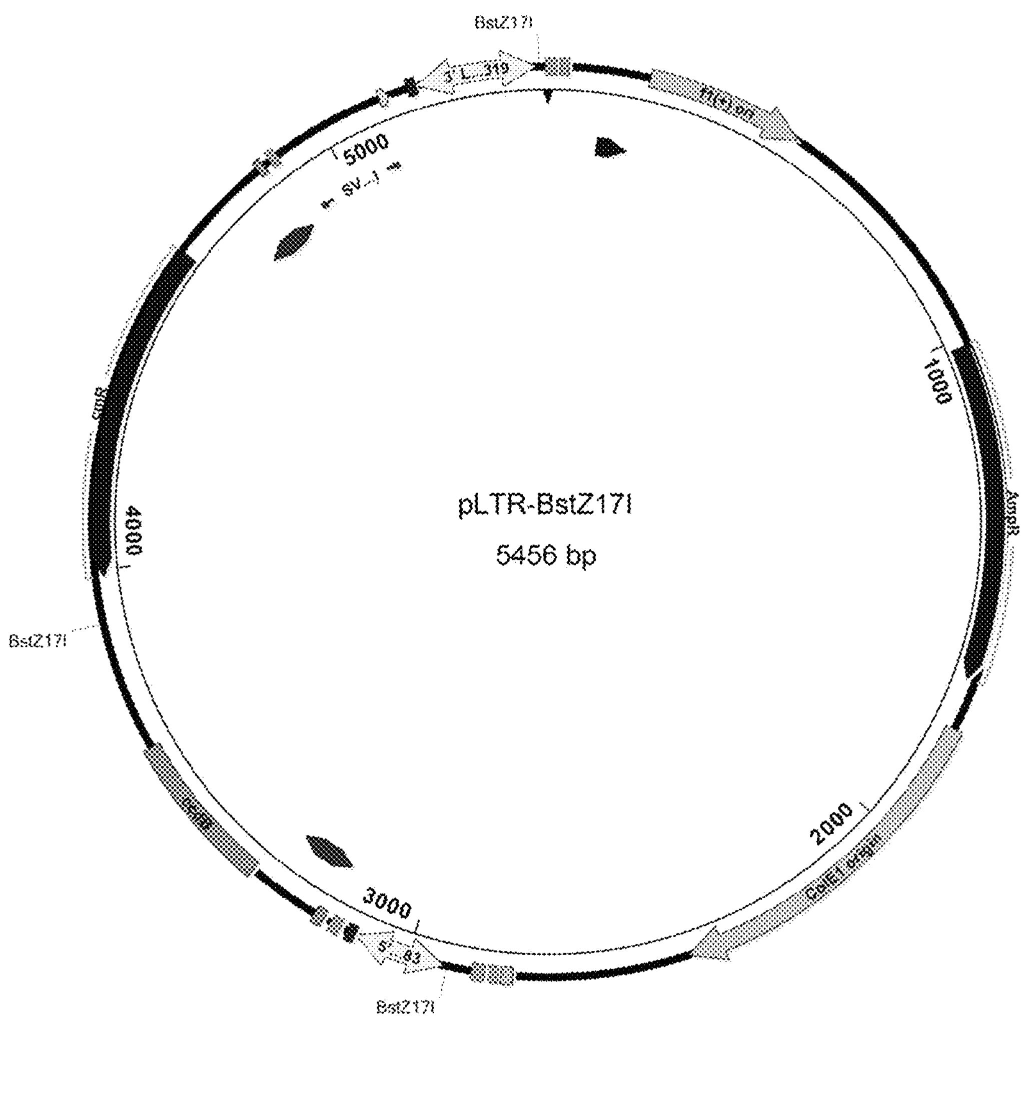
FIG. 11 is a schematic diagram of a transgene (pLTR) vector, showing the locations of 5' dLTR and 3' dLTR sequences and other features of the vector. Abbreviations: "cmR" refers to sequences encoding resistance to chloramphenicol; "ccdB" refers to sequences encoding a DNA gyrase inhibitor lethal to *E. coli*; "f1(+) ori" refers to the replication origin for the + strand of f1 bacteriophage.
Figure 12:
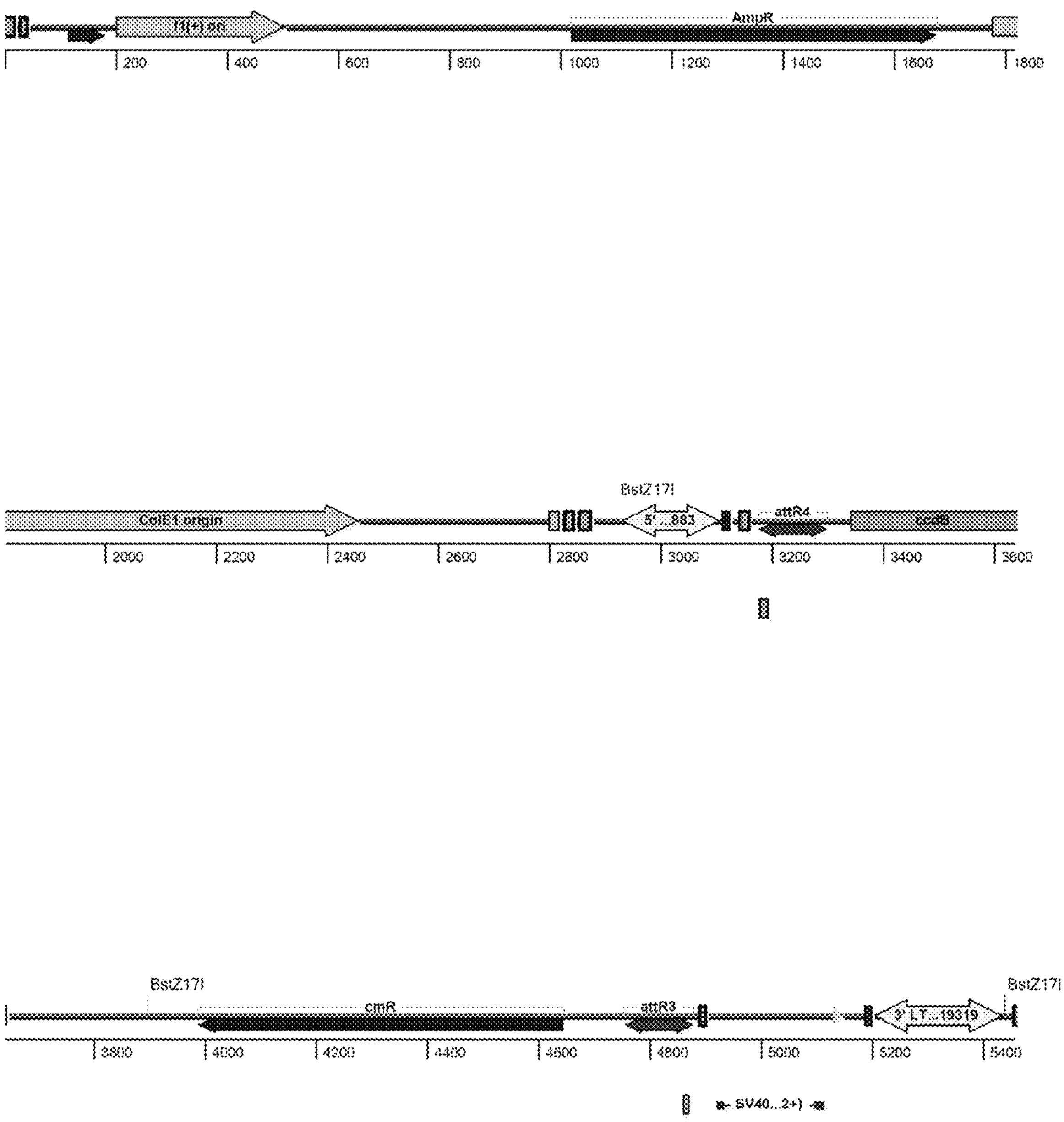

FIG. 12 is a schematic diagram showing portions of the pLTR vector (shown in FIG. 11) in greater detail. "attR3" and "attR4" refer to sites at which recombination will occur with other att sites in the presence of bacteriophage λ recombination proteins.

Figure 13:
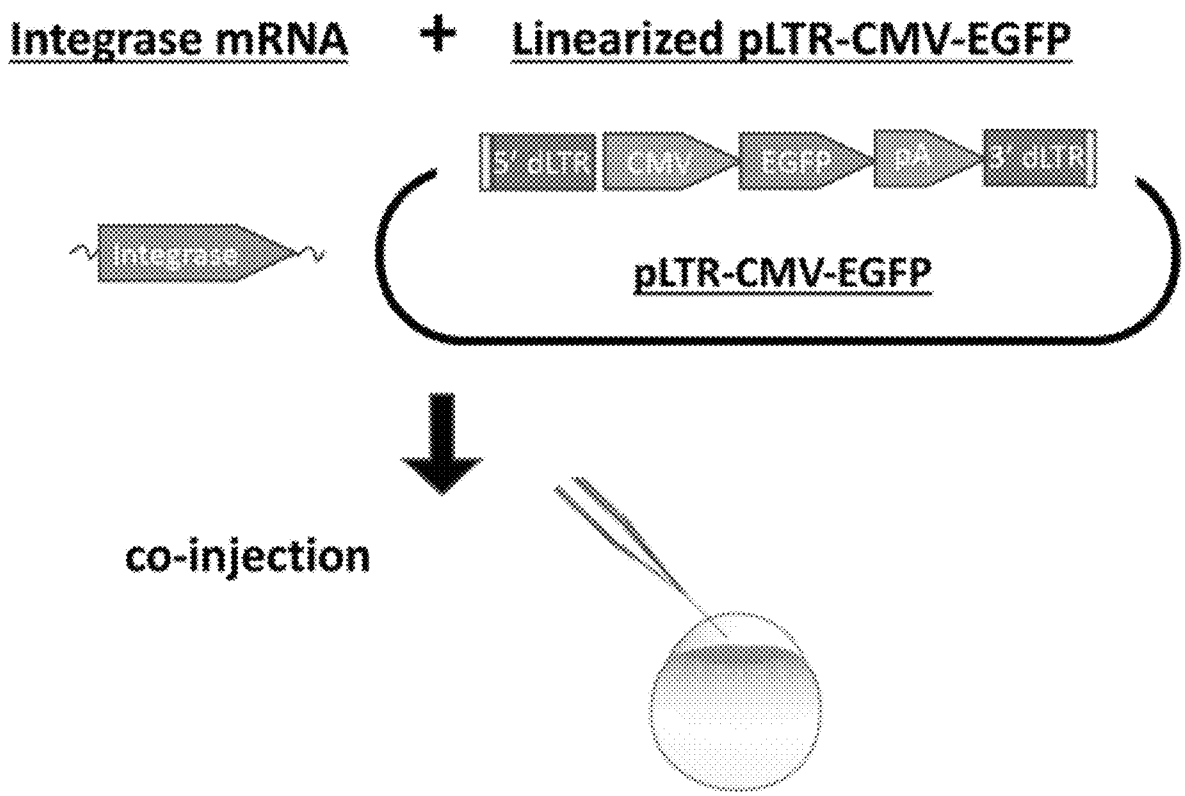

FIG. 13 shows schematic diagrams of the nucleic acids used for zebrafish injection and an outline of the experimental plan. "5' dLTR" and "3' dLTR" are truncated HIV-1 LTR sequences as described elsewhere herein. CMV indicates the cytomegalovirus early promoter. EGFP indicates sequences encoding enhanced green fluorescent protein. pA indicates the bovine growth hormone polyadenylation signal.

Figure 14:
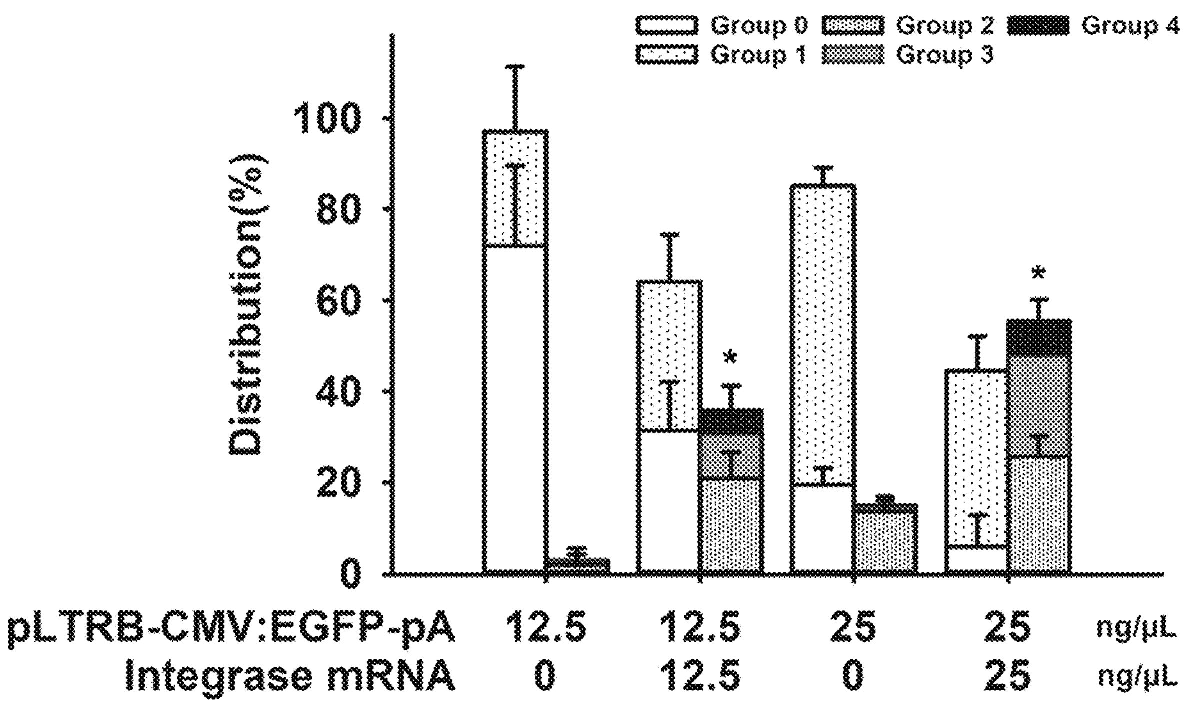

FIG. 14 shows a quantitative analysis of EGFP expression in zebrafish that developed from embryos that had been injected with integrase mRNA and a transgene cassette encoding enhanced green fluorescent protein. Analysis was conducted at two concentrations of each nucleic acid: a low dose of 12.5 ng/μl integrase mRNA and 12.5 ng/μl EGFP transgene cassette (second pair of bars from left), and a high dose of 25 integrase mRNA and 25 ng/μl EGFP transgene cassette (fourth pair of bars from left). Control samples were injected with 12.5 ng/μl (left-most pair of bars) or 25 ng/μl (third pair of bars from left) EGFP transgene cassette only (i.e., in the absence of integrase mRNA).

Fish were sorted into five groups depending on degree of expression of the transgene (Group 0: no expression through Group 4:highest level of expression), and results are expressed as the percentage of total individuals examined that fell into each group. For each pair of bars, white coloring indicates the percentage of fish in Group 0; light stippling indicates the percentage of fish in Group 1; heavy stippling indicates the percentage of fish in Group 2; dark shading indicates the percentage of fish in Group 3; and black indicates the percentage of fish in Group 4.

Figure 15:
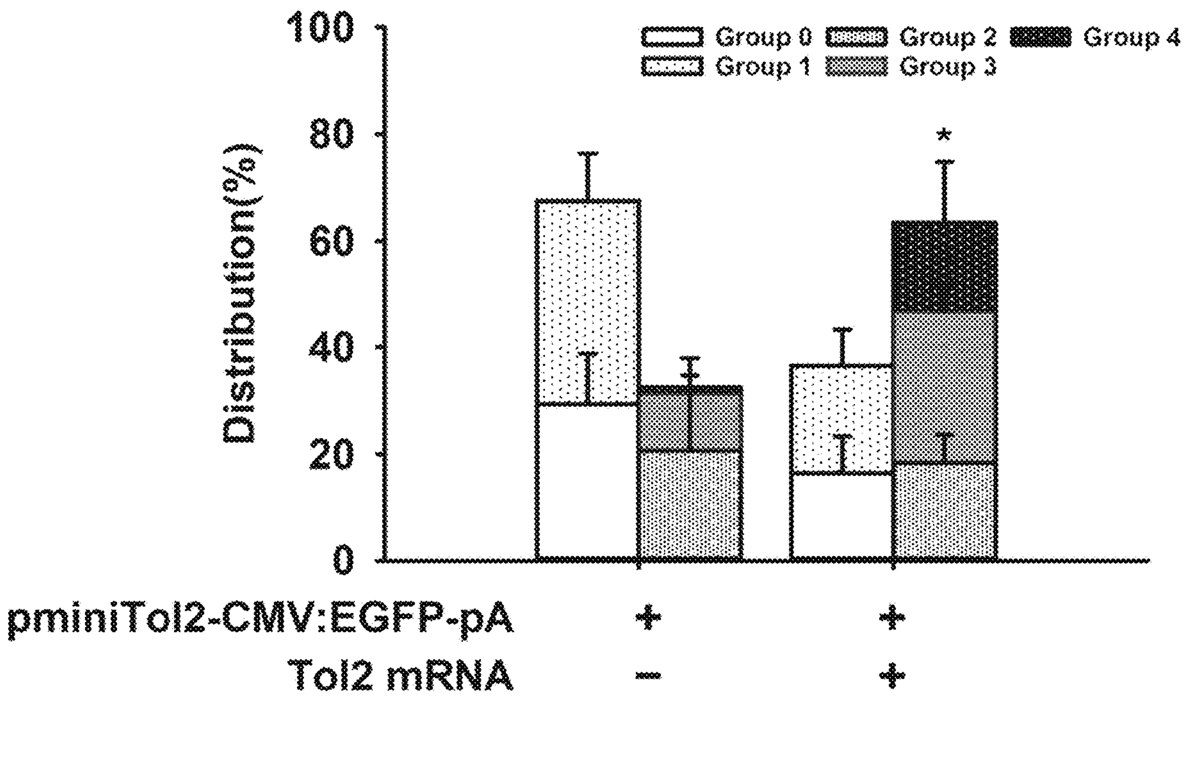

FIG. 15 shows a quantitative analysis of EGFP expression in zebrafish in which a EGFP transgene was introduced using a Tol2-mediated transposition system (right-most pair of bars). Results from a control experiment which did not include Tol2 mRNA are shown in the left-most pair of bars. The percentage of fish in each group (Group 0 through Group 4) is indicated by shading, as in FIG. 14.

Figure 16:
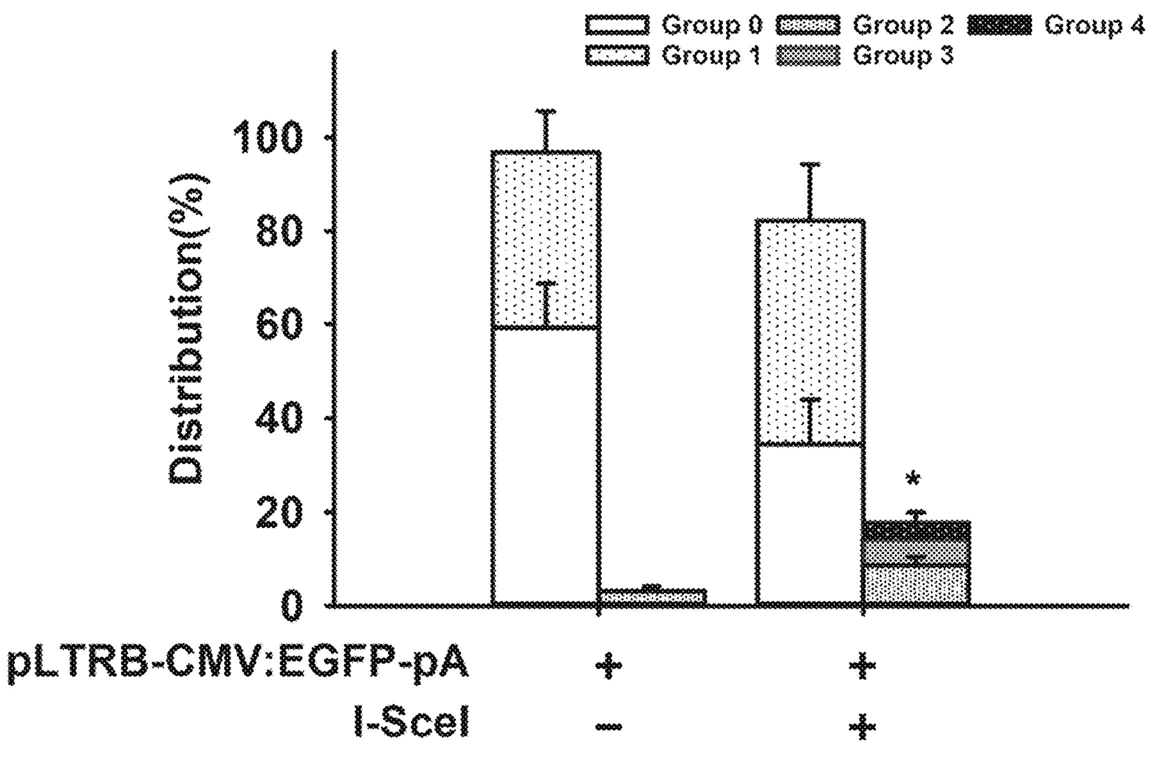

FIG. 16 shows a quantitative analysis of EGFP expression in zebrafish in which a EGFP transgene was introduced using I-SceI meganuclease-mediated integration (right-most pair of bars. Results from a control experiment which did not include the I-SceI meganuclease are shown in the left-most pair of bars. The percentage of fish in each group (Group 0 through Group 4) is indicated by shading, as in FIG. 14.

Figure 17:
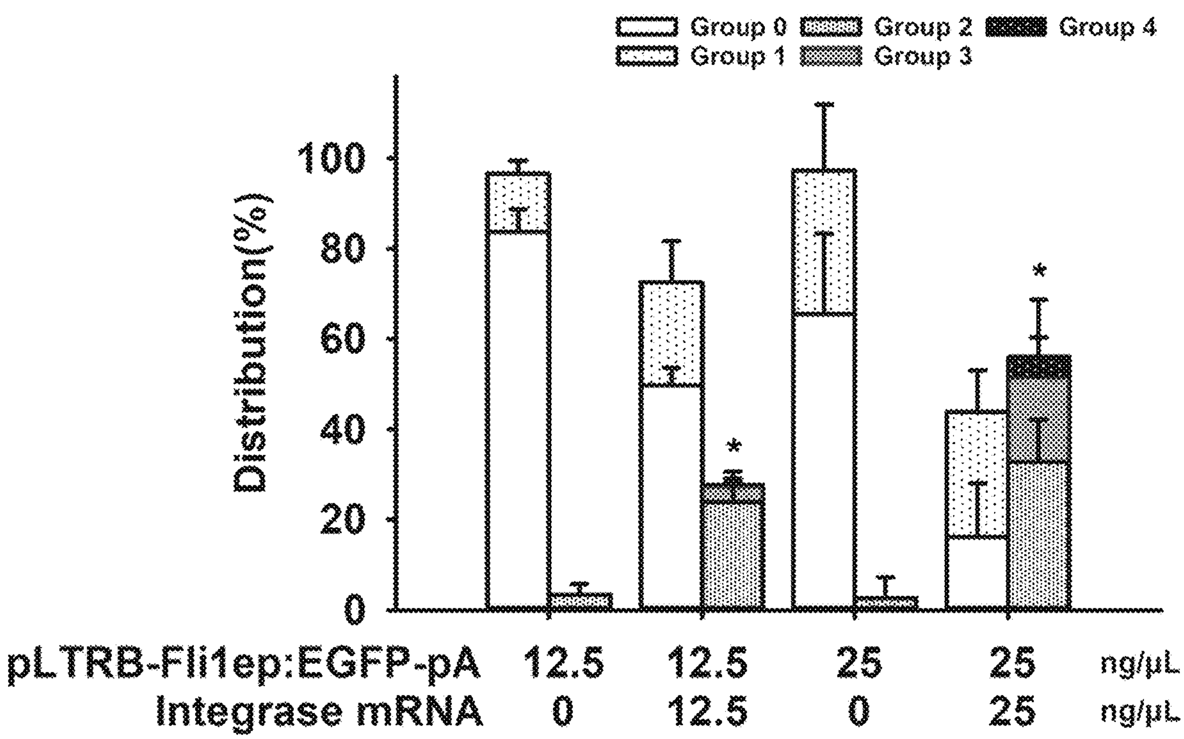

FIG. 17 shows a quantitative analysis of EGFP expression in zebrafish that developed from embryos that had been injected with integrase mRNA and a transgene cassette containing sequences encoding enhanced green fluorescent protein under the transcriptional control of the endothelial-specific Flilep enhancer. Analysis was conducted at two concentrations of nucleic acid: a low dose of 12.5 ng/μl integrase mRNA and 12.5 ng/μl EGFP transgene cassette (second pair of bars from left), and a high dose of 25 integrase mRNA and 25 ng/μl EGFP transgene cassette (fourth pair of bars from left). Control samples were injected with 12.5 ng/μl (left-most pair of bars) or 25 ng/μl (third pair of bars from left) EGFP transgene cassette only (i.e., in the absence of integrase mRNA).

Fish were sorted into five groups depending on degree of expression of the transgene, and results are expressed as the percentage of total individuals examined that fell into each group. The percentage of fish in each group (Group 0 through Group 4) is indicated by shading, as in FIG. 14.

Figure 18:
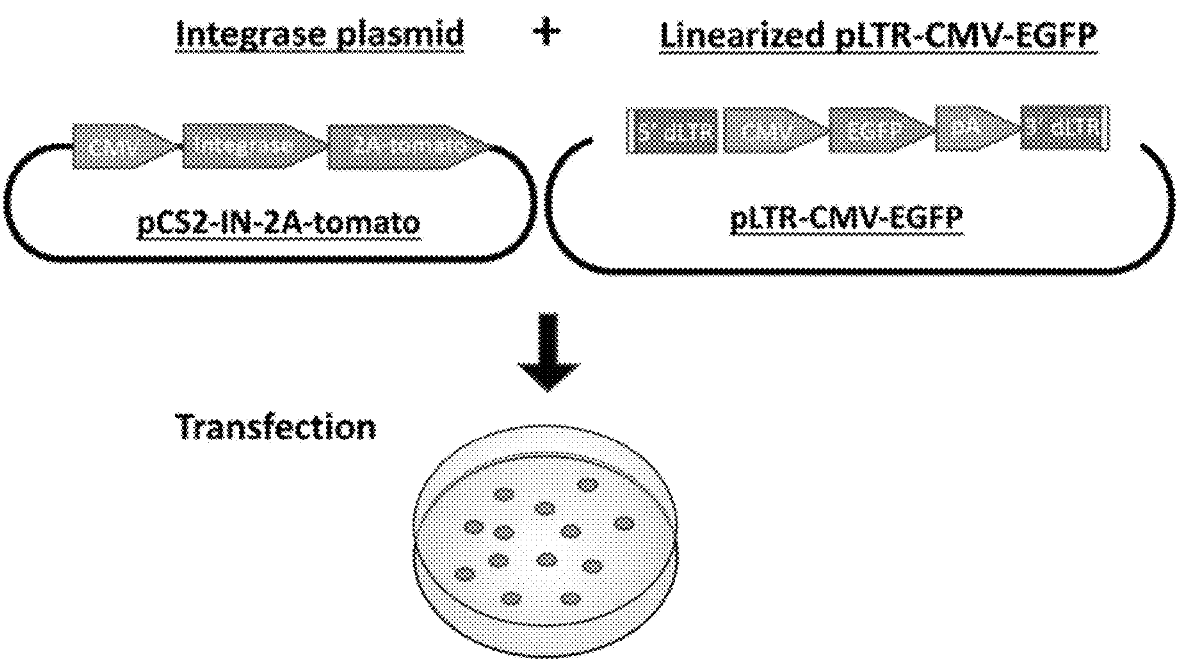

FIG. 18 shows schematic diagrams of the nucleic acids used for transfection of cultured cells and an outline of the experimental plan. "CMV" indicates the cytomegalovirus early promoter. "Integrase" indicates sequences encoding the HIV-1 integrase protein. "2A-tomato" indicates sequences encoding a red fluorescent protein. "5' dLTR" and "3' dLTR" are truncated HIV-1 LTR sequences as described elsewhere herein. EGFP indicates sequences encoding enhanced green fluorescent protein. pA indicates the bovine growth hormone polyadenylation signal.

Figure 19:
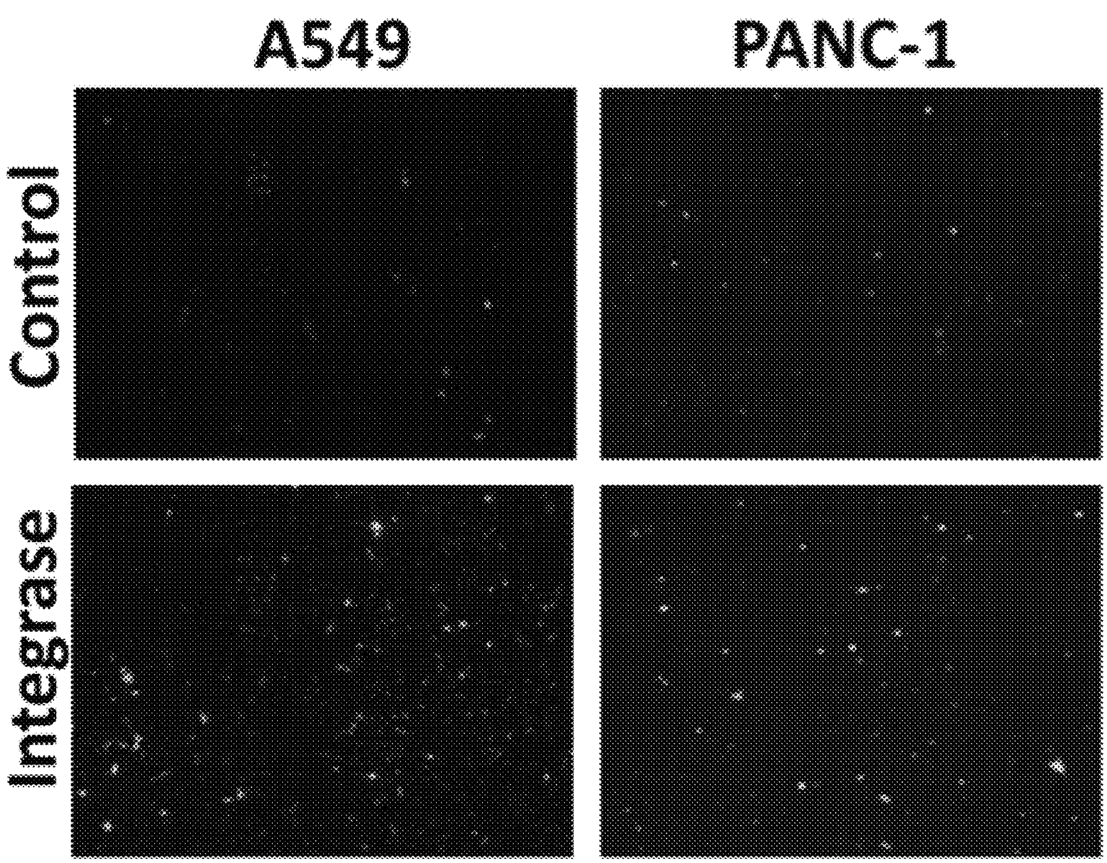

FIG. 19 shows representative fluorescent micrographic images of cultured cells from two cell lines (A549 and PANC-1) that had been transfected with a transgene cassette encoding EGFP. The upper panels ("Control") show images of cells transfected with an EGFP-encoding transgene cassette and a 2A-tomato-encoding vector. The lower panels ("Integrase") show images of cells transfected with an EGFP-encoding transgene cassette and a vector encoding HIV-1 integrase and 2A-tomato. Fluorescence is indicative of stable integration of the transgene into the cellular genome.

Figure 20:
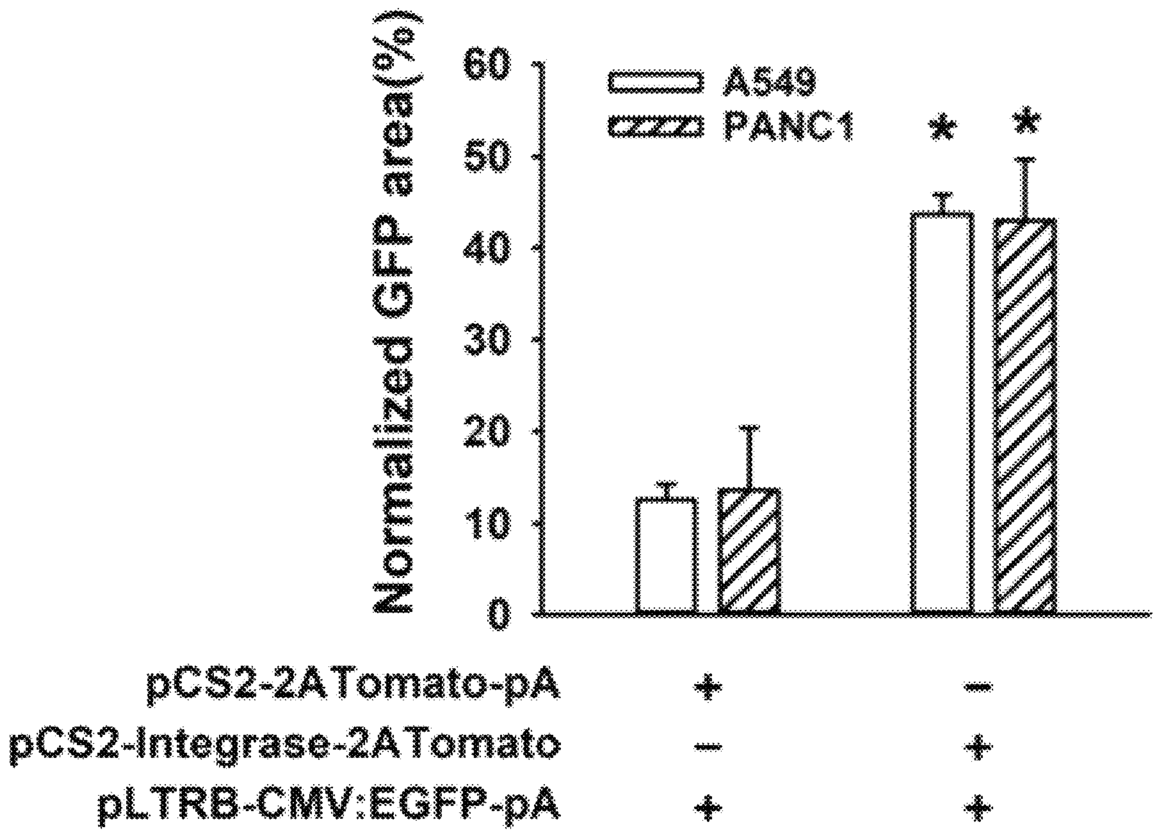

FIG. 20 shows results of measurement of the percentage of cells exhibiting green fluorescence, which is indicative of stable integration of an EGFP-encoding transgene. The right-most pair of bars shows results obtained with cells transfected with an EGFP-encoding transgene cassette and a plasmid encoding HIV-1 integrase. The left-most pair of bars shows results obtained with cells transfected with an EGFP-encoding transgene cassette and a control plasmid lacking integrase-encoding sequences. The left-most bar in each pair shows results for A549 cells; the right-most bar in each pair shows results for PANC-1 cells.

Figure 21:
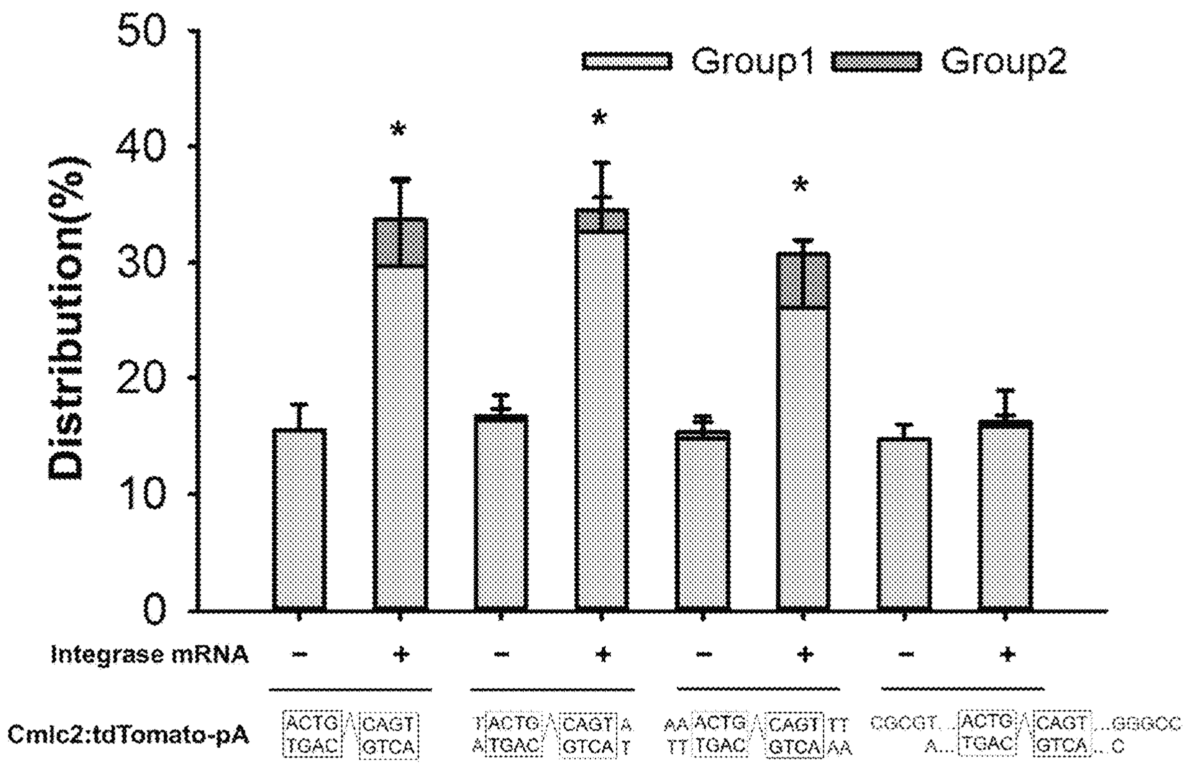

FIG. 21 shows percentage of zebrafish stably expressing a tdTomato transgene after injection of embryos with tdTomato transgene cassettes terminating in ScaI ends (left-most pair of bars) BstZ17I ends (second pair of bars from left), PmeI ends (third pair of bars from left) or ends generated by double digestion with Apa I and MluI (right-most pair of bars). The sequence in and adjacent to the recognition site for each enzyme, or enzyme pair, is shown below each pair of bars.

For each pair of bars, the right-most bar (indicated by "+" beneath the graph) shows percentage of individuals stably expressing red fluorescence after co-injection of tdTomato-containing transgene cassette and integrase mRNA; the left-most bar (indicated by "–" beneath the graph) shows results of control injections of tdTomato-containing transgene cassette only. Fish were sorted into groups depending on their degree of red fluorescence: fish in Group 1 (indicated by light shading) exhibited partial fluorescence in heart; and fish in Group 2 (indicated by darker shading) exhibited full fluorescence in heart.

Figure 22:
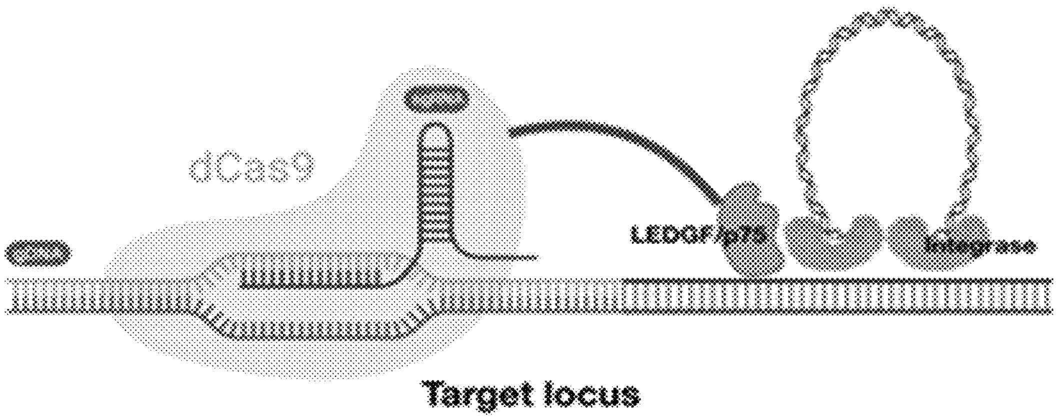

FIG. 22 is a schematic diagram illustrating the method used for targeted integration. A dCAs9/LEDGF (psip1a) fusion protein is recruited to the target sequence by a sgRNA having a portion complementary to the target sequence and a hairpin portion that binds dCas9. LEDGF in turn binds to the pre-integration complex (comprising integrase bound at both termini of the transgene cassette, on right of diagram), thereby tethering the pre-integration complex to the target sequence and directing integration at the target sequence.

Figure 23:
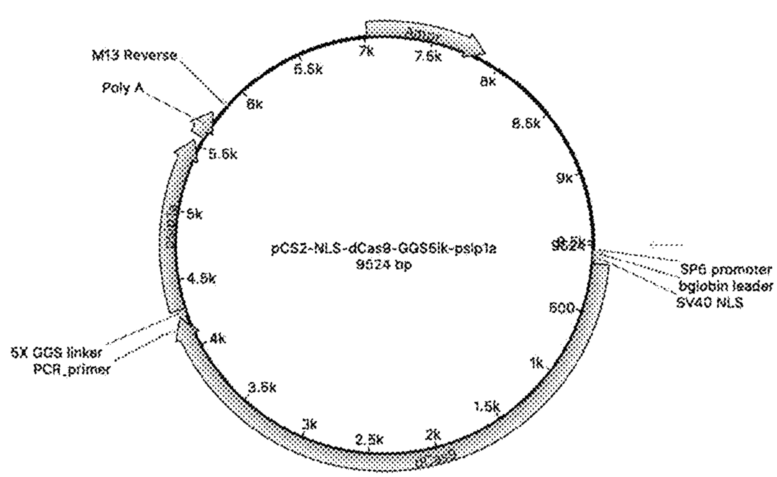

FIG. 23 is a schematic diagram of the pCS-NLS-dCas9-$(GGS)_5$-zpsip1a vector.

Figure 24:
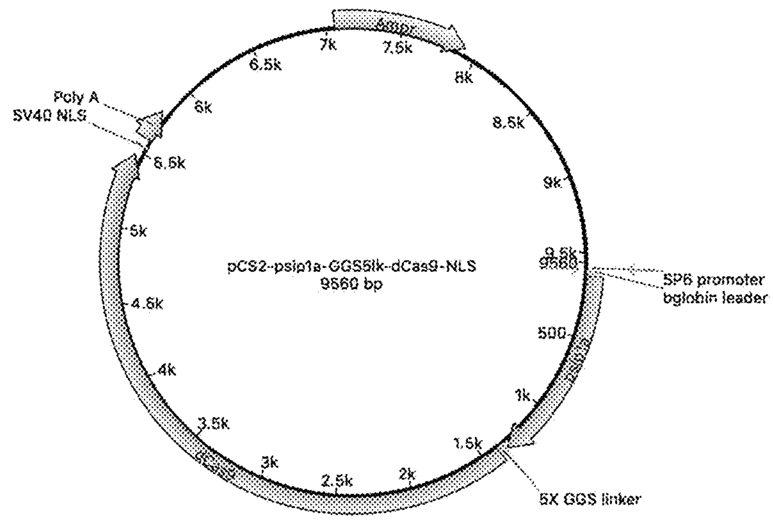

FIG. 24 is a schematic diagram of the pCS-zpsip1a-(GGS)5-dCas9-NLS vector.

Figure 25:
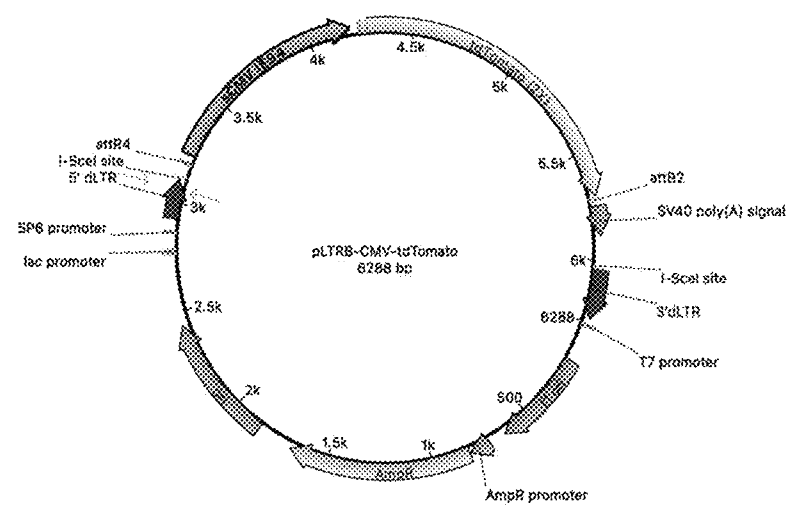

FIG. 25 is a schematic diagram of the pLTRB-CMV-tdTomato vector.

Figure 26:
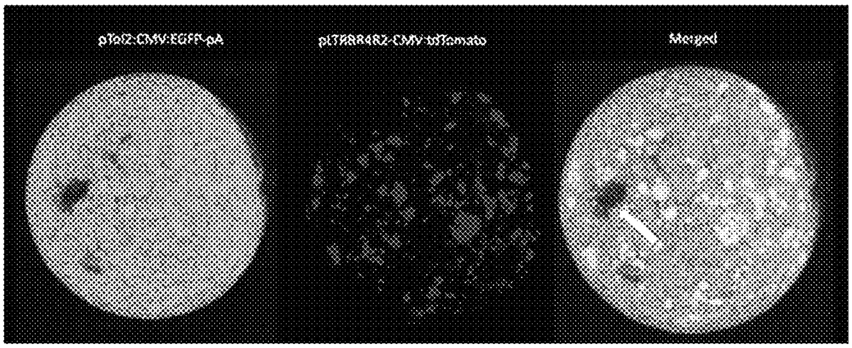

FIG. 26 shows Z-stack fluorescent confocal images of zebrafish embryos at 5 hours post-fertilization, showing green fluorescence (left), red fluorescence (center) and merged fluorescence (right). Several red cells (arrow) are visible in the merged image.

Figure 27:
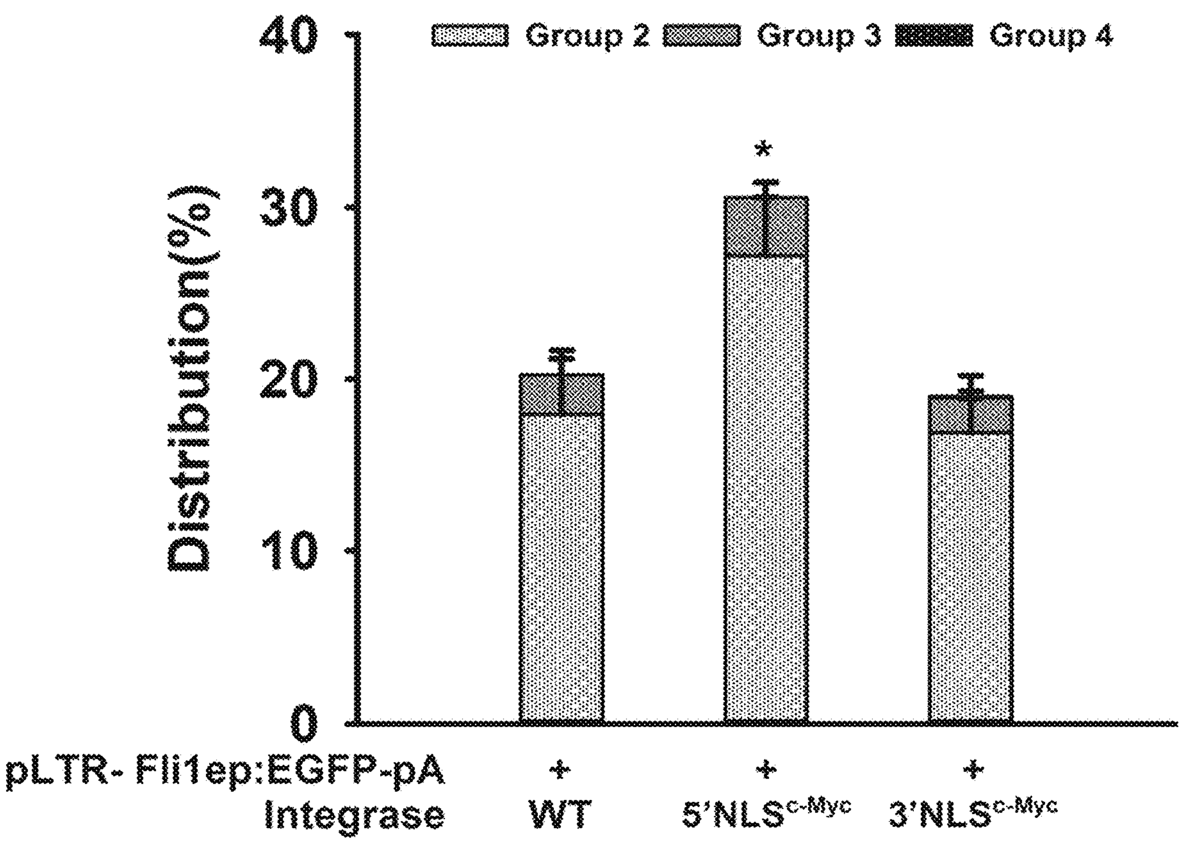

FIG. 27 shows the percentage of embryos exhibiting positive fluorescence (i.e., in groups 2, 3 or 4) after co-injection of a transgene cassette and mRNA encoding HIV-1 integrase protein or variants thereof. The transgene cassette, containing sequences encoding EGFP under the transcriptional control of an endothelium-specific enhancer (pFLi1ep:EGFP-pA), was co-injected with sequences encoding wild-type HIV-1 integrase (WT, left-most bar); sequences encoding an integrase variant containing a c-myc NLS appended to the N-terminus (5'$NLS^{c\text{-}myc}$, center bar) or sequences encoding an integrase variant containing a c-myc NLS appended to the C-terminus (3'$NLS^{c\text{-}myc}$, right-most bar). Fish were sorted into groups as shown, with Group 2 showing the lowest degree of fluorescence, and Group 4 showing the highest degree of fluorescence.

DETAILED DESCRIPTION

Practice of the present disclosure employs, unless otherwise indicated, standard methods and conventional techniques in the fields of cell biology, molecular biology, biochemistry, cell culture, recombinant DNA and related fields as are within the skill of the art. Such techniques are described in the literature and thereby available to those of skill in the art. See, for example, Alberts, B. et al., "Molecular Biology of the Cell," $6^{th}$ edition, Garland Science, New York, N.Y., 2015; Watson et al., "Molecular Biology of the Gene," $7^{th}$ edition, Pearson, London, 2014; Lodish et al. "Molecular Cell Biology," $8^{th}$ edition, W.H. Freeman, New York, N.Y., 2016; Voet, D. et al. "Fundamentals of Biochemistry: Life at the Molecular Level," $5^{th}$ edition, John Wiley & Sons, Hoboken, NJ, 2016; Sambrook, J. et al., "Molecular Cloning: A Laboratory Manual," $3^{rd}$ edition, Cold Spring Harbor Laboratory Press, 2001; Ausubel, F. et al., "Current Protocols in Molecular Biology," John Wiley & Sons, New York, 1987 and periodic updates; Freshney, R. I., "Culture of Animal Cells: A Manual of Basic Technique," $4^{th}$ edition, John Wiley & Sons, Somerset, N J, 2000; and the series "Methods in Enzymology," Academic Press, San Diego, CA.

I. Definitions

A "transgene vector," or "pLTR vector," as disclosed herein, is a DNA plasmid vector which, when cleaved by an appropriate restriction enzyme, generates a DNA molecule that resembles the substrate for integration of a retroviral DNA genome. Transgene vectors are characterized by sequences that facilitate introduction of an exogenous gene (e.g., att sites), flanked by truncated retroviral long terminal repeat (LTR) sequences, which are in turn flanked by the sequence 5'-ACTG-3', which in turn overlaps with, or is flanked by, recognition sites for a restriction enzyme whose cleavage generates blunt ends and whose recognition sequence optionally contains six or more nucleotides. A transgene vector suitable for insertion of a transgene, but which do not comprise a transgene, is denoted an "insertion vector."

A "transgene" is any DNA sequence inserted into a transgene vector as described herein. A transgene will often be a sequence encoding a protein, but can also be, e.g., a regulatory sequence (e.g., promoter, enhancer) or a sequence encoding a regulatory RNA, such as an antisense RNA or a siRNA.

A "transgene cassette" refers to a nucleic acid (e.g., DNA) molecule comprising a transgene (or one or more selection markers) flanked by sequences promoting recombination (e.g., att sites), which recombination-promoting sequences are in turn flanked by truncated LTR sequences, which truncated LTR sequences are in turn flanked by 5'-ACTG-3' sequences, which 5'-ACTG-3' sequences in turn overlap with, or are flanked by, recognition sequences for a restriction enzyme that, upon cleavage, generates blunt ends. A transgene cassette can be a portion of a transgene vector, wherein the transgene vector contains additional sequences such as, for example, replication origins, transcriptional regulatory sequences and additional selection markers. A transgene cassette can an isolated DNA molecule resulting from cleavage of a transgene vector with a blunt end-generating restriction enzyme as described herein. A transgene cassette may or may not comprise a transgene; if a transgene cassette comprises a transgene, it is denoted a "transgene-containing transgene cassette."

The terms "interior" (or "internal") and "exterior" (or "external") refer to relative location within a transgene cassette or transgene vector. Taking the transgene (or the selection marker(s) present in the vector before insertion of the transgene) as center; a first element being "interior to" a second element means that the first element is closer to the transgene (or selection marker) than is the second element. Alternatively, a first element being "exterior to" a second element means that the second element is closer to the transgene (or selection marker) than is the first element.

An "integrase vector," as disclosed herein, is a DNA plasmid vector containing sequences encoding a retroviral or lentiviral integrase protein. An integrase vector can also contain control sequences that regulate expression of the integrase protein. Such control sequences can be, for example, promoters for in vitro transcription, such as, for example, a SP6 promoter or a T7 promoter or the like; or a promoter (optionally in operative linkage with an enhancer) able to function in a eukaryotic cell. Such promoters and enhancers are known in the art. Sites specifying transcription termination and polyadenylation can also be present.

A restriction enzyme recognition site (or recognition sequence) is a DNA sequence to which a restriction enzyme binds in the process of DNA cleavage by the restriction enzyme. For most restriction enzymes, their recognition site is also the site at which the restriction enzyme cleaves DNA. However, certain restriction enzymes (e.g., FokI) cleave at a site that is distinct from the sequence at which they bind.

Cleavage of DNA by a restriction enzyme generates two DNA ends at the site of cleavage. If the terminal nucleotide of those ends is base-paired, the ends are denoted "blunt ends." If one or more of the 5'-terminal nucleotides are not base-paired, the ends are said to have a 5' extension or a 5'-overhang. If one or more of the 3'-terminal nucleotides are not base-paired, the ends are said to have a 3' extension or a 3'-overhang. 5'- and 3'-overhangs can consist of one, two, three, four or more unpaired nucleotides.

II. Homology and Identity of Nucleic Acids

"Homology" or "identity" or "similarity" as used herein refers to the relationship between two nucleic acid molecules based on an alignment of their nucleotide sequences. Homology and identity can each be determined by comparing a position in each sequence which may be aligned for purposes of comparison. For example, a "reference sequence" can be compared with a "test sequence." When a position in the reference sequence is occupied by the same nucleotide at an equivalent position in the test sequence, then the molecules are identical at that position; when the equivalent position is occupied by a similar nucleotide residue (e.g., similar in steric and/or electronic nature, and/or in its hydrogen-bonding properties), then the molecules can be referred to as homologous (similar) at that position. The relatedness of two sequences, when expressed as a percentage of homology/similarity or identity, is a function of the number of identical or similar nucleotides at positions shared by the sequences being compared. In comparing two sequences, the absence of nucleotide residues, or presence of extra residues, in one sequence as compared to the other, also decreases the identity and homology/similarity.

As used herein, the term "identity" refers to the percentage of identical nucleotide residues at corresponding positions in two or more sequences when the sequences are aligned to maximize sequence matching, i.e., taking into account gaps and insertions. Identity can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the highest degree of match between the sequences tested. Moreover, methods to determine identity are codified in publicly available computer programs. Computer program methods to determine identity between two sequences include, but are not limited to, the GCG program package (Devereux et al. (1984) Nucleic Acids Research 12:387), BLASTP, BLASTN, and FASTA (Altschul et al. (1990) J. Molec. Biol. 215:403-410; Altschul et al. (1997) Nucleic Acids Res. 25:3389-3402). The BLAST X program is publicly available from NCBI and other sources. See, e.g., BLAST Manual, Altschul, S., et al., NCBI NLM NIH Bethesda, Md. 20894; Altschul et al. (1990) J. Mol. Biol. 215:403-410. The well known Smith-Waterman algorithm can also be used to determine identity.

For sequence comparison, typically one sequence acts as a reference sequence, to which one or more test sequences are compared. Sequences are generally aligned for maximum correspondence over a designated region, e.g., a region at least about 15, 20, 25, 30, 35, 40, 45, 50, 55, 60, 65 or more nucleotides in length, and the region can be as long as the full-length of the reference nucleotide sequence. When using a sequence comparison algorithm, test and reference sequences are input into a computer program, subsequence coordinates are designated, if necessary, and sequence algorithm program parameters are designated. The sequence comparison algorithm then calculates the percent sequence identity for the test sequence(s) relative to the reference sequence, based on the designated program parameters.

Examples of algorithms that are suitable for determining percent sequence identity are the BLAST and BLAST 2.0 algorithms, which are described in Altschul et al. (1990) J. Mol. Biol. 215:403-410 and Altschul et al. (1977) Nucleic Acids Res. 25:3389-3402, respectively. Software for performing BLAST analyses is publicly available through the National Center for Biotechnology Information at www.ncbi.nlm.nih.gov (visited Jul. 22, 2019). Further exemplary algorithms include ClustalW (Higgins et al. (1994) Nucleic Acids Res. 22:4673-4680), available at www.ebi.ac.uk/Tools/clustalw/index.html (visited Jul. 22, 2019).

Sequence identity between two nucleic acids can also be described in terms of annealing, reassociation, or hybridization of two polynucleotides to each other, mediated by base-pairing. Hybridization between polynucleotides proceeds according to well-known and art-recognized base-pairing properties, such that adenine base-pairs with thymine or uracil, and guanine base-pairs with cytosine. The property of a nucleotide that allows it to base-pair with a second nucleotide is called complementarity. Thus, adenine is complementary to both thymine and uracil, and vice versa; similarly, guanine is complementary to cytosine and vice versa. An oligonucleotide or polynucleotide which is complementary along its entire length with a target sequence is said to be perfectly complementary, perfectly matched, or fully complementary to the target sequence, and vice versa. Two polynucleotides can have related sequences, wherein the majority of bases in the two sequences are complementary, but one or more bases are noncomplementary, or mismatched. In such a case, the sequences can be said to be substantially complementary to one another. If two polynucleotide sequences are such that they are complementary at all nucleotide positions except one, the sequences have a single nucleotide mismatch with respect to each other.

Conditions for hybridization are well-known to those of skill in the art and can be varied within relatively wide limits. Hybridization stringency refers to the degree to which hybridization conditions disfavor the formation of hybrids containing mismatched nucleotides, thereby promoting the formation of perfectly matched hybrids or hybrids containing fewer mismatches; with higher stringency correlated with a lower tolerance for mismatched hybrids. Factors that affect the stringency of hybridization include, but are not limited to, temperature, pH, ionic strength, and concentration of organic solvents such as formamide and dimethylsulfoxide. As is well known to those of skill in the art, hybridization stringency is increased by higher temperatures, lower ionic strengths, and lower solvent concentrations. See, for example, Ausubel et al., supra; Sambrook et al., supra; M. A. Innis et al. (eds.) PCR Protocols, Academic Press, San Diego, 1990; B. D. Hames et al. (eds.) Nucleic Acid Hybridisation: A Practical Approach, IRL Press, Oxford, 1985; and van Ness et al., (1991) Nucleic Acids Res. 19:5143-5151.

Thus, in the formation of hybrids (duplexes) between two polynucleotides, the polynucleotides are incubated together in solution under conditions of temperature, ionic strength, pH, etc., that are favorable to hybridization, i.e., under hybridization conditions. Hybridization conditions are chosen, in some circumstances, to favor hybridization between two nucleic acids having perfectly-matched sequences, as compared to a pair of nucleic acids having one or more mismatches in the hybridizing sequence. In other circumstances, hybridization conditions are chosen to allow hybridization between mismatched sequences, favoring hybridization between nucleic acids having fewer mismatches.

The degree of hybridization between two polynucleotides, also known as hybridization strength, is determined by methods that are well-known in the art. A preferred method is to determine the melting temperature ($T_m$) of the hybrid duplex. This is accomplished, for example, by subjecting a duplex in solution to gradually increasing temperature and monitoring the denaturation of the duplex, for example, by absorbance of ultraviolet light, which increases with the unstacking of base pairs that accompanies denaturation. $T_m$ is generally defined as the temperature midpoint of the transition in ultraviolet absorbance that accompanies denaturation. Alternatively, if $T_m$s are known, a hybridization temperature (at fixed ionic strength, pH and solvent concentration) can be chosen that is below the $T_m$ of the desired duplex and above the $T_m$ of an undesired duplex. In this case, determination of the degree of hybridization is accomplished simply by testing for the presence of duplex polynucleotide. Adsorption to hydroxyapatite can also be used to distinguish single-stranded nucleic acids from double-stranded nucleic acids.

Hybridization conditions are selected following standard methods in the art. See, for example, Sambrook, et al., Molecular Cloning: A Laboratory Manual, Second Edition, (1989) Cold Spring Harbor, N.Y. For example, hybridization reactions can be conducted under stringent conditions. An example of stringent hybridization conditions is hybridization at 50° C. or higher in 0.1×SSC (15 mM sodium chloride/1.5 mM sodium citrate). Another example of stringent hybridization conditions is overnight incubation at 42° C. in a solution: 50% formamide, 5×SSC (0.75 M NaCl, 75 mM trisodium citrate), 50 mM sodium phosphate (pH7.6), followed by washing in 0.1×SSC at about 65° C. Optionally, one or more of 5×Denhardt's solution, 10% dextran sulfate, and/or 20 mg/ml heterologous nucleic acid (e.g., yeast tRNA, denatured, sheared salmon sperm DNA) can be included in a hybridization reaction. Stringent hybridization conditions are hybridization conditions that are at least as stringent as the above representative conditions, where conditions are considered to be at least as stringent if they are at least about 80% as stringent, typically at least 90% as stringent as the above specific stringent conditions.

The term "substantially identical" is used herein to refer to a first nucleic acid sequence that contains a sufficient or minimum number of nucleotides that are identical to aligned nucleotides in a second nucleic acid sequence such that the first and second nucleotide sequences possess a common functional property (e.g., enhancing the expression, stability or transport of mRNA).

The term "homology" describes a mathematically based comparison of sequence similarities which is used to identify sequences with similar functions or motifs. A reference nucleotide sequence (e.g., a sequence as disclosed herein) is used as a "query sequence" to perform a search against public databases to, for example, identify other family members, related sequences or homologues. Such searches can be performed using the NBLAST and XBLAST programs (version 2.0) of Altschul et al. (1990) J. Mol. Biol. 215:403-410. BLAST nucleotide searches can be performed with the NBLAST program, score=100, wordlength=12 to obtain nucleotide sequences homologous to a reference nucleotide sequence. To obtain gapped alignments for comparison purposes, Gapped BLAST can be utilized as described in Altschul et al. (1997) Nucleic Acids Res. 25:3389-3402. When utilizing the BLAST and Gapped BLAST programs, the default parameters of the respective programs (e.g., XBLAST and BLAST) can be used (see ncbi.nlm.nih.gov).

Nucleic acids and polynucleotides of the present disclosure encompass those having a nucleotide sequence that is at least 50%, at least 60%, at least 70%, at least 75%, at least 80%, at least 85%, at least 90%, at least 95%, at least 96%, at least 97%, at least 98%, at least 99%, at least 99.9% or 100% identical to any of SEQ ID NOs:1-5.

Nucleotide analogues are known in the art. Accordingly, nucleic acids (i.e., SEQ ID NOs:1-5) comprising nucleotide analogues are also encompassed by the present disclosure.

III. Transgene Vectors and Transgene Cassettes

Figure 3:
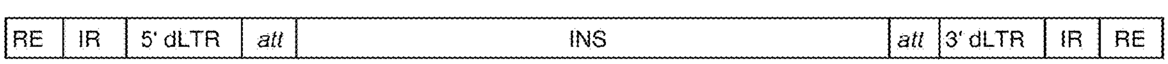
FIG. 3 shows a schematic diagram (not to scale) of an exemplary transgene cassette. RE indicates a recognition site for a restriction enzyme that generates a blunt-ended cleavage product (e.g., PmeI, ScaI or BstZ17I). IR represents the inverted repeat sequence 5'-ACTG-3'. 5' dLTR represents the truncated LTR sequence shown in FIG. 8B. 3' dLTR represents the truncated LTR sequence shown in FIG. 9B. att represents an att site. INS represents a transgene. The RE and IR sites may overlap each other.
Figure 4:
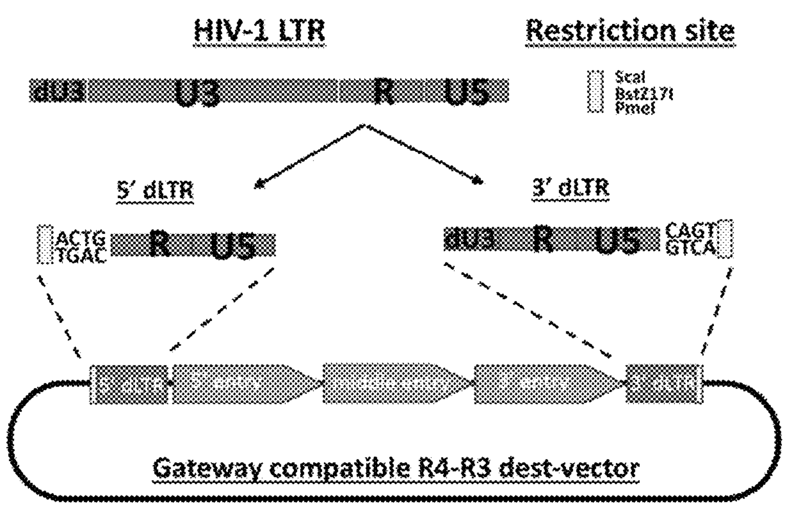
FIG. 4 is a schematic diagram of a transgene vector. The top row of the diagram shows regions of the HIV-1 LTR (dU3, U3, R and U5) relevant to construction of the vector and also shows certain restriction sites that can be used in the vector. The middle row shows the structures of the ends of the transgene cassette: the light-colored box represents one of the three restriction sites shown in the top row, and the darker boxes represent portions of the LTR present in the 5' dLTR and 3' dLTR sequences. The sequence 5'-ACTG-3' is present between the restriction site and each dLTR sequence. The bottom row shows a diagram of a gateway-compatible vector containing the dLTRs shown in the middle row, along with 5' entry sequences, middle entry sequences, and 3' entry sequences for insertion of transgenes and regulatory sequences.

Transgene vectors are based on Gateway destination vectors and are designed so that, after insertion of transgene sequences; cleavage of the vector with an appropriate restriction enzyme generates a DNA molecule resembling a retroviral pre-integration substrate. Thus, a transgene vector contains a transgene cassette comprising one or more pairs of att sites to facilitate insertion of the transgene by Gateway cloning methods. The att sites are flanked externally by truncated retroviral (e.g., lentiviral) LTR sequences (denoted 5' dLTR and 3' dLTR herein) which, in turn, are flanked (externally) by the inverted repeat sequence 5'-ACTG-3'. The 5'-ACTG-3' sequences are flanked, in turn, by recognition sites for a restriction enzyme whose cleavage generates blunt-ended products. In certain embodiments, the 5'-ACTG-3' sequences overlap with the recognition site for the blunt end-generating restriction enzyme. In certain embodiments, the recognition sites are six nucleotide pairs or greater in length. A schematic diagram of a transgene cassette is shown in FIG. 3. A transgene cassette can be part of a DNA vector (e.g., a circular plasmid) or can exist as a linear, double-stranded DNA molecule. A schematic diagram of a transgene vector, designed for insertion of a transgene and/or regulatory elements by Gateway cloning, is shown in FIG. 4.

In certain embodiments of a transgene vector, one or more selection markers are located between the att sites, to allow for selection of vectors containing an inserted transgene. The selection marker can be a negative selection marker (e.g., the ccdB gene) that causes cell death or blocks cell growth; so that replacement of the negative selection marker by transgene sequences allows survival of cells harboring a transgene-containing vector. Selection markers are known in the art and include, for example, β-lactamase, ccdB, dihydrofolate reductase (DHFR), glutamine synthetase (GS), puromycin-N-acetyl transferase, hygromycin phosphotransferase, aminoglycoside-3-phosphotransferase, ble; and sequences encoding resistance to ampicillin, tetracycline, kanamycin, chloramphenicol, G418, gentamycin and neomycin.

A. Restriction Enzyme Recognition Sites

Integration of the retroviral double-stranded DNA genome requires a blunt-ended genome, terminating in the inverted repeat sequence

```
5'-ACTG-3'
3'-TGAC-5'
```

as a substrate for retroviral integrase activity. Accordingly, for transgene integration according to the present invention, the transgene is present on a blunt-ended DNA molecule; hence the restriction enzyme recognition sites that flank the transgene cassette are sites whose cleavage results in production of a blunt end (i.e., recognition sites for a blunt end-generating restriction enzyme) and whose recognition site contains all or part of the sequence 5'-ACTG-3'.

In addition, to avoid the possibility of cleavage within the transgene itself, it is preferable that the recognition site contain six nucleotide pairs or more; e.g., six nucleotide pairs, seven nucleotide pairs, eight nucleotide pairs, nine nucleotide pairs, ten nucleotide pairs, eleven nucleotide pairs, twelve nucleotide pairs or more. However, depending on the size and nucleotide sequence of the transgene, blunt end-generating restriction enzymes whose recognition sites contain four or five nucleotide pairs can also be used.

Exemplary restriction enzymes for use in the methods described herein, that produce blunt ends and whose recognition sequences contain all or part of the sequence 5'-ACTG-3', include Sca I, PmeI and BstZ17I, whose recognition sequences are shown in Table 1.

TABLE 1

Exemplary restriction enzymes and their recognition sequences*

| Enzyme | Recognition sequence |
|---|---|
| Sca I | 5'--AGT ACT--3'<br>3'--TCA TGA--5'<br>↑ |
| Pme I: | 5'--GTTT AAAC--3'<br>3'--CAAA TTTG--5'<br>↑ |
| Bst Z17I: | 5'--GTA TAC--3'<br>3'--CAT ATG--5'<br>↑ |

*Cleavage site is indicated by arrow

Additional restriction enzyme recognition sequence suitable for use in the transgene vectors described herein include those whose cleavage generates blunt ends terminating in the sequence 5'-ACTG-3', or in which the sequence 5'-ACTG-3' is within 1, 2, 3, 4 or 5 base pairs of a blunt-ended terminus. In addition, restriction enzymes generating 5'-overhanging ends which can be repaired by a DNA polymerase to generate (1) a blunt-end terminating in the sequence 5'-ACTG-3'; or (2) a blunt-ended in which the sequence 5'-ACTG-3' is within 1, 2, 3, 4 or 5 base pairs of the blunt-ended terminus, can also be used. Furthermore, restriction enzymes generating 3'-overhanging ends which can be processed by a protein having 3'-specific, single-stranded exonuclease activity (e.g., S1 nuclease, mung bean nuclease, *E. coli*. exonuclease I, *E. coli*. exonuclease X, *E. coli* DNA polymerase I, *E. coli* DNA polymerase II, *E. coli* DNA polymerase III, *E. coli* exonuclease T), to generate (1) a blunt-end terminating in the sequence 5'-ACTG-3'; or (2) a blunt-ended in which the sequence 5'-ACTG-3' is within 1, 2, 3, 4 or 5 base pairs of the blunt-ended terminus, can also be used.

B. Inverted Repeat Sequence

For integration of a double-stranded viral DNA genome into a host cell chromosome, the blunt-ended inverted repeat sequence

5'-ACTG-3'

3'-TGAC-5' is required at the termini of the double-stranded viral DNA genome. The 3'-processing activity of the viral integrase (int) protein removes the terminal GT dinucleotide, leaving a 5' extension of the dinucleotide AC at both ends of the DNA molecule, which allows the molecule to serve as a substrate for strand transfer (i.e., integration).

Accordingly, the transgene vectors disclosed herein contain, at both ends of the transgene cassette, the inverted repeat (IR) sequence

5'-ACTG-3'

3'-TGAC-5'.

This 5'-ACTG-3' sequence can be part of the blunt end-generating restriction enzyme recognition site (as discussed in the previous section) or can overlap, either fully or partially, with the recognition site.

C. Truncated LTRs

Figure 1:
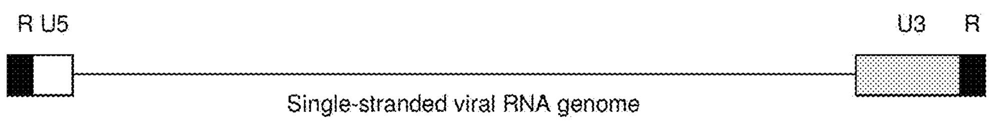
FIG. 1 is a schematic diagram of a retroviral single-stranded RNA genome, focusing on the terminal sequences. R signifies a repeated sequence present at both termini of viral RNA. U5 is a noncoding sequence unique to the 5' end of viral RNA. U3 is a noncoding sequence unique to the 3' end of viral RNA. The remainder of the viral genome (containing gag, pol, env and other genes) is represented by the horizontal line.

The termini of retroviral and lentiviral genomes consist of identical long terminal repeat (LTR) sequences. A typical LTR contains three sequence elements: U5, a sequence unique to the 5' end of the RNA genome; U3, a sequence unique to the 3' end of the RNA genome; and R, a sequence contained at both the 5' and 3' ends of the RNA genome external to the U5 and U3 sequences. A generalized structure of a retroviral RNA genome, focusing on the terminal sequences, is shown in FIG. 1.

Figure 2:
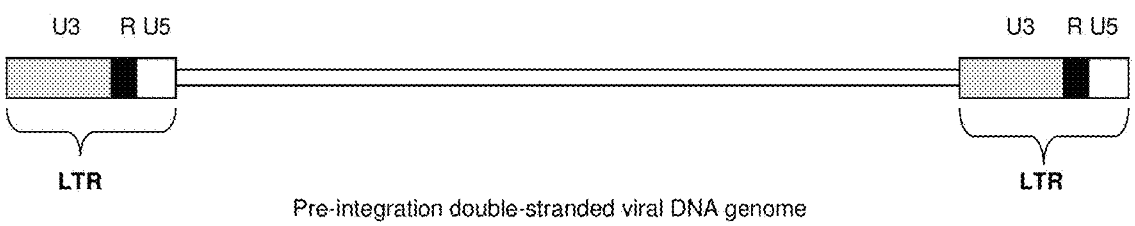
FIG. 2 is a schematic diagram of a retroviral double-stranded DNA genome, focusing on the terminal sequences. R signifies a repeated sequence present at both termini of viral RNA. U5 is a noncoding sequence unique to the 5' end of viral RNA. U3 is a noncoding sequence unique to the 3' end of viral RNA. The remainder of the viral genome (containing gag, pol, env and other genes) is represented by the horizontal lines. The long terminal repeat (LTR) regions of the double-stranded genome are indicated.

During the infective cycle, the single-stranded RNA genome is converted to a double-stranded DNA molecule. Due to the nature of the reverse transcription reaction, certain terminal genomic sequences are duplicated and transferred to the other end of the genome, generating long terminal repeat (LTR) sequences, as shown schematically in FIG. 2.

Figure 5:
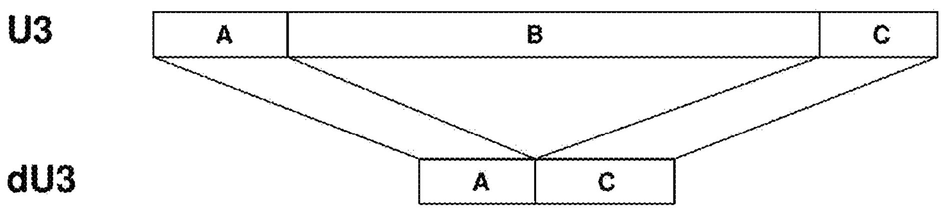
FIG. 5 is a schematic diagram (not to scale) illustrating construction of the dU3 sequence. The U3 sequence is arbitrarily divided into 3 regions: A, B and C. In the dU3 sequence, internal sequences represented by B have been deleted.
Figure 6:
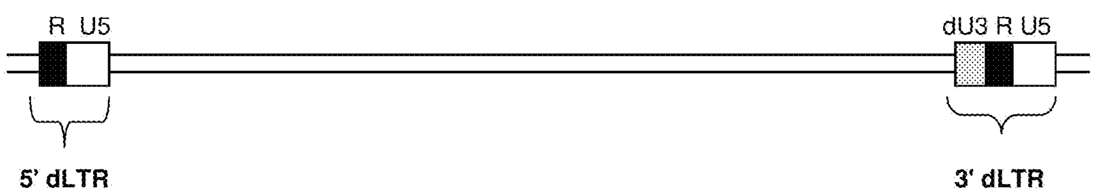
FIG. 6 is a schematic diagram of an exemplary transgene cassette, focusing on the 5' dLTR and 3' dLTR sequences. R signifies a repeated sequence present at both termini of viral RNA. U5 is a noncoding sequence unique to the 5' end of viral RNA. dU3 is a deleted U3 sequence. The remainder of the cassette is represented by the horizontal lines.

The LTR-containing double-stranded DNA genome is the substrate for integration; however, not all LTR sequences are required for integration of viral double-stranded DNA. In particular, many, if not all of the approximately 50 transcriptional regulatory elements, present in the U3 region, are unnecessary for integration. Accordingly, in the transgene vectors and transgene cassettes disclosed herein, not all U3 sequences are present in the truncated LTRs (dLTRs) present in the transgene vectors. In particular, the 5' dLTR does not contain any U3 sequences, consisting of R and U5 sequences; and the 3' dLTR contains an internally deleted U3 (dU3) region (that retains only the Sp1 and GATA-3 binding sites) along with R and U5 sequences. FIG. 5 shows a schematic diagrams of how U3 sequences were deleted to construct a dU3 sequence. A schematic diagram of the dLTR sequences of the transgene vectors and transgene cassettes is shown in FIG. 6.

The derivation of the 5' dLTR and 3' dLTR are shown in more detail in FIGS. 7-10. FIG. 7 shows the nucleotide sequence of the wild-type HIV-1 LTR, indicating the U3, R and U5 regions. FIG. 8A shows the sequence of the U3 region, indicating sequences which are deleted (no underlining) and sequences which are retained (underlined) in dU3. FIG. 8B show the nucleotide sequence of dU3. FIG. 9A shows the nucleotide sequence of the HIV-1 LTR and indicates the sequences present in 5' dLTR. FIG. 9B show the nucleotide sequence of the 5' dLTR which contains R and U5 sequences. FIG. 10A shows the nucleotide sequence of the HIV-1 LTR and indicates the sequences present in 3' dLTR. FIG. 10B show the nucleotide sequence of the 3' dLTR which contains dU3, R and U5 sequences.

D. att Sites

Transgene vectors are designed for rapid and simple insertion of transgenes using the gateway cloning system. See, for example, Hartley et al., supra. Accordingly, the transgene vectors disclosed herein, based on Gateway destination vectors, contain one or more pairs of att sites.

att sites are DNA sequences involved in the integration of the bacteriophage λ genome into, and its excision from, the *E. coli.* chromosome. The bacteriophage contains two sequence denoted attP, which, in the presence of a recombinase protein, recombine with a pair of bacterial sequence known as attB sites. The result of the recombination reaction is an *E. coli* genome containing an integrated λ genome, in which the integrated λ genome is flanked by hybrid att sites denoted attL and attR. Excision of an integrated λ genome is catalyzed by the xis protein, resulting in the regeneration of the attP sites in the phage genome and regeneration of the attB sites in the bacterial genome.

In a vector with a single pair of att sites, one att site lies just interior to the 5' dLTR sequence, and the other att site lies just interior to the 3' dLTR sequence. In certain embodiments, transgene vectors contain two pairs of att sites. In additional embodiments, transgene vectors contain three pairs of att sites: a first pair of att sites for 5' entry clones; a second pair of att sites for middle entry clones and a third pair of att sites for 3' entry clones as described, for example, by Kwan et al. (2007) Devel. Dynamics 236:3088-3099. Exemplary pairs of att sites include:

att L1 and att L2
att L3 and att L4
att R1 and att R2
att R3 and att R4
att B1 and att B2
att B3 and att B4
att P1 and att P2
att P3 and att P4

IV. Nucleic Acids Encoding Retroviral Integrase

Retroviral integrase proteins are encoded by a portion of the retroviral pol gene, near its 3' end. Integrase proteins comprise approximately 300 to 400 amino acids and include three domains, that are joined by linkers of varying length. The N-terminal domain includes two pairs of zinc-chelating histidine and cysteine residues (the HHCC motif) in which a bound $Zn^{2+}$ ion stabilizes a helix-turn-helix structure. The catalytic core domain is characterized by three acidic amino acids: two aspartic acid residues and a glutamic acid residue (the DDE motif) with the second aspartic acid and the glutamic acid being separated by approximately 35 residues. The DDE motif is also involved in metal ion chelation. Also within the central region of HIV-1 integrase is a non-canonical nuclear localization signal (NLS), having the amino acid sequence IIGQVRDQAEHLK (SEQ ID NO:12) which is in part responsible for the ability of HIV to infect non-dividing cells. The C-terminal domain of integrase proteins is the least well-conserved but contains β-strand barrels resembling that found in the SH3 domain and includes determinants for DNA binding and multimerization (retroviral integrases are active only as multimers: a dimer is capable of 3'-end processing, but a tetramer is required for strand transfer and integration). Certain retroviral integrases also contain a N-terminal extension.

A nucleic acid comprising sequences encoding a polypeptide having retroviral integrase activity can be, for example, a mRNA molecule. Such mRNA molecules can be generated, for example, by in vitro transcription of a DNA molecule having appropriate transcriptional control sequences such as, for example, a bacteriophage T7 promoter or a bacteriophage SP6 promoter. Transcription termination can be regulated by the presence of a transcriptional terminator sequence or a RNA molecule can be generated as the result of run-off transcription from a linear DNA template. Optionally, such integrase mRNAs contain translational regulatory sequences; e.g., a Kozak sequence or an internal ribosome entry site (IRES).

Alternatively, sequences encoding polypeptides having retroviral integrase activity are present in a DNA molecule, for example, a plasmid. In these cases, promoter and enhancer sequences, additional transcriptional regulatory sequences such as transcription termination signals and polyadenylation signals, insulators and translational regulatory sequences (such as Kozak sequences and internal ribosome entry sites) can also be present in the plasmid. See also Masuda (2011) Frontiers in Microbiology 2:1-5 (Article 210).

In additional embodiments, the disclosure provides integrase proteins (and nucleic acids encoding them) that have been engineered to contain one or more additional nuclear localization signals. For example, in addition to the endogenous NLS present in HIV-1 integrase; NLS sequences from SV40 (PKKKRKV, SEQ ID NO:13), c-myc (PAAKRVKLD, SEQ ID NO:14), the HIV Vpr protein (RRTRNGASKS, SEQ ID NO:15) and hnRNPA1 (SSNFGPMLGGNRFFRSSPY, SEQ ID NO:16) are introduced at the N-terminus and/or the C-terminus of the integrase protein. In certain embodiments, a linker sequence is present between the integrase protein and the exogenous nuclear localization signal(s) at the N- and/or C-terminus. Since different nuclear localization signals are recognized by different importin proteins (e.g., the HIV integrase NLS is recognized by importin α3 and the HIV Vpr NLS is recognized by importin al, while other NLS sequences are recognized by importin β); integrase proteins containing multiple different nuclear localization signals will accumulate at higher levels in cell nuclei; thereby increasing integration efficiency.

V. Regulatory Elements

The transgene cassettes and transgene vectors disclosed herein are gateway compatible; accordingly, it is straightforward to include not only coding sequences, but also 5' and 3' regulatory sequences, such as, for example, enhancers, promoters, transcription termination sites, polyadenylation signals and translation initiation sites; using two-way or three-way gateway cloning protocols. Accordingly, transgene-containing transgene cassettes, and integrated transgenes obtained by the methods described herein, can contain transcriptional and translational regulatory sequences to control the expression (e.g., temporal expression and/or regional expression) of the integrated transgene. Certain regulatory sequences, known in the art, can also provide constitutive expression of a transgene (e.g., actin promoter, CMV promoter, 3-GPDH promoter, ribosomal promoters).

Transcriptional regulatory sequences include, for instance, promoters, enhancers, polyadenylation signals and insulators.

Promoters active in eukaryotic cells are known in the art and include, for example viral promoters (e.g., SV40 early promoter, SV40 late promoter, cytomegalovirus major immediate early (MIE) promoter, herpes simplex virus thymidine kinase (HSV-TK) promoter), EF1-alpha (translation elongation factor-1 α subunit) promoter, Ubc (ubiquitin C) promoter, PGK (phosphoglycerate kinase) promoter, actin promoter and others. See also Boshart et al., GenBank Accession No. K03104; Uetsuki et al. (1989) J. Biol. Chem. 264:5791-5798; Schorpp et al. (1996) Nucleic Acids Res. 24:1787-1788; Hamaguchi et al. (2000) J. Virology 74:10778-10784; and Dreos et al. (2013) Nucleic Acids Res. 41(D1):D157-D164. Tissue-specific promoters, such as the cMLC2 promoter, which specifies transcription in myocardial cells, can also be used.

Enhancer elements, and their nucleotide sequences, are known in the art. Certain enhancers can be used to direct tissue-specific expression of genes (e.g., transgenes) to which they are operatively linked. For example, the Fli1EP enhancer directs transcription to endothelial cells.

Polyadenylation signals, and their nucleotide sequences, are known in the art. Generally, a polyadenylation signal is present downstream, in the transcriptional sense, of the transgene. Polyadenylation signals that are active in eukaryotic cells include, but are not limited to, the SV40 polyadenylation signal, the bovine growth hormone (BGH) gene polyadenylation signal and the herpes simplex virus thymidine kinase gene polyadenylation signal. The polyadenylation signal directs 3' end cleavage of pre-mRNA, polyadenylation of the pre-mRNA at the cleavage site and termination of transcription downstream of the polyadenylation signal. A core sequence AAUAAA is generally present in the polyadenylation signal. See also Cole et al. (1985) Mol. Cell. Biol. 5:2104-2113.

In further embodiments, the vectors and transgene cassettes disclosed herein contain an insulator element, also known as a matrix attachment region (MAR) or scaffold attachment region (SAR). MAR and SAR sequences act, inter alia, to insulate the chromatin structure of adjacent sequences. Thus, in a stably transformed cell, in which heterologous sequences are chromosomally integrated, an insulator sequence can prevent repression of transcription of a transgene that has integrated into a region of the cellular genome having a repressive chromatin structure. Accordingly, inclusion of one or more insulator sequences in a vector can facilitate expression of a transgene from the vector in stably-transformed cells.

Exemplary insulator elements include those from the human interferon beta gene (IBM), the chicken (*G. gallus*) lysozyme gene 5' matrix attachment region (CLM), the human interferon alpha-2 gene (IAM), the mouse S4 MAR/SAR and the human X29 MAR/SAR. The insulator can be located at any location within the vector or the cassette. In certain embodiments, insulator elements are located within the transgene cassette upstream (in the transcriptional sense) of a promoter. In additional embodiments, insulator elements are present at both ends of a transgene.

In certain embodiments, the vectors also include, within an expression cassette (as defined above) a post-transcriptional regulatory element (PRE). In certain embodiments, the post-transcriptional regulatory element is a cis-acting element that promotes mRNA stability. In other embodiments, the post-transcriptional regulatory element is a cis-acting element that promotes transport of RNA from the nucleus to the cytoplasm. Exemplary PREs include the human hepatitis B virus PRE (HPRE) and the woodchuck hepatitis virus post-transcriptional regulatory element (WPRE). See, e.g., U.S. Pat. No. 6,136,597; Huang & Liang (1993) Mol. Cell. Biol. 13:7476-7486; Huang & Yen (1994) J. Virol. 68:3193-3199; Donello et al. (1996) J. Virol. 70:4345-4351; and Donello et al. (1998) J. Virology 72:5085-5092. Sub-elements of the HPRE (a element and ß element) and WPRE (a element, ß element and y element) have been identified. Accordingly, chimeric PREs containing mixtures of HPRE and WPRE sub-elements are also contemplated for use in the compositions disclosed herein.

Additional post-transcriptional regulatory elements include, but are not limited to, the 5'-untranslated region of the human Hsp70 gene, the SP163 sequence from the vascular endothelial growth factor (VEGF) gene, the tripartite leader sequence associated with adenovirus late mRNAs and the first intron of the human cytomegalovirus immediate early gene. See, for example, Mariati et al. (2010) Protein Expression and Purification 69:9-15.

A transgene can comprise an intron which, in certain instances, can increase production of mRNA from an integrated transgene. Exemplary introns that can be used include the human β-globin intron and the first intron of the human cytomegalovirus major immediate early (MIE) gene, also known as "intron A."

Vectors containing a transgene cassette can contain a replication origin that functions in prokaryotic cells. Replication origins that functions in prokaryotic cells are known in the art and include, but are not limited to, the oriC origin of *E. coli*; plasmid origins such as, for example, the pSC101 origin, the pBR322 origin (rep) and the pUC origin; and viral (i.e., bacteriophage) replication origins (e.g., the f1 replication origin). Methods for identifying prokaryotic replication origins are provided, for example, in Sernova & Gelfand (2008) Brief. Bioinformatics 9(5):376-391.

VI. Selection Markers

Selection markers, both positive and negative, are known in the art. An exemplary selection marker that functions in eukaryotic cells is the glutamine synthetase (GS) gene; selection is applied by culturing cells in medium lacking glutamine or medium containing methionine sulfoximine. Another exemplary selection marker that functions in eukaryotic cells is the gene encoding resistance to neomycin (neo); selection is applied by culturing cells in medium containing neomycin or G418. An exemplary gene encoding neomycin resistance is the TN5 Neo gene. Additional selection markers include sequences encoding dihydrofolate reductase (DHFR, imparts resistance to methotrexate), puromycin-N-acetyl transferase (provides resistance to puromycin), hygromycin kinase (provides resistance to hygromycin B), hygromycin phosphotransferase, aminoglycoside-3-phosphotransferase, ble, and genes encoding resistance to zeocin. Yet additional selection markers that function in eukaryotic cells are known in the art. Selective agents that can be used in the methods disclosed herein are known in the art and include, but are not limited to, G418, methotrexate, neomycin, geneticin, puromycin, bleomycin, Zeocin, blasticidin, hygromycin, methionine sulfoximine and L-glutamine. Any of the sequences encoding a selection marker as described above can be operatively linked to a promoter and/or a polyadenylation signal.

The vectors disclosed herein can also contain one or more selection markers that function in prokaryotic cells. Selection markers that function in prokaryotic cells are known in the art and include, for example, sequences that encode polypeptides conferring resistance to a selective agent such as, for example, ampicillin, kanamycin, chloramphenicol, or tetracycline. An example of a polypeptide conferring resistance to ampicillin (and other beta-lactam antibiotics) is the beta-lactamase (bla) enzyme. Kanamycin resistance can result from activity of the neomycin phosphotransferase gene; and chloramphenicol resistance is mediated by chloramphenicol acetyl transferase.

Negative selection markers that are active in prokaryotic cells include the ccdB gene, which encodes a DNA gyrase inhibitor.

The vectors disclosed herein can be any nucleic acid vector known in the art. Exemplary vectors include plasmids, cosmids, bacterial artificial chromosomes (BACs) and viral vectors.

VII. Transgenes

Any sequence, coding or noncoding, can serve as a transgene. For example, a transgene can encode a detectable moiety; e.g., a fluorescent protein, such as green fluorescent protein (GFP), enhanced green fluorescent protein (EGFP), red fluorescent protein, yellow fluorescent protein, tdTomato, luciferase and the like. A transgene can also encode an enzymatic activity (e.g., β-galactosidase, β-glucuronidase, luciferase and the like). A transgene can also be a therapeutic protein, such as globin, a coagulation factor, or a therapeutic antibody.

A transgene can encode, for example, a recombinant protein, a fusion protein, an antibody, a cytokine, a hormone, an enzyme or a clotting factor. Exemplary antibodies include monoclonal antibodies, single chain antibodies, bispecific antibodies, and antibody conjugates.

Exemplary transgenes include those encoding therapeutic proteins, e.g., hormones (such as, for example, growth hormone), cytokines (e.g., erythropoietin), antibodies, monoclonal antibodies (e.g., rituximab), antibody conjugates, fusion proteins (e.g., IgG-fusion proteins), interleukins, CD proteins, MHC proteins, enzymes and clotting factors.

Exemplary cytokines include, but are not limited to, erythropoietin, granulocyte colony-stimulating factor (G-CSF), filgrastim, and PEGfilgrastim.

Exemplary hormones include, but are not limited to, human growth hormone, luteinizing hormone (Luveris), and epoetin (Procrit).

Insertion of a transgene into a transgene vector is conducted using standard gateway cloning procedures, which results in conversion of the att sites present in the transgene vector into different att sites in the transgene-containing transgene vector. For example, in certain embodiments, attR sites (e.g., attR4 and attR3) present in a transgene vector are converted to attP sites (e.g., attP4 and attP3) in the process of inserting a transgene into the vector. Depending on the method of inserting transgene sequences, multiple att sites can be present in a transgene-containing transgene vector. For example, a transgene-containing transgene vector constructed by three-way gateway cloning will comprise four att sites.

VIII. Methods for Transgenesis

The compositions disclosed herein can be used for convenient, high-efficiency, non-viral insertion of a transgene into the genome of a cell, by contacting the cell with a combination comprising (1) a transgene-containing transgene cassette (2) and a nucleic acid comprising sequences encoding a polypeptide having retroviral integrase activity. A transgene-containing transgene cassette can be an isolated, double-stranded DNA molecule or it can be one of a plurality of DNA molecules generated by digestion of a transgene-containing transgene vector with a restriction enzyme. Contact can be by any method known in the art, including transfection, injection, electroporation, biolistic delivery, protoplast fusion, polyethylene glycol (PEG)-mediated methods, polyethyleneimine (PEI)-mediated methods, DEAE-dextran-mediated methods, calcium phosphate co-precipitation, and lipid-based particles (e.g., lipofection).

The methods and compositions described herein achieve high-efficiency transgene integration. In certain embodiments, at least 5% of cells exposed to a transgene undergo stable integration of the transgene into the genome (i.e. 5% efficiency of integration). In additional embodiments, the efficiency of integration is greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, or greater than 98%.

The cell can be any type of cell, including eukaryotic, prokaryotic or Archaeal. Exemplary eukaryotic cells include fungal cells (e.g., *Trichoderma* sp., *Pichia pastoris, Schizosaccharomyces pombae* and *Saccharomyces cerevisiae*), plant cells (e.g., *Arabidopsis* cells and tobacco BY2 cells), insect cells (e.g., Sf9, Sf21, and *Drosophila* S2 cells), vertebrate cells, teleost cells (e.g., *Danio* sp., e.g. *Danio rerio* or zebrafish), mammalian cells, primate cells and human cells. The transgene-containing transgene cassette can be an isolated and/or purified nucleic acid or can be part of a collection of nucleic acid molecules resulting from restriction enzyme digestion of a larger DNA molecule, e.g., a plasmid.

Cultured mammalian cell lines, useful for expression of recombinant polypeptides, include Chinese hamster ovary (CHO) cells, human embryonic kidney (HEK) cells, virally transformed HEK cells (e.g., HEK293 cells), NS0 cells, SP20 cells, CV-1 cells, baby hamster kidney (BHK) cells, 3T3 cells, Jurkat cells, HeLa cells, COS cells, PERC.6 cells, CAP® cells, CAP-T® cells (the latter two cell lines being commercially available from Cevec Pharmaceuticals, Cologne, Germany) and cancer cell lines such as A549 and PANC-1. A number of derivatives of CHO cells are also available such as, for example, CHO-DXB11, CHO-DG-44, CHO-K1 and CHO-S. Derivatives of any of the cells described herein obtained, for example, by mutagenesis, selection, gene knock-out, targeted integration (e.g., CRISPR/CAS9; zinc finger nucleases) or cloning, are also provided. Mammalian primary cells can also be used. Myeloma and hybridoma cells can also be used.

Nucleic acids comprising sequences encoding retroviral integrase activity, for use in these methods, are described elsewhere herein.

IX. Additional Embodiments

Each retrovirus encodes its own integrase protein, has unique LTR sequences and has a unique 5' terminal sequence of its double-stranded DNA pre-integration intermediate. Accordingly, the present disclosure provides additional transgene vectors and transgene cassettes containing dLTR sequences and 5'-terminal inverted repeat sequences of a retrovirus other than HIV-1 and methods in which such transgene vectors and transgene cassettes are used in conjunction with nucleic acids encoding an integrase protein from the virus used to provide the dLTR and inverted repeat sequences.

X. Targeted Integration

For certain applications, it is desirable to insert a transgene(s) at a specific location in the genome of the target cell or target organism. Targeted integration is achieved by taking advantage of elements of the CRISPR-Cas9 targeting system. The Cas9 protein is a RNA-guided DNA endonuclease that cleaves DNA sequences that are complementary to a guide RNA. Guide RNAs can be synthesized to be complementary to any DNA sequence of choice, and are thereby able to target the Cas9 endonuclease to any DNA sequence of choice (i.e., a genomic DNA sequence complementary to the targeting portion of the sequence of the guide RNA). Moreover, mutants of Cas9 that lack endonuclease activity (so-called "dead Cas9" or dCas9) can be fused to functional domains (such as transcriptional activation domains and transcriptional repression domains) to target the activity of these domains to particular genomic sequences (e.g., promoters).

dCas9 is a catalytically inactive mutant of the *Streptococcus pyogenes* cas9 protein that lacks endonuclease activity. The dCas9 protein remains capable of binding to DNA/RNA duplexes and therefore can be targeted to a particular chromosomal sequence using a guide RNA of appropriate nucleotide sequence.

The amino acid sequence of *S. pyogenes* dCas9 is:

(SEQ ID NO: 6)

```
MDKKYSIGLAIGTNSVGWAVITDEYKVPSKKFKVLGNTDRHSIK
KNLIGALLFDSGETAEATRLKRTARRRYTRRKNRICYLQEIFSNEMAKVD
DSFFHRLE
ESFLVEEDKKHERHPIFGNIVDEVAYHEKYPTIYHLRKKLVDSTDKADLR
LIYLALAH
MIKFRGHFLIEGDLNPDNSDVDKLFIQLVQTYNQLFEENPINASGVDAKA
ILSARLSK
SRRLENLIAQLPGEKKNGLFGNLIALSLGLTPNFKSNFDLAEDAKLQLSK
DTYDDDLD
NLLAQIGDQYADLFLAAKNLSDAILLSDILRVNTEITKAPLSASMIKRYD
EHHQDLTL
LKALVRQQLPEKYKEIFFDQSKNGYAGYIDGGASQEEFYKFIKPILEKMD
GTEELLVK
LNREDLLRKQRTFDNGSIPHQIHLGELHAILRRQEDFYPFLKDNREKIEK
ILTFRIPY
YVGPLARGNSRFAWMTRKSEETITPWNFEEVVDKGASAQSFIERMTNFDK
NLPNEKVL
PKHSLLYEYFTVYNELTKVKYVTEGMRKPAFLSGEQKKAIVDLLFKTNRK
VTVKQLKE
DYFKKIECFDSVEISGVEDRFNASLGTYHDLLKIIKDKDFLDNEENEDIL
EDIVLTLT
```

-continued

```
LFEDREMIEERLKTYAHLFDDKVMKQLKRRRYTGWGRLSRKLINGIRDKQ
SGKTILDF
LKSDGFANRNFMQLIHDDSLTFKEDIQKAQVSGQGDSLHEHIANLAGSPA
IKKGILQT
VKVVDELVKVMGRHKPENIVIEMARENQTTQKGQKNSRERMKRIEEGIKE
LGSQILKE
HPVENTQLQNEKLYLYYLQNGRDMYVDQELDINRLSDYDVDAIVPQSFLK
DDSIDNKV
LTRSDKNRGKSDNVPSEEVVKKMKNYWRQLLNAKLITQRKFDNLTKAERG
GLSELDKA
GFIKRQLVETRQITKHVAQILDSRMNTKYDENDKLIREVKVITLKSKLVS
DFRKDFQF
YKVREINNYHHAHDAYLNAVVGTALIKKYPKLESEFVYGDYKVYDVRKMI
AKSEQEIG
KATAKYFFYSNIMNFFKTEITLANGEIRKRPLIETNGETGEIVWDKGRDF
ATVRKVLS
MPQVNIVKKTEVQTGGFSKESILPKRNSDKLIARKKDWDPKKYGGFDSPT
VAYSVLVV
AKVEKGKSKKLKSVKELLGITIMERSSFEKNPIDFLEAKGYKEVKKDLII
KLPKYSLF
ELENGRKRMLASAGELQKGNELALPSKYVNFLYLASHYEKLKGSPEDNEQ
KQLFVEQH
KHYLDEIIEQISEFSKRVILADANLDKVLSAYNKHRDKPIREQAENIIHL
FTLTNLGA
PAAFKYFDTTIDRKRYTSTKEVLDATLIHQSITGLYETRIDLSQLGGD
```

Lens epithelium-derived growth factor (LEGDF/p75) also known as psip1a, PC4 or SFRS1-interacting protein, is a host factor that participates in integration of the HIV genome into a host chromosome. The C-terminal portion of this protein contains an integrase-binding domain, which interacts with lentiviral integrase proteins and with other cellular proteins. The psip1a protein also binds to chromosomal DNA, thereby tethering integrase to chromosomal DNA at the integration site.

The amino acid sequence of zebrafish psip1a is:

(SEQ ID NO: 7)

```
MAQDFKAGDLIFAKMKGYPHWPARIDEIPDGAVKPSNIKFPIFF
FGTHETAFLGPKDIFPYLTNKDKYGKPNKRKGFNEGLWEIENNPKVELNG
HKVKKVGE
VSIKDLSSNEEGDDEKRTKSAQIAHSEGLEDEVDIEKEDGGDMDVSDQRL
VKDEDLSQ
KDSTNVTAKAKRGRKRKSDAEQDSDTENSSPTAGGSGLDFLSTGTSIMLL
KRRGRKSK
```

-continued

TEKSIILQQQASKELPRSGKDGKRDERKGDKRKESTLQKLHGEIKTSLKI

GNLDVRKC

VHALDELSSLHVTTQHLQRHSELIATLKKICRFKSSQDVMDKAIMLYNKF

KSMFLMGE

GESVLSQVLNKSLTEQKLFEEAKRGVLKNTEQTKEQKDTKILNEDFNSEE

DAETEKDK

LGGNILSMVKNNMTDPAEESV

For targeted integration using the transgene vectors disclosed herein, the transgene vector and integrase-encoding nucleic acid are supplemented with a nucleic acid (e.g., DNA, RNA) encoding a fusion between dCas9 and the psip1a (LEDGF) protein, in conjunction with a guide RNA whose targeting region is complementary to the genomic sequence at which integration is desired. The guide RNA targets the dCas9 portion of the fusion protein to the target genomic sequence, while the psip1a portion of the fusion protein interacts with integrase to tether the integrase/transgene cassette pre-integration complex to the target genomic sequence, thereby facilitating integration at the target genomic sequence. A schematic diagram illustrating this method is shown in FIG. 22.

Accordingly, in certain embodiments for targeted integration of a transgene, the following constituents are introduced into the target cell:

(1) single guide RNA (sgRNA) with a sequence complementary to the target genomic sequence and a hairpin sequence that binds dCas9, (2) a dCas9-psip1a fusion protein, or mRNA encoding a dCas9-psip1a fusion protein, (3) mRNA encoding an integrase, and (4) a transgene cassette.

In additional embodiments, sequences encoding the dCas9-psip1a fusion protein are present on a DNA molecule (e.g., a plasmid) and are under the transcriptional and translational control of elements that are active in the target cell.

In additional embodiments, sequences encoding the integrase protein are present on a DNA molecule (e.g., a plasmid) and are under the transcriptional and translational control of elements that are active in the target cell.

The foregoing methods for targeted integration rely on binding of the psip1a portion of the psip1a-dCas9 fusion protein to integrase molecules that are present at both ends of the transgene cassette in a preintegration complex. However, endogenous psip1a (already present in the cell) can compete with binding of the psip1a-dCas9 fusion protein to the integrase proteins present in the preintegration complex. Accordingly, in certain embodiments, the psip1a-dCas9 fusion protein is overexpressed in target cells, for example, by injecting RNA encoding the psip1a-dCas9 fusion protein at a molar excess to integrase RNA, by injecting a quantity of RNA encoding the psip1a-dCas9 fusion protein that will produce a molar excess of psip1a-dCas9 fusion protein to endogenous psip1a, or by introducing an expression vector containing sequences encoding the psip1a-dCas9 fusion protein (instead of RNA encoding the psip1a-dCas9 fusion protein) in which the sequences encoding the psip1a-dCas9 fusion protein are under the transcriptional control of sequences that express, or can be induced to express, the psip1A-dCas9-encoding sequence at high levels. In additional embodiments, inhibition of expression of endogenous psip1a, for example, by blocking splicing of psip1a pre-mRNA with morpholino compounds, can also be used to enhance the efficiency of targeted integration.

Translational control elements (e.g., Kozak sequences or the like) which are active at high levels in the host cell can also be included in vectors for overexpression of the psip1a-dCas9 fusion protein.

EXAMPLES

Example 1: Construction of Transgene Vectors

Transgene plasmids (pLTR vectors) were constructed by modifying the Gateway cloning destination vector pminiTol2 R4R3 (Addgene #40970, see also Kwan et al. (2007) Devel. Dynamics 236:3088-3099), which contains an attR4/attR3 gateway cassette flanked by Tol2 transposon sequences.

Briefly, the upstream and downstream miniTol2 sequences were replaced by two truncated HIV-1 LTR sequences. The upstream miniTol2 sequence was replaced with sequences containing the R and U5 sequences of the HIV-1 LTR (5'-dLTR; template from Addgene #14883). The downstream miniTol2 sequence was replaced with sequences containing dU3, R and U5 sequences of the HIV-1 LTR (3'-dLTR; template from Addgene #19319).

For sequence replacement, DNA molecules were constructed that contained the replacement sequence (5' dLTR or 3' dLTR) with the sequence 5'-ACTG-3' appended to the 5' end of the replacement sequence, and terminating in a recognition site for a blunt end-generating restriction enzyme (e.g., ScaI, PmeI or BstZ17I). Replacement DNA molecules were amplified by PCR, using Addgene 14883 and 19319 as templates, using Platinum™ Taq DNA Polymerase High Fidelity (Invitrogen). The amplification products were then inserted into the pminiTol2R4R3 vector. 5' dLTR-containing PCR products were ligated into NdeI/XhoI-digested pminiTol2R4R3. 3' dLTR-containing PCR products were ligated into ApaI/ScaII-digested pminiTol2R4R3.

A schematic diagram of the vector is shown in FIG. 11. A more detailed map of the transgene cassette portion of the vector is provided in FIG. 12. The vector shown in FIG. 11 has recognition sites for the blunt end-generating restriction enzyme BstZ17I external to the truncated LTR (i.e., 5' dLTR and 3' dLTR) sequences. Two additional vectors have been constructed: one having PmeI sites at these locations and the other having ScaI sites at these locations.

Transgenes, and optionally regulatory sequences, are inserted into the transgene vector using standard gateway cloning methods. One-way, two-way, or three-way insertions can be used, depending on the nature of the transgene and associated (e.g., regulatory) sequences. See, e.g., Hartley et al., supra for additional details of methods for one-way, two-way and three-way insertions.

Plasmids were amplified in One Shot® TOP10 *E. coli* cells (Invitrogen, Carlsbad, CA) and purified using a PureLink® Quick Plasmid Miniprep Kit (Invitrogen) for subsequent microinjection, transfection, or production of mRNA by in vitro transcription.

Example 2: Construction of Integrase Vectors

The pCS2-integrase and pCS2-integrase-2A-tdTomato overexpression vectors were constructed using standard gateway cloning protocols with pCSDest2 (Addgene #22424), p3E-2a-tdTomato (Addgene #67707) and pME-integrase. pME-integrase was generated by conducting a standard gateway BP reaction using wild-type HIV-1 integrase in pET15b (Addgene #61668) as a template for PCR. A Kozak sequence was present in the vector for regulation of translation of the integrase sequences. All constructs were verified by DNA sequencing.

The p5E-CMV/SP6 plasmid (a 5' entry gateway clone containing the CMV promoter) was obtained from Dr. Nathan Lawson. p5E-cmlc2 was obtained from a zebrafish Tol2 kit generated by Dr. Chien Chi-Bin. Kwan, K. M. et al. (2007) Dev Dyn 236:3088-3099. cmlc2 is a promoter that specifies transcription in the heart.

Example 3: Stable Integration of a Transgene in Zebrafish

This example shows that co-injection of an EGFP-expressing transgene cassette and integrase-encoding mRNA, into zebrafish embryos, results in high-efficiency, stable transfection.

Adult zebrafish were housed in an Aquaneering (San Diego, CA) zebrafish housing system at 28° C. on a 14-hours light and 10-hours dark cycle. Single pair crossing were used to generate fertilized embryos for microinjection to test for stable genomic integration of transgenes. After analysis, selected embryos were incubated in the egg water at 28° C. for up to 6 days post-fertilization (dpf) before being raised in the main system.

A transgene cassette comprising sequences encoding enhanced green fluorescent protein (EGFP) under the control of a CMV promoter (pLTR-CMV-EGFP) was constructed by inserting a CMV promoter, EGFP cDNA and a BGH polyadenylation signal into the vector described in Example 1 using a 3-way (i.e., 5' entry (CMV promoter), middle entry (EGFP) and 3' entry (polyadenylation signal)) gateway insertion. See FIG. 13.

Integrase-encoding mRNA was generated using a mMESSAGE mMACHINE® SP6 Transcription Kit (Invitrogen) with pCS2-Integrase, linearized with NotI, as a template. RNA was purified by phenol/chloroform extraction and ethanol precipitation.

One-cell zebrafish embryos were co-injected with the EGFP transgene cassette and the integrase mRNA, as shown schematically in FIG. 13. Microinjection was performed as described. Kawakami, K. (2007) Genome Biol 8 Suppl 1:S7; Thermes, V. et al. (2002) Mech Dev 118:91-98. Embryos at the one-cell stage were injected with a high dose of 25 ng/ul each of DNA and RNA, or with a low dose of 12.5 ng/ul each of DNA and RNA) in a volume of 0.5 nl per embryo.

The injected embryos were analyzed for the expression of the EGFP transgene at 6 days post-fertilization (DPF). For fluorescence analysis, live embryos were placed in egg water containing 1× tricaine. Fluorescence images were acquired using a Leica M165 FC stereo microscope. Injected embryos were categorized in five different groups (Group 0 through Group 4) based on the degree of GFP expression, with Group 0 showing no EGFP fluorescence and Group 4 showing the highest amount of EGFP fluorescence. Groups 2-4 represent successful genome integration with strong transgene expression and a high potential for germ line transmission in F1 fish. Group 0 and Group 1 represent fish in which no integration occurred (Group 0) or a very small amount of integration occurred (Group 1).

A comparison of integration levels using two different doses of injected nucleic acid (a high dose of 25 ng/ul each of mRNA and DNA or a low dose of 12.5 ng/ul each) was performed, and the results were quantified. As shown in FIG. 14, stable integration (i.e., generation of fish in groups 2, 3 and 4) was obtained in 55% of embryos injected at the high dose; and in 38% of embryos injected at the low dose. When these results are compared with those obtained from embryos in control experiments injected with only the transgene cassette (FIG. 14, first and third pairs of bars), it is clear that the HIV-1 integrase greatly facilitates the integration rate. Accordingly, the methods disclosed herein are capable of achieving stable transgenesis in zebrafish with very high efficiency.

Example 4: Comparison with Other Methods of Zebrafish Transgenesis

Existing methods for construction of transgenic zebrafish (and other organisms) without using viral vectors include (1) Tol2-mediated transgenesis and (2) meganuclease (e.g., I-SceI)-mediated transgenesis. Accordingly, the methods described herein were compared to these two methods of performing transgenesis in zebrafish. FIG. 15 shows that Tol2-mediated integration resulted in 62% stable transgenesis (i.e., 62% of fish that developed from treated embryos fell into Groups 2, 3 and 4); and FIG. 16 shows that I-SceI-mediated integration results in 20% stable transgenesis (i.e., 20% of fish that developed from treated embryos fell into Groups 2, 3 and 4) These results were consistent with those obtained previously Kawakami et al. (2007) Genome Biol. 8:Suppl 1: S7; Thermes et al. (2002) Mech. Devel. 118:91-98. Thus, the efficiency of transgenesis obtained with the methods disclosed herein (up to 55%) is much higher than that obtained using the I-SceI method, and comparable to that obtained using Tol2-mediated transposon sequences. Moreover, the methods disclosed herein do not suffer from the disadvantage, encountered with Tol2-mediated transgenesis, of mobilization of the integrated transgene in the presence of the Tol2 transposon. These results indicate that the efficiency of transgenesis obtained with the methods disclosed herein is better than or similar to current methods.

Example 5: Tissue-Specific Transgene Expression

To test for the ability to direct tissue-specific expression of a transgene introduced by the methods disclosed herein, a transgene cassette containing sequences encoding EGFP under the control of Flilep enhancer (which directs transcription in endothelial cells) was constructed and denoted pLTR-Fli1ep:EGFP-pA. The p5E-fli1ep plasmid, containing the Flilep enhancer, was obtained from Dr. Nathan Lawson.

As in Example 3, fish that developed from injected embryos were grouped into five categories based on the degree of EGFP expression (negative expression: Group 0, low expression: Group 1 and increasing degrees of positive expression: Groups 2, 3 and 4). Fluorescent images of zebrafish that developed from embryos that had been injected with integrase mRNA and a transgene cassette containing sequences encoding enhanced green fluorescent protein under the transcriptional control of the endothelial-specific Flilep enhancer showed that; in Groups 2, 3 and 4; EGFP expression was primarily restricted to the vasculature. In addition, the levels of stable transgene integration were 57% in fish injected with 25 ng/ul and 27% in fish injected with 12.5 ng/ul (FIG. 17) similar to the levels observed in Example 3 using an enhancerless construct. These results demonstrate that the methods disclosed herein provide the ability for regional, spatial and tissue-specific control of stable transgene expression.

In additional experiments using the catalytically-deficient integrase mutants D116A and E152A, a much lower integration efficiency (approximately 10%) was obtained; and all integrants were in Group 2 (i.e., low level of integration). These results indicate that, although a certain amount of integration can occur in the absence of integrase activity, high levels of integration depend on functional integrase.

Example 6: Stable Transgenesis in Cultured Cells

This example shows that high levels of stable integration are obtained following co-transfection, into cultured human cells, of (1) a transgene cassette containing EGFP-encoding sequences under the transcriptional control of a CMV promoter and a (2) plasmid encoding HIV-1 integrase under the transcriptional control of a CMV promoter (pCS2-Integrase-2A-tdTomato). The transgene cassette was obtained by cleavage of the pLTR-CMV-EGFP plasmid (described in Example 3) with BstZ17I. The design of the experiment is shown schematically in FIG. 18.

Two human epithelial cancer lines, A549 and PANC-1, were used in these experiments. Human lung cancer cell line A549 was acquired from ATCC (#CCL-185) and maintained in F12 medium supplied with 10% fetal bovine serum at 37° C. in a humidified atmosphere of 5% $CO_2$/95% air in the presence of antibiotics. The human pancreatic cancer line PANC-1 was obtained from Sigma (#87092802) and maintained in DMEM with 10% fetal bovine serum at 37° C. in a humidified atmosphere of 5% $CO_2$/95% air in the presence of antibiotics.

Transfection was conducted using Lipofectamine® 3000 (Invitrogen, Carlsbad, CA) according to the manufacturer's instructions. Briefly, one day before transfection, cells were seeded at a density of $2\times10^5$ cells/well in a 12-well plate. After 24 hours, the cells were rinsed with phosphate-buffered saline (PBS). Each group was transfected with a mixture of 1 μg BstZ17I-digested pLTR-CMV-EGFP and 1 μg of pCS2-Integrase-2A-tdTomato, using Lipofectamine®-p3000 mixture in Opti-MEM for 4 hours, after which an equal volume of complete medium was added. In control experiments, cells were transfected with the EGFP transgene cassette and a plasmid that lacked sequences encoding integrase (pSC2-2ATomato-pA).

One day after transfection, the cells were subcultured and analyzed by flow cytometry to determine the number of cells that received both DNA molecules. Single cell suspensions of the samples were prepared by trypsinization, and the fluorescence intensity of each sample was evaluated on a LSR II flow cytometer (BD Biosciences, San Jose, CA). For each analysis, at least 10,000 events were recorded. Green (GFP) and Red (tdTomato) fluorescent signal were used as indicators for successful co-transfection of transgene and integrase plasmid, respectively, and the percentages of double positive events (both red and green fluorescence) were calculated using FACSDiva software (BD Biosciences). Untransfected cells served as a negative control.

Seven days after transfection (approximately three passages), at which time only stable transfectants persist, the degree of integration was determined by fluorescence imaging using a Leica M165 FC stereomicroscope. At least four images were taken in random locations of the dish for each experimental group. Representative images are shown in FIG. 19, with green fluorescence (shown as white in the figure) indicating stable integration of the EGFP transgene cassette.

To quantify the percentage of the cells with positive GFP expression, all images were analyzed and processed consistently using Image J by adjusting the threshold and counting the positive pixels.

Quantified results were averaged and normalized to the transfection efficiency. FIG. 20 shows the results of the quantitative analysis, which indicate that 42% of A549 cells, and 41% of PANC-1 cells, that received both the EGFP transgene cassette and the integrase plasmid expressed EGFP, compared to 12% of A5459 cells, and 13% of PANC-1 cells, that received the transgene cassette and a plasmid that did not express integrase (pCS2-2Atomato-pA).

Example 7: Effect of End Structure on Integration Efficiency

As noted elsewhere herein, retroviral integrases require a linear double-stranded DNA molecule, containing the terminal inverted repeat sequence 5'-ACTG-3', as a substrate for end processing and strand transfer (i.e., integration). In this example, the effect, on integration efficiency, of the location of the 5'-ACTG-3' sequence (the IR sequence), with respect to the termini of the transgene cassette, was tested. To this end, four versions of a transgene vector containing sequences encoding the red fluorescent protein tdTomato, under the transcriptional control of the cardiac-specific cMLC2 promoter and the BGH polyadenylation site, were generated. Each had a different end structure external to the IR sequences. Cleavage of the transgene vector with ScaI generated perfect 5'-ACTG-3' blunt-ends on the resulting transgene DNA cassette; while cleavage with BstZ17I generated a transgene cassette with one additional terminal nucleotide exterior to the IR sequence (5'-TACTG-3') and cleavage with PmeI generated a transgene cassette with two extra nucleotides exterior to the IR sequence (5'-AAACTG-3'). Double digestion with MluI and ApaI generated ends with 4-nucleotide overhangs exterior to the IR sequence.

One-cell embryos were injected with 12.5 ng/μl of integrase-encoding mRNA and 12.5 ng/μl of the of each of four different tdTomato-encoding transgene cassettes. Fish developing from injected embryos were analyzed for red fluorescence at 6 days post-fertilization dpf) and categorized into three groups: Group 0 (no fluorescence); Group 1 (partial fluorescence in heart) and Group 2 (full fluorescence in heart). The percentage of embryos in Groups 1 and 2 (i.e., percentage of embryos in which transgene was stably integrated) is shown in FIG. 21. As can be seen, there were no significant differences, in integration efficiency among transgene cassettes terminating in ScaI ends, BstZ17I ends and PmeI ends. Thus, the presence of one or two extra nucleotide, external to the IR sequence, does not affect integration efficiency. In contrast, if the transgene cassette possessed ends having 4-nucleotide overhangs (generated by double digestion with MluI (5'-CGCG overhang) and ApaI (3'-CCGG overhang) external to the 5'-ACTG-3' IR sequence, integrase-dependent integration was totally abolished (FIG. 21), suggesting that the integrase cannot perform 3' processing or strand transfer on such a substrate. These results indicate that the terminal sequence and structure of the transgene cassette is important for high-efficiency integration, but that a certain amount of variability in the location of the IR sequence is tolerated.

In additional experiments, the contribution of the LTR sequences that are present in the transgene cassette was investigated. The following results were obtained:

(a) transgenes whose expression was directed by an endothelium-specific enhancer, flanked on both ends with a 21-nucleotide U3 sequence that included a 5'-ACTG-3' blunt-ended sequence (i.e., no dLTR sequences), integrated efficiently in the presence of integrase; however, integration was non-specific;

(b) transgenes with a single downstream 3'-dLTR (i.e., no upstream 5' dLTR) integrated with higher efficiency than transgenes flanked by both a 5'-dLTR and a 3'-dLTR;

(c) transgenes with a single upstream 5'-dLTR (i.e., no downstream 3' dLTR) integrated with lower efficiency than transgenes flanked by both a 5'-dLTR and a 3'-dLTR.

Statistical Analysis

All assays were carried out in triplicate or more. Data was expressed as a mean or stacked mean with standard deviation (SD). The Student's t-test was used to compare the mean between groups to determine statistical significance; with a p value <0.05 considered statistically significant.

Example 8: Vectors Encoding dCas9-psip1a Fusions

A vector encoding a fusion between LEGDF (psip1A) and dCas9 was constructed as follows. Sequences encoding zebrafish psip1a (zpsip1a) cDNA were cloned from zebrafish DNA and inserted by gateway cloning into the pME entry vector. Cas9 sequences were obtained as a KpnI/NheI fragment produced by double digestion of the dCas9 plasmid #100091 (Addgene, Watertown, MA). The psip1a sequence, the cas9 sequence, linearized pCS expression vector (Miyoshi et al. (1998) J. Virol. 72:8150-8157), a nuclear localization sequence (NLS) and sequences encoding $(GGS)_5$ (SEQ ID NO:17) linkers were joined by Gibson assembly (Gibson et al. (2009) Nature Methods 6:343-345) to generate two fusions: one in which dCas9 sequences are upstream of psip1a sequences; the other in which dCas9 sequences are downstream of psip1a sequences. Schematically, the two fusions have the following structures:

pCS-NLS-dCas9-$(GGS)_5$-zpsip1a (Cas-psip vector)

pCS-zpsip1a-$(GGS)_5$-dCas9-NLS (psip-Cas vector)

The nucleotide sequence of the pCS-NLS-dCas9-$(GGS)_5$-zpsip1a vector is:

```
                                                         (SEQ ID NO: 8)
   1 CGCCATTCTG CCTGGGGACG TCGGAGCAAG CTTGATTTAG GTGACACTAT AGAATACAAG

  61 CTACTTGTTC TTTTTGCAGG ATccgccacc ATGcccaaga agaagaggaa ggtgggtggt

 121 tccggaggaa gccggccaat ggacaagaag tactccattg ggctcgctat cggcacaaac

 181 agcgtcggct gggccgtcat tacggacgag tacaaggtgc cgagcaaaaa attcaaagtt

 241 ctgggcaata ccgatcgcca cagcataaag aagaacctca ttggcgccct cctgttcgac

 301 tccggggaga cggccgaagc cacgcggctc aaaagaacag cacggcgcag atatacccgc

 361 agaaagaatc ggatctgcta cctgcaggag atctttagta atgagatggc taaggtggat

 421 gactctttct tccataggct ggaggagtcc tttttggtgg aggaggataa aaagcacgag

 481 cgccacccaa tctttggcaa tatcgtggac gaggtggcgt accatgaaaa gtacccaacc

 541 atatatcatc tgaggaagaa gcttgtagac agtactgata aggctgactt gcggttgatc

 601 tatctcgcgc tggcgcatat gatcaaattt cggggacact tcctcatcga gggggacctg

 661 aacccagaca acagcgatgt cgacaaactc tttatccaac tggttcagac ttacaatcag

 721 cttttcgaag agaacccgat caacgcatcc ggagttgacg ccaaagcaat cctgagcgct

 781 aggctgtcca aatcccggcg gctcgaaaac ctcatcgcac agctccctgg ggagaagaag

 841 aacggcctgt ttggtaatct tatcgccctg tcactcgggc tgacccccaa ctttaaatct

 901 aacttcgacc tggccgaaga tgccaagctt caactgagca aagacaccta cgatgatgat

 961 ctcgacaatc tgctggccca gatcggcgac cagtacgcag acctttttt ggcggcaaag

1021 aacctgtcag acgccattct gctgagtgat attctgcgag tgaacacgga gatcaccaaa

1081 gctccgctga gcgctagtat gatcaagcgc tatgatgagc accaccaaga cttgactttg

1141 ctgaaggccc ttgtcagaca gcaactgcct gagaagtaca aggaaatttt cttcgatcag

1201 tctaaaaatg gctacgccgg atacattgac ggcggagcaa gccaggagga attttacaaa

1261 tttattaagc ccatcttgga aaaaatggac ggcaccgagg agctgctggt aaagcttaac

1321 agagaagatc tgttgcgcaa acagcgcact ttcgacaatg gaagcatccc ccaccagatt

1381 cacctgggcg aactgcacgc tatcctcagg cggcaagagg atttctaccc ctttttgaaa

1441 gataacaggg aaaagattga gaaaatcctc acatttcgga taccctacta tgtaggcccc

1501 ctcgcccggg gaaattccag attcgcgtgg atgactcgca aatcagaaga gaccatcact
```

-continued 1561 ccctggaact tcgaggaagt cgtggataag gggcctctg cccagtcctt catcgaaagg 1621 atgactaact ttgataaaaa tctgcctaac gaaaaggtgc ttcctaaaca ctctctgctg 1681 tacgagtact tcacagttta taacgagctc accaaggtca aatacgtcac agaagggatg 1741 agaaagccag cattcctgtc tggagagcag aagaaagcta tcgtggacct cctcttcaag 1801 acgaaccgga aagttaccgt gaaacagctc aaagaagact atttcaaaaa gattgaatgt 1861 ttcgactctg ttgaaatcag cggagtggag gatcgcttca acgcatccct gggaacgtat 1921 cacgatctcc tgaaaatcat taaagacaag gacttcctgg acaatgagga gaacgaggac 1981 attcttgagg acattgtcct cacccttacg ttgtttgaag atagggagat gattgaagaa 2041 cgcttgaaaa cttacgctca tctcttcgac gacaaagtca tgaaacagct caagaggcgc 2101 cgatatacag gatgggggcg gctgtcaaga aaactgatca atgggatccg agacaagcag 2161 agtggaaaga caatcctgga ttttcttaag tccgatggat ttgccaacag gaacttcatg 2221 cagttgatcc atgatgactc tctcaccttt aaggaggaca tccagaaagc acaagtttct 2281 ggccaggggg acagtcttca cgagcacatc gctaatcttg caggtagccc agctatcaaa 2341 aagggaatac tgcagaccgt taaggtcgtg gatgaactcg tcaaagtaat gggaaggcat 2401 aagcccgaga atatcgttat cgagatggcc cgagagaacc aaactaccca gaagggacag 2461 aagaacagta gggaaaggat gaagaggatt gaagagggta taaaagaact ggggtcccaa 2521 atccttaagg aacacccagt tgaaaacacc cagcttcaga atgagaagct ctacctgtac 2581 tacctgcaga acggcaggga catgtacgtg gatcaggaac tggacatcaa tcggctctcc 2641 gactacgacg tggatgctat cgtgccccag tcttttctca aagatgattc tattgataat 2701 aaagtgttga caagatccga taaaaataga gggaagagtg ataacgtccc ctcagaagaa 2761 gttgtcaaga aaatgaaaaa ttattggcgg cagctgctga acgccaaact gatcacacaa 2821 cggaagttcg ataatctgac taaggctgaa cgaggtggcc tgtctgagtt ggataaagcc 2881 ggcttcatca aaaggcagct tgttgagaca cgccagatca ccaagcacgt ggcccaaatt 2941 ctcgattcac gcatgaacac caagtacgat gaaaatgaca aactgattcg agaggtgaaa 3001 gttattactc tgaagtctaa gctggtctca gatttcagaa aggactttca gttttataag 3061 gtgagagaga tcaacaatta ccaccatgcg catgatgcct acctgaatgc agtggtaggc 3121 actgcactta tcaaaaaata tcccaagctt gaatctgaat ttgtttacgg agactataaa 3181 gtgtacgatg ttaggaaaat gatcgcaaag tctgagcagg aaataggcaa ggccaccgct 3241 aagtacttct tttacagcaa tattatgaat tttttcaaga ccgagattac actggccaat 3301 ggagagattc ggaagcgacc acttatcgaa acaaacggag aaacaggaga aatcgtgtgg 3361 gacaagggta gggatttcgc gacagtccgg aaggtcctgt ccatgccgca ggtgaacatc 3421 gttaaaaaga ccgaagtaca gaccggaggc ttctccaagg aaagtatcct cccgaaaagg 3481 aacagcgaca agctgatcgc acgcaaaaaa gattgggacc ccaagaaata cggcggattc 3541 gattctccta cagtcgctta cagtgtactg gttgtggcca aagtggagaa agggaagtct 3601 aaaaaactca aaagcgtcaa ggaactgctg ggcatcacaa tcatggagcg atcaagcttc 3661 gaaaaaaacc ccatcgactt tctcgaggcg aaaggatata aagaggtcaa aaaagacctc 3721 atcattaagc ttcccaagta ctctctcttt gagcttgaaa acggccggaa acgaatgctc 3781 gctagtgcgg gcgagctgca gaaaggtaac gagctggcac tgccctctaa atacgttaat 3841 ttcttgtatc tggccagcca ctatgaaaag ctcaaagggt ctcccgaaga taatgagcag 3901 aagcagctgt tcgtggaaca acacaaacac taccttgatg agatcatcga gcaaataagc -continued

```
3961 gaattctcca aaagagtgat cctcgccgac gctaacctcg ataaggtgct ttctgcttac
4021 aataagcaca gggataagcc catcagggag caggcagaaa acattatcca cttgtttact
4081 ctgaccaact tgggcgcgcc tgcagccttc aagtacttcg acaccaccat agacagaaag
4141 cggtacacct ctacaaagga ggtcctggac gccacactga ttcatcagtc aattacgggg
4201 ctctatgaaa caagaatcga cctctctcag ctcggtggag acggtggtag tggaggttca
4261 ggaggatccg gggggagcgg agggagcgct agcatggctc aggatttcaa agctggtgat
4321 ctgatttttg ctaagatgaa gggttatcca cactggcctg caaggattga tgagattcca
4381 gatggtgctg tcaaaccatc aaatataaaa tttcccatct tctttttgg cactcatgaa
4441 acagcattcc tgggtcctaa agacatattc ccctatttga ccaataaaga caaatatggc
4501 aaacctaaca aaaggaaggg tttcaatgaa ggcttgtggg aaattgaaaa caatcctaaa
4561 gtggagctta atggacacaa ggtaaaaaag gttggagaag tttcaattaa agatttgagc
4621 agcaatgaag agggagatga tgagaagagg acaaagtcag ctcaaattgc tcacagtgag
4681 gggctggagg acgaggtgga cattgagaag gaagatggtg gtgacatgga cgtttctgat
4741 cagagacttg ttaaagatga agacctatca cagaaagatt cgacaaatgt cactgccaaa
4801 gctaaaagag gaaggaagag aaagagtgat gctgaacaag actctgatac agaaaattca
4861 agcccaactg caggcggttc cggtttagat ttcctatcaa caggtacatc aattatgtta
4921 ctgaagcgca gaggaaggaa atctaaaaca gagaagtcaa taatactaca acaacaggct
4981 tcaaaggaat taccaaggtc aggtaaagat ggaaagagag atgaaagaaa aggtgacaaa
5041 agaaaggagt ccacactgca gaagttgcac ggggagatta agacatcatt gaagattggt
5101 aatttagatg taaggaaatg tgtacatgca ttggatgagt taagctctct acatgttacc
5161 actcaacatc ttcagagaca tagtgaactc atagcaactc tgaaaaagat ctgcagattc
5221 aaatccagcc aggatgtgat ggacaaagct attatgctat ataataagtt taaaagtatg
5281 tttttaatgg gagaaggaga atcagtgcta agtcaggtgc tcaataaaag tctgactgaa
5341 cagaaactat ttgaagaagc caagagggga gtcctaaaaa acacagaaca aactaaagag
5401 cagaaagata ccaagatttt gaatgaagac ttcaactccg aagaggacgc tgagacagag
5461 aaggacaaat taggaggaaa catcttatct atggtgaaaa acaacatgac tgatcctgca
5521 gaagagtctg tctgacTCGA GCCTCTAGAA CTATAGTGAG TCGTATTACG TAGATCCAGA
5581 CATGATAAGA TACATTGATG AGTTTGGACA AACCACAACT AGAATGCAGT GAAAAAAATG
5641 CTTTATTTGT GAAATTTGTG ATGCTATTGC TTTATTTGTA ACCATTATAA GCTGCAATAA
5701 ACAAGTTAAC AACAACAATT GCATTCATTT TATGTTTCAG GTTCAGGGGG AGGTGTGGGA
5761 GGTTTTTTAA TTCGCGGCCG CGGCGCCAAT GCATTGGGCC CGGTACCCAG CTTTTGTTCC
5821 CTTTAGTGAG GGTTAATTGC GCGCTTGGCG TAATCATGGT CATAGCTGTT TCCTGTGTGA
5881 AATTGTTATC CGCTCACAAT TCCACACAAC ATACGAGCCG GAAGCATAAA GTGTAAAGCC
5941 TGGGGTGCCT AATGAGTGAG CTAACTCACA TTAATTGCGT TGCGCTCACT GCCCGCTTTC
6001 CAGTCGGGAA ACCTGTCGTG CCAGCTGCAT TAATGAATCG GCCAACGCGC GGGGAGAGGC
6061 GGTTTGCGTA TTGGGCGCTC TTCCGCTTCC TCGCTCACTG ACTCGCTGCG CTCGGTCGTT
6121 CGGCTGCGGC GAGCGGTATC AGCTCACTCA AAGGCGGTAA TACGGTTATC CACAGAATCA
6181 GGGGATAACG CAGGAAAGAA CATGTGAGCA AAAGGCCAGC AAAAGGCCAG GAACCGTAAA
6241 AAGGCCGCGT TGCTGGCGTT TTTCCATAGG CTCCGCCCCC CTGACGAGCA TCACAAAAAT
6301 CGACGCTCAA GTCAGAGGTG GCGAAACCCG ACAGGACTAT AAAGATACCA GGCGTTTCCC
6361 CCTGGAAGCT CCCTCGTGCG CTCTCCTGTT CCGACCCTGC CGCTTACCGG ATACCTGTCC
```

-continued

6421 GCCTTTCTCC CTTCGGGAAG CGTGGCGCTT TCTCATAGCT CACGCTGTAG GTATCTCAGT
6481 TCGGTGTAGG TCGTTCGCTC CAAGCTGGGC TGTGTGCACG AACCCCCCGT TCAGCCCGAC
6541 CGCTGCGCCT TATCCGGTAA CTATCGTCTT GAGTCCAACC CGGTAAGACA CGACTTATCG
6601 CCACTGGCAG CAGCCACTGG TAACAGGATT AGCAGAGCGA GGTATGTAGG CGGTGCTACA
6661 GAGTTCTTGA AGTGGTGGCC TAACTACGGC TACACTAGAA GGACAGTATT TGGTATCTGC
6721 GCTCTGCTGA AGCCAGTTAC CTTCGGAAAA AGAGTTGGTA GCTCTTGATC CGGCAAACAA
6781 ACCACCGCTG GTAGCGGTGG TTTTTTTGTT TGCAAGCAGC AGATTACGCG CAGAAAAAAA
6841 GGATCTCAAG AAGATCCTTT GATCTTTTCT ACGGGGTCTG ACGCTCAGTG GAACGAAAAC
6901 TCACGTTAAG GGATTTTGGT CATGAGATTA TCAAAAAGGA TCTTCACCTA GATCCTTTTA
6961 AATTAAAAAT GAAGTTTTAA ATCAATCTAA AGTATATATG AGTAAACTTG GTCTGACAGT
7021 TACCAATGCT TAATCAGTGA GGCACCTATC TCAGCGATCT GTCTATTTCG TTCATCCATA
7081 GTTGCCTGAC TCCCCGTCGT GTAGATAACT ACGATACGGG AGGGCTTACC ATCTGGCCCC
7141 AGTGCTGCAA TGATACCGCG AGACCCACGC TCACCGGCTC CAGATTTATC AGCAATAAAC
7201 CAGCCAGCCG GAAGGGCCGA GCGCAGAAGT GGTCCTGCAA CTTTATCCGC CTCCATCCAG
7261 TCTATTAATT GTTGCCGGGA AGCTAGAGTA AGTAGTTCGC CAGTTAATAG TTTGCGCAAC
7321 GTTGTTGCCA TTGCTACAGG CATCGTGGTG TCACGCTCGT CGTTTGGTAT GGCTTCATTC
7381 AGCTCCGGTT CCCAACGATC AAGGCGAGTT ACATGATCCC CCATGTTGTG CAAAAAAGCG
7441 GTTAGCTCCT TCGGTCCTCC GATCGTTGTC AGAAGTAAGT TGGCCGCAGT GTTATCACTC
7501 ATGGTTATGG CAGCACTGCA TAATTCTCTT ACTGTCATGC CATCCGTAAG ATGCTTTTCT
7561 GTGACTGGTG AGTACTCAAC CAAGTCATTC TGAGAATAGT GTATGCGGCG ACCGAGTTGC
7621 TCTTGCCCGG CGTCAATACG GGATAATACC GCGCCACATA GCAGAACTTT AAAAGTGCTC
7681 ATCATTGGAA AACGTTCTTC GGGGCGAAAA CTCTCAAGGA TCTTACCGCT GTTGAGATCC
7741 AGTTCGATGT AACCCACTCG TGCACCCAAC TGATCTTCAG CATCTTTTAC TTTCACCAGC
7801 GTTTCTGGGT GAGCAAAAAC AGGAAGGCAA AATGCCGCAA AAAAGGGAAT AAGGGCGACA
7861 CGGAAATGTT GAATACTCAT ACTCTTCCTT TTTCAATATT ATTGAAGCAT TTATCAGGGT
7921 TATTGTCTCA TGAGCGGATA CATATTTGAA TGTATTTAGA AAAATAAACA AATAGGGGTT
7981 CCGCGCACAT TTCCCCGAAA AGTGCCACCT AAATTGTAAG CGTTAATATT TTGTTAAAAT
8041 TCGCGTTAAA TTTTTGTTAA ATCAGCTCAT TTTTTAACCA ATAGGCCGAA ATCGGCAAAA
8101 TCCCTTATAA ATCAAAAGAA TAGACCGAGA TAGGGTTGAG TGTTGTTCCA GTTTGGAACA
8161 AGAGTCCACT ATTAAAGAAC GTGGACTCCA ACGTCAAAGG GCGAAAAACC GTCTATCAGG
8221 GCGATGGCCC ACTACGTGAA CCATCACCCT AATCAAGTTT TTTGGGGTCG AGGTGCCGTA
8281 AAGCACTAAA TCGGAACCCT AAAGGGAGCC CCCGATTTAG AGCTTGACGG GGAAAGCCGG
8341 CGAACGTGGC GAGAAAGGAA GGGAAGAAAG CGAAAGGAGC GGGCGCTAGG GCGCTGGCAA
8401 GTGTAGCGGT CACGCTGCGC GTAACCACCA CACCCGCCGC GCTTAATGCG CCGCTACAGG
8461 GCGCGTCCCA TTCGCCATTC AGGCTGCGCA ACTGTTGGGA AGGGCGATCG GTGCGGGCCT
8521 CTTCGCTATT ACGCCAGTCG ACCATAGCCA ATTCAATATG GCGTATATGG ACTCATGCCA
8581 ATTCAATATG GTGGATCTGG ACCTGTGCCA ATTCAATATG GCGTATATGG ACTCGTGCCA
8641 ATTCAATATG GTGGATCTGG ACCCCAGCCA ATTCAATATG GCGGACTTGG CACCATGCCA
8701 ATTCAATATG GCGGACTTGG CACTGTGCCA ACTGGGGAGG GGTCTACTTG GCACGGTGCC
8761 AAGTTTGAGG AGGGGTCTTG GCCCTGTGCC AAGTCCGCCA TATTGAATTG GCATGGTGCC

-continued

```
8821 AATAATGGCG GCCATATTGG CTATATGCCA GGATCAATAT ATAGGCAATA TCCAATATGG

8881 CCCTATGCCA ATATGGCTAT TGGCCAGGTT CAATACTATG TATTGGCCCT ATGCCATATA

8941 GTATTCCATA TATGGGTTTT CCTATTGACG TAGATAGCCC CTCCCAATGG GCGGTCCCAT

9001 ATACCATATA TGGGGCTTCC TAATACCGCC CATAGCCACT CCCCCATTGA CGTCAATGGT

9061 CTCTATATAT GGTCTTTCCT ATTGACGTCA TATGGGCGGT CCTATTGACG TATATGGCGC

9121 CTCCCCCATT GACGTCAATT ACGGTAAATG GCCCGCCTGG CTCAATGCCC ATTGACGTCA

9181 ATAGGACCAC CCACCATTGA CGTCAATGGG ATGGCTCATT GCCCATTCAT ATCCGTTCTC

9241 ACGCCCCCTA TTGACGTCAA TGACGGTAAA TGGCCCACTT GGCAGTACAT CAATATCTAT

9301 TAATAGTAAC TTGGCAAGTA CATTACTATT GGAAGGACGC CAGGGTACAT TGGCAGTACT

9361 CCCATTGACG TCAATGGCGG TAAATGGCCC GCGATGGCTG CCAAGTACAT CCCCATTGAC

9421 GTCAATGGGG AGGGGCAATG ACGCAAATGG GCGTTCCATT GACGTAAATG GGCGGTAGGC

9481 GTGCCTAATG GGAGGTCTAT ATAAGCAATG CTCGTTTAGG GAAC
```

Vector backbone sequences are represented by uppercase letters. Underlined segments of the sequence are as follows:

35-51: SP6 promoter 64-78: β-globin translational leader sequence 94-114: nuclear localization sequence from SV40 large T-antigen 139-4242: dCas 9

4243-4287: $(GGS)_5$ linker (SEQ ID NO:17) (not underlined)

4294-5535: zebrafish psip1a 5573-5768: SV40 polyadenylation signal 7020-7880: $Amp^R$ gene.

A map of this vector is shown in FIG. 23.

The nucleotide sequence of the pCS-zpsip1a-$(GGS)_5$-dCas9-NLS vector is:

```
                                                          (SEQ ID NO: 9)
   1 CGCCATTCTG CCTGGGGACG TCGGAGCAAG CTTGATTTAG GTGACACTAT AGAATACAAG

  61 CTACTTGTTC TTTTTGCAGG ATccgccacc atggctcagg atttcaaagc tggtgatctg

 121 atttttgcta agatgaaggg ttatccacac tggcctgcaa ggattgatga gattccagat

 181 ggtgctgtca aaccatcaaa tataaaattt cccatcttct tttttggcac tcatgaaaca

 241 gcattcctgg gtcctaaaga catattcccc tatttgacca ataaagacaa atatggcaaa

 301 cctaacaaaa ggaagggttt caatgaaggc ttgtgggaaa ttgaaaacaa tcctaaagtg

 361 gagcttaatg gacacaaggt aaaaaaggtt ggagaagttt caattaaaga tttgagcagc

 421 aatgaagagg gagatgatga gaagaggaca aagtcagctc aaattgctca cagtgagggg

 481 ctggaggacg aggtggacat tgagaaggaa gatggtggtg acatggacgt ttctgatcag

 541 agacttgtta aagatgaaga cctatcacag aaagattcga caaatgtcac tgccaaagct

 601 aaaagaggaa ggaagagaaa gagtgatgct gaacaagact ctgatacaga aaattcaagc

 661 ccaactgcag gcggttccgg tttagatttc ctatcaacag gtacatcaat tatgttactg

 721 aagcgcagag gaaggaaatc taaaacagag aagtcaataa tactacaaca acaggcttca

 781 aaggaattac caaggtcagg taaagatgga aagagagatg aaagaaaagg tgacaaaaga

 841 aaggagtcca cactgcagaa gttgcacggg gagattaaga catcattgaa gattggtaat

 901 ttagatgtaa ggaaatgtgt acatgcattg gatgagttaa gctctctaca tgttaccact

 961 caacatcttc agagacatag tgaactcata gcaactctga aaaagatctg cagattcaaa

1021 tccagccagg atgtgatgga caaagctatt atgctatata ataagtttaa aagtatgttt

1081 ttaatgggag aaggagaatc agtgctaagt caggtgctca ataaaagtct gactgaacag

1141 aaactatttg aagaagccaa gaggggagtc ctaaaaaaca cagaacaaac taaagagcag

1201 aaagatacca agattttgaa tgaagacttc aactccgaag aggacgctga gacagagaag

1261 gacaaattag gaggaaacat cttatctatg gtgaaaaaca acatgactaa tcctgcagaa
```

-continued

```
1321 gagtctgtcg gtggtagtgg aggttcagga ggatccgggg ggagcggagg gagccggcca
1381 atggacaaga agtactccat tgggctcgct atcggcacaa acagcgtcgg ctgggccgtc
1441 attacggacg agtacaaggt gccgagcaaa aaattcaaag ttctgggcaa taccgatcgc
1501 cacagcataa agaagaacct cattggcgcc ctcctgttcg actccgggga gacggccgaa
1561 gccacgcggc tcaaaagaac agcacggcgc agatataccc gcagaaagaa tcggatctgc
1621 tacctgcagg agatctttag taatgagatg gctaaggtgg atgactcttt cttccatagg
1681 ctggaggagt cctttttggt ggaggaggat aaaaagcacg agcgccaccc aatctttggc
1741 aatatcgtgg acgaggtggc gtaccatgaa aagtacccaa ccatatatca tctgaggaag
1801 aagcttgtag acagtactga taaggctgac ttgcggttga tctatctcgc gctggcgcat
1861 atgatcaaat ttcggggaca cttcctcatc gagggggacc tgaacccaga caacagcgat
1921 gtcgacaaac tctttatcca actggttcag acttacaatc agcttttcga agagaacccg
1981 atcaacgcat ccggagttga cgccaaagca atcctgagcg ctaggctgtc caaatcccgg
2041 cggctcgaaa acctcatcgc acagctccct ggggagaaga agaacggcct gtttggtaat
2101 cttatcgccc tgtcactcgg gctgaccccc aactttaaat ctaacttcga cctggccgaa
2161 gatgccaagc ttcaactgag caaagacacc tacgatgatg atctcgacaa tctgctggcc
2221 cagatcggcg accagtacgc agaccttttt ttggcggcaa agaacctgtc agacgccatt
2281 ctgctgagtg atattctgcg agtgaacacg gagatcacca aagctccgct gagcgctagt
2341 atgatcaagc gctatgatga gcaccaccaa gacttgactt tgctgaaggc ccttgtcaga
2401 cagcaactgc ctgagaagta caaggaaatt ttcttcgatc agtctaaaaa tggctacgcc
2461 ggatacattg acggcggagc aagccaggag gaattttaca aatttattaa gcccatcttg
2521 gaaaaaatgg acggcaccga ggagctgctg gtaaagctta acagagaaga tctgttgcgc
2581 aaacagcgca ctttcgacaa tggaagcatc ccccaccaga ttcacctggg cgaactgcac
2641 gctatcctca ggcggcaaga ggatttctac ccctttttga aagataacag ggaaaagatt
2701 gagaaaatcc tcacatttcg gataccctac tatgtaggcc ccctcgcccg gggaaattcc
2761 agattcgcgt ggatgactcg caaatcagaa gagaccatca ctccctggaa cttcgaggaa
2821 gtcgtggata agggggcctc tgcccagtcc ttcatcgaaa ggatgactaa ctttgataaa
2881 aatctgccta acgaaaaggt gcttcctaaa cactctctgc tgtacgagta cttcacagtt
2941 tataacgagc tcaccaaggt caaatacgtc acagaaggga tgagaaagcc agcattcctg
3001 tctggagagc agaagaaagc tatcgtggac ctcctcttca agacgaaccg gaaagttacc
3061 gtgaaacagc tcaaagaaga ctatttcaaa aagattgaat gtttcgactc tgttgaaatc
3121 agcggagtgg aggatcgctt caacgcatcc ctgggaacgt atcacgatct cctgaaaatc
3181 attaaagaca aggacttcct ggacaatgag gagaacgagg acattcttga ggacattgtc
3241 ctcaccctta cgttgtttga agatagggag atgattgaag aacgcttgaa aacttacgct
3301 catctcttcg acgacaaagt catgaaacag ctcaagaggc gccgatatac aggatggggg
3361 cggctgtcaa gaaaactgat caatgggatc cgagacaagc agagtggaaa gacaatcctg
3421 gattttctta agtccgatgg atttgccaac aggaacttca tgcagttgat ccatgatgac
3481 tctctcacct ttaaggagga catccagaaa gcacaagttt ctggccaggg ggacagtctt
3541 cacgagcaca tcgctaatct tgcaggtagc ccagctatca aaaagggaat actgcagacc
3601 gttaaggtcg tggatgaact cgtcaaagta atgggaaggc ataagcccga gaatatcgtt
3661 atcgagatgg cccgagagaa ccaaactacc cagaagggac agaagaacag tagggaaagg
```

-continued

```
3721 atgaagagga ttgaagaggg tataaaagaa ctggggtccc aaatccttaa ggaacaccca
3781 gttgaaaaca cccagcttca gaatgagaag ctctacctgt actacctgca gaacggcagg
3841 gacatgtacg tggatcagga actggacatc aatcggctct ccgactacga cgtggatgct
3901 atcgtgcccc agtcttttct caaagatgat tctattgata ataaagtgtt gacaagatcc
3961 gataaaaata gagggaagag tgataacgtc ccctcagaag aagttgtcaa gaaaatgaaa
4021 aattattggc ggcagctgct gaacgccaaa ctgatcacac aacggaagtt cgataatctg
4081 actaaggctg aacgaggtgg cctgtctgag ttggataaag ccggcttcat caaaaggcag
4141 cttgttgaga cacgccagat caccaagcac gtggcccaaa ttctcgattc acgcatgaac
4201 accaagtacg atgaaaatga caaactgatt cgagaggtga aagttattac tctgaagtct
4261 aagctggtct cagatttcag aaaggacttt cagttttata aggtgagaga gatcaacaat
4321 taccaccatg cgcatgatgc ctacctgaat gcagtggtag gcactgcact tatcaaaaaa
4381 tatcccaagc ttgaatctga atttgtttac ggagactata aagtgtacga tgttaggaaa
4441 atgatcgcaa agtctgagca ggaaataggc aaggccaccg ctaagtactt cttttacagc
4501 aatattatga atttttttcaa gaccgagatt acactggcca atggagagat tcggaagcga
4561 ccacttatcg aaacaaacgg agaaacagga gaaatcgtgt gggacaaggg tagggatttc
4621 gcgacagtcc ggaaggtcct gtccatgccg caggtgaaca tcgttaaaaa gaccgaagta
4681 cagaccggag gcttctccaa ggaaagtatc ctcccgaaaa ggaacagcga caagctgatc
4741 gcacgcaaaa aagattggga ccccaagaaa tacggcggat tcgattctcc tacagtcgct
4801 tacagtgtac tggttgtggc caaagtggag aaagggaagt ctaaaaaact caaaagcgtc
4861 aaggaactgc tgggcatcac aatcatggag cgatcaagct tcgaaaaaaa ccccatcgac
4921 tttctcgagg cgaaaggata taaagaggtc aaaaaagacc tcatcattaa gcttcccaag
4981 tactctctct ttgagcttga aaacggccgg aaacgaatgc tcgctagtgc gggcgagctg
5041 cagaaaggta acgagctggc actgccctct aaatacgtta atttcttgta tctggccagc
5101 cactatgaaa agctcaaagg gtctcccgaa gataatgagc agaagcagct gttcgtggaa
5161 caacacaaac actaccttga tgagatcatc gagcaaataa gcgaattctc caaaagagtg
5221 atcctcgccg acgctaacct cgataaggtg ctttctgctt acaataagca cagggataag
5281 cccatcaggg agcaggcaga aaacattatc cacttgttta ctctgaccaa cttgggcgcg
5341 cctgcagcct tcaagtactt cgacaccacc atagacagaa agcggtacac ctctacaaag
5401 gaggtcctgg acgccacact gattcatcag tcaattacgg ggctctatga aacaagaatc
5461 gacctctctc agctcggtgg agacggtggt agtggaggtt caggaggatc cgggggggagc
5521 ggagggagcg ctagcATGcc caagaagaag aggaaggtgg gtggttccTA GcTCGAGCCT
5581 CTAGAACTAT AGTGAGTCGT ATTACGTAGA TCCAGACATG ATAAGATACA TTGATGAGTT
5641 TGGACAAACC ACAACTAGAA TGCAGTGAAA AAAATGCTTT ATTTGTGAAA TTTGTGATGC
5701 TATTGCTTTA TTTGTAACCA TTATAAGCTG CAATAAACAA GTTAACAACA ACAATTGCAT
5761 TCATTTTATG TTTCAGGTTC AGGGGGAGGT GTGGGAGGTT TTTTAATTCG CGGCCGCGGC
5821 GCCAATGCAT TGGGCCCGGT ACCCAGCTTT TGTTCCCTTT AGTGAGGGTT AATTGCGCGC
5881 TTGGCGTAAT CATGGTCATA GCTGTTTCCT GTGTGAAATT GTTATCCGCT CACAATTCCA
5941 CACAACATAC GAGCCGGAAG CATAAAGTGT AAAGCCTGGG GTGCCTAATG AGTGAGCTAA
6001 CTCACATTAA TTGCGTTGCG CTCACTGCCC GCTTTCCAGT CGGGAAACCT GTCGTGCCAG
6061 CTGCATTAAT GAATCGGCCA ACGCGCGGGG AGAGGCGGTT TGCGTATTGG GCGCTCTTCC
6121 GCTTCCTCGC TCACTGACTC GCTGCGCTCG GTCGTTCGGC TGCGGCGAGC GGTATCAGCT
```

-continued

6181 CACTCAAAGG CGGTAATACG GTTATCCACA GAATCAGGGG ATAACGCAGG AAAGAACATG
6241 TGAGCAAAAG GCCAGCAAAA GGCCAGGAAC CGTAAAAAGG CCGCGTTGCT GGCGTTTTTC
6301 CATAGGCTCC GCCCCCCTGA CGAGCATCAC AAAAATCGAC GCTCAAGTCA GAGGTGGCGA
6361 AACCCGACAG GACTATAAAG ATACCAGGCG TTTCCCCCTG GAAGCTCCCT CGTGCGCTCT
6421 CCTGTTCCGA CCCTGCCGCT TACCGGATAC CTGTCCGCCT TTCTCCCTTC GGGAAGCGTG
6481 GCGCTTTCTC ATAGCTCACG CTGTAGGTAT CTCAGTTCGG TGTAGGTCGT TCGCTCCAAG
6541 CTGGGCTGTG TGCACGAACC CCCCGTTCAG CCCGACCGCT GCGCCTTATC CGGTAACTAT
6601 CGTCTTGAGT CCAACCCGGT AAGACACGAC TTATCGCCAC TGGCAGCAGC CACTGGTAAC
6661 AGGATTAGCA GAGCGAGGTA TGTAGGCGGT GCTACAGAGT TCTTGAAGTG GTGGCCTAAC
6721 TACGGCTACA CTAGAAGGAC AGTATTTGGT ATCTGCGCTC TGCTGAAGCC AGTTACCTTC
6781 GGAAAAAGAG TTGGTAGCTC TTGATCCGGC AAACAAACCA CCGCTGGTAG CGGTGGTTTT
6841 TTTGTTTGCA AGCAGCAGAT TACGCGCAGA AAAAAAGGAT CTCAAGAAGA TCCTTTGATC
6901 TTTTCTACGG GGTCTGACGC TCAGTGGAAC GAAAACTCAC GTTAAGGGAT TTTGGTCATG
6961 AGATTATCAA AAAGGATCTT CACCTAGATC CTTTTAAATT AAAAATGAAG TTTTAAATCA
7021 ATCTAAAGTA TATATGAGTA AACTTGGTCT GACAGTTACC AATGCTTAAT CAGTGAGGCA
7081 CCTATCTCAG CGATCTGTCT ATTTCGTTCA TCCATAGTTG CCTGACTCCC CGTCGTGTAG
7141 ATAACTACGA TACGGGAGGG CTTACCATCT GGCCCCAGTG CTGCAATGAT ACCGCGAGAC
7201 CCACGCTCAC CGGCTCCAGA TTTATCAGCA ATAAACCAGC CAGCCGGAAG GGCCGAGCGC
7261 AGAAGTGGTC CTGCAACTTT ATCCGCCTCC ATCCAGTCTA TTAATTGTTG CCGGGAAGCT
7321 AGAGTAAGTA GTTCGCCAGT TAATAGTTTG CGCAACGTTG TTGCCATTGC TACAGGCATC
7381 GTGGTGTCAC GCTCGTCGTT TGGTATGGCT TCATTCAGCT CCGGTTCCCA ACGATCAAGG
7441 CGAGTTACAT GATCCCCCAT GTTGTGCAAA AAAGCGGTTA GCTCCTTCGG TCCTCCGATC
7501 GTTGTCAGAA GTAAGTTGGC CGCAGTGTTA TCACTCATGG TTATGGCAGC ACTGCATAAT
7561 TCTCTTACTG TCATGCCATC CGTAAGATGC TTTTCTGTGA CTGGTGAGTA CTCAACCAAG
7621 TCATTCTGAG AATAGTGTAT GCGGCGACCG AGTTGCTCTT GCCCGGCGTC AATACGGGAT
7681 AATACCGCGC CACATAGCAG AACTTTAAAA GTGCTCATCA TTGGAAAACG TTCTTCGGGG
7741 CGAAAACTCT CAAGGATCTT ACCGCTGTTG AGATCCAGTT CGATGTAACC CACTCGTGCA
7801 CCCAACTGAT CTTCAGCATC TTTTACTTTC ACCAGCGTTT CTGGGTGAGC AAAAACAGGA
7861 AGGCAAAATG CCGCAAAAAA GGGAATAAGG GCGACACGGA AATGTTGAAT ACTCATACTC
7921 TTCCTTTTTC AATATTATTG AAGCATTTAT CAGGGTTATT GTCTCATGAG CGGATACATA
7981 TTTGAATGTA TTTAGAAAAA TAAACAAATA GGGGTTCCGC GCACATTTCC CCGAAAAGTG
8041 CCACCTAAAT TGTAAGCGTT AATATTTTGT TAAAATTCGC GTTAAATTTT TGTTAAATCA
8101 GCTCATTTTT TAACCAATAG GCCGAAATCG GCAAAATCCC TTATAAATCA AAAGAATAGA
8161 CCGAGATAGG GTTGAGTGTT GTTCCAGTTT GGAACAAGAG TCCACTATTA AAGAACGTGG
8221 ACTCCAACGT CAAAGGGCGA AAAACCGTCT ATCAGGGCGA TGGCCCACTA CGTGAACCAT
8281 CACCCTAATC AAGTTTTTTG GGGTCGAGGT GCCGTAAAGC ACTAAATCGG AACCCTAAAG
8341 GGAGCCCCCG ATTTAGAGCT TGACGGGGAA AGCCGGCGAA CGTGGCGAGA AAGGAAGGGA
8401 AGAAAGCGAA AGGAGCGGGC GCTAGGGCGC TGGCAAGTGT AGCGGTCACG CTGCGCGTAA
8461 CCACCACACC CGCCGCGCTT AATGCGCCGC TACAGGGCGC GTCCCATTCG CCATTCAGGC
8521 TGCGCAACTG TTGGGAAGGG CGATCGGTGC GGGCCTCTTC GCTATTACGC CAGTCGACCA

-continued

```
8581 TAGCCAATTC AATATGGCGT ATATGGACTC ATGCCAATTC AATATGGTGG ATCTGGACCT

8641 GTGCCAATTC AATATGGCGT ATATGGACTC GTGCCAATTC AATATGGTGG ATCTGGACCC

8701 CAGCCAATTC AATATGGCGG ACTTGGCACC ATGCCAATTC AATATGGCGG ACTTGGCACT

8761 GTGCCAACTG GGGAGGGGTC TACTTGGCAC GGTGCCAAGT TTGAGGAGGG GTCTTGGCCC

8821 TGTGCCAAGT CCGCCATATT GAATTGGCAT GGTGCCAATA ATGGCGGCCA TATTGGCTAT

8881 ATGCCAGGAT CAATATATAG GCAATATCCA ATATGGCCCT ATGCCAATAT GGCTATTGGC

8941 CAGGTTCAAT ACTATGTATT GGCCCTATGC CATATAGTAT TCCATATATG GGTTTTCCTA

9001 TTGACGTAGA TAGCCCCTCC CAATGGGCGG TCCCATATAC CATATATGGG GCTTCCTAAT

9061 ACCGCCCATA GCCACTCCCC CATTGACGTC AATGGTCTCT ATATATGGTC TTTCCTATTG

9121 ACGTCATATG GGCGGTCCTA TTGACGTATA TGGCGCCTCC CCCATTGACG TCAATTACGG

9181 TAAATGGCCC GCCTGGCTCA ATGCCCATTG ACGTCAATAG GACCACCCAC CATTGACGTC

9241 AATGGGATGG CTCATTGCCC ATTCATATCC GTTCTCACGC CCCCTATTGA CGTCAATGAC

9301 GGTAAATGGC CCACTTGGCA GTACATCAAT ATCTATTAAT AGTAACTTGG CAAGTACATT

9361 ACTATTGGAA GGACGCCAGG GTACATTGGC AGTACTCCCA TTGACGTCAA TGGCGGTAAA

9421 TGGCCCGCGA TGGCTGCCAA GTACATCCCC ATTGACGTCA ATGGGGAGGG GCAATGACGC

9481 AAATGGGCGT TCCATTGACG TAAATGGGCG GTAGGCGTGC CTAATGGGAG GTCTATATAA

9541 GCAATGCTCG TTTAGGGAAC
```

Vector backbone sequences are represented by uppercase letters. Underlined segments of the sequence are as follows:

35-51: SP6 promoter
64-78: β-globin translational leader sequence
91-1329: zebrafish psip1a
1330-1374: $(GGS)_5$ linker (SEQ ID NO:17) (not underlined)
1381-5484: dCas 9
5539-5559: nuclear localization sequence from SV40 large T-antigen
5609-5804: SV40 polyadenylation signal
7056-7916: AmpR gene. A map of this vector is shown in FIG. 24.

Additional vectors are constructed with different linker sequences between the Cas9-encoding and psip1a-encoding sequences. In these constructs, the $(GGS)_5$ linker (SEQ ID NO:17) is replaced by the more rigid $(EAAAK)_n$ linker (in which n=1-4) (SEQ ID NO:18) and the flexible $(GGGGS)_n$ linker (in which n=1-4) (SEQ ID NO:19).

Example 9: pLTRB-CMV-tdTomato Transgene Vector

This plasmid was constructed by gateway cloning using p5E-CMV, pME-tdTomato, and the two-way Gateway cloning vector pLTRB-R4R2. The nucleotide sequence of this vector is:

```
                                                          (SEQ ID NO: 10)
  1 TATAGTGAGT CGTATTACAA TTCACTGGCC GTCGTTTTAC AACGTCGTGA CTGGGAAAAC

 61 CCTGGCGTTA CCCAACTTAA TCGCCTTGCA GCACATCCCC CTTTCGCCAG CTGGCGTAAT

121 AGCGAAGAGG CCCGCACCGA TCGCCCTTCC CAACAGTTGC GCAGCCTGAA TGGCGAATGG

181 ACGCGCCCTG TAGCGGCGCA TTAAGCGCGG CGGGTGTGGT GGTTACGCGC AGCGTGACCG

241 CTACACTTGC CAGCGCCCTA GCGCCCGCTC CTTTCGCTTT CTTCCCTTCC TTTCTCGCCA

301 CGTTCGCCGG CTTTCCCCGT CAAGCTCTAA ATCGGGGGCT CCCTTTAGGG TTCCGATTTA

361 GTGCTTTACG GCACCTCGAC CCCAAAAAAC TTGATTAGGG TGATGGTTCA CGTAGTGGGC

421 CATCGCCCTG ATAGACGGTT TTTCGCCCTT TGACGTTGGA GTCCACGTTC TTTAATAGTG

481 GACTCTTGTT CCAAACTGGA ACAACACTCA ACCCTATCTC GGTCTATTCT TTTGATTTAT

541 AAGGGATTTT GCCGATTTCG GCCTATTGGT TAAAAAATGA GCTGATTTAA CAAAAATTTA

601 ACGCGAATTT TAACAAAATA TTAACGCTTA CAATTTCCTG ATGCGGTATT TTCTCCTTAC

661 GCATCTGTGC GGTATTTCAC ACCGCATCAG GTGGCACTTT TCGGGGAAAT GTGCGCGGAA

721 CCCCTATTTG TTTATTTTTC TAAATACATT CAAATATGTA TCCGCTCATG AGACAATAAC
```

-continued

781 CCTGATAAAT GCTTCAATAA TATTGAAAAA GGAAGAGTAT GAGTATTCAA CATTTCCGTG

841 TCGCCCTTAT TCCCTTTTTT GCGGCATTTT GCCTTCCTGT TTTTGCTCAC CCAGAAACGC

901 TGGTGAAAGT AAAAGATGCT GAAGATCAGT TGGGTGCACG AGTGGGTTAC ATCGAACTGG

961 ATCTCAACAG CGGTAAGATC CTTGAGAGTT TTCGCCCCGA AGAACGTTTT CCAATGATGA

1021 GCACTTTTAA AGTTCTGCTA TGTGGCGCGG TATTATCCCG TATTGACGCC GGGCAAGAGC

1081 AACTCGGTCG CCGCATACAC TATTCTCAGA ATGACTTGGT TGAGTACTCA CCAGTCACAG

1141 AAAAGCATCT TACGGATGGC ATGACAGTAA GAGAATTATG CAGTGCTGCC ATAACCATGA

1201 GTGATAACAC TGCGGCCAAC TTACTTCTGA CAACGATCGG AGGACCGAAG GAGCTAACCG

1261 CTTTTTTGCA CAACATGGGG GATCATGTAA CTCGCCTTGA TCGTTGGGAA CCGGAGCTGA

1321 ATGAAGCCAT ACCAAACGAC GAGCGTGACA CCACGATGCC TGTAGCAATG GCAACAACGT

1381 TGCGCAAACT ATTAACTGGC GAACTACTTA CTCTAGCTTC CCGGCAACAA TTAATAGACT

1441 GGATGGAGGC GGATAAAGTT GCAGGACCAC TTCTGCGCTC GGCCCTTCCG GCTGGCTGGT

1501 TTATTGCTGA TAAATCTGGA GCCGGTGAGC GTGGGTCTCG CGGTATCATT GCAGCACTGG

1561 GGCCAGATGG TAAGCCCTCC CGTATCGTAG TTATCTACAC GACGGGGAGT CAGGCAACTA

1621 TGGATGAACG AAATAGACAG ATCGCTGAGA TAGGTGCCTC ACTGATTAAG CATTGGTAAC

1681 TGTCAGACCA AGTTTACTCA TATATACTTT AGATTGATTT AAAACTTCAT TTTTAATTTA

1741 AAAGGATCTA GGTGAAGATC CTTTTTGATA ATCTCATGAC CAAAATCCCT TAACGTGAGT

1801 TTTCGTTCCA CTGAGCGTCA GACCCCGTAG AAAAGATCAA AGGATCTTCT TGAGATCCTT

1861 TTTTTCTGCG CGTAATCTGC TGCTTGCAAA CAAAAAAACC ACCGCTACCA GCGGTGGTTT

1921 GTTTGCCGGA TCAAGAGCTA CCAACTCTTT TTCCGAAGGT AACTGGCTTC AGCAGAGCGC

1981 AGATACCAAA TACTGTTCTT CTAGTGTAGC CGTAGTTAGG CCACCACTTC AAGAACTCTG

2041 TAGCACCGCC TACATACCTC GCTCTGCTAA TCCTGTTACC AGTGGCTGCT GCCAGTGGCG

2101 ATAAGTCGTG TCTTACCGGG TTGGACTCAA GACGATAGTT ACCGGATAAG GCGCAGCGGT

2161 CGGGCTGAAC GGGGGGTTCG TGCACACAGC CCAGCTTGGA GCGAACGACC TACACCGAAC

2221 TGAGATACCT ACAGCGTGAG CTATGAGAAA GCGCCACGCT TCCCGAAGGG AGAAAGGCGG

2281 ACAGGTATCC GGTAAGCGGC AGGGTCGGAA CAGGAGAGCG CACGAGGGAG CTTCCAGGGG

2341 GAAACGCCTG GTATCTTTAT AGTCCTGTCG GGTTTCGCCA CCTCTGACTT GAGCGTCGAT

2401 TTTTGTGATG CTCGTCAGGG GGGCGGAGCC TATGGAAAAA CGCCAGCAAC GCGGCCTTTT

2461 TACGGTTCCT GGCCTTTTGC TGGCCTTTTG CTCACATGTT CTTTCCTGCG TTATCCCCTG

2521 ATTCTGTGGA TAACCGTATT ACCGCCTTTG AGTGAGCTGA TACCGCTCGC CGCAGCCGAA

2581 CGACCGAGCG CAGCGAGTCA GTGAGCGAGG AAGCGGAAGA GCGCCCAATA CGCAAACCGC

2641 CTCTCCCCGC GCGTTGGCCG ATTCATTAAT GCAGCTGGCA CGACAGGTTT CCCGACTGGA

2701 AAGCGGGCAG TGAGCGCAAC GCAATTAATG TGAGTTAGCT CACTCATTAG GCACCCCAGG

2761 CTTTACACTT TATGCTTCCG GCTCGTATGT TGTGTGGAAT TGTGAGCGGA TAACAATTTC

2821 ACACAGGAAA CAGCTATGAC CATGATTACG CCAAGCTATT TAGGTGACAC TATAGAATAC

2881 TCAAGCTATG CATCCAACGC GTTGGGAGCT CTCCCATATG TATACTGGGT CTCTCTGGTT

2941 AGACCAGATC TGAGCCTGGG AGCTCTCTGG CTAACTAGGG AACCCACTGC TTAAGCCTCA

3001 ATAAAGCTTG CCTTGAGTGC TTCAAGTAGT GTGTGCCCGT CTGTTGTGTG ACTCTGGTAA

3061 CTAGAGATCC CTCAGACCCT TTTAGTCAGT GTGGAAAATC TCTAGCATAG GGATAACAGG

3121 GTAATCTCGA GTTGACGTCA GGAAACAGCT ATGACCATGA TTACGCCAAG CTATCAACTT

3181 TGTATAGAAA AGTTGAAGGC CTCTTCGCTA TTACGCCAGT CGACCGCCAA TTCAATATGG

-continued

3241 CGTATATGGA CTCATGCCAA TTCAATATGG TGGATCTGGA CCTGTGCCAA TTCAATATGG
3301 CGTATATGGA CTCGTGCCAA TTCAATATGG TGGATCTGGA CCCCAGCCAA TTCAATATGG
3361 CGGACTTGGC ACCATGCCAA TTCAATATGG CGGACCTGGC ACTGTGCCAA CTGGGGAGGG
3421 GTCTACTTGG CACGGTGCCA AGTTTGAGGA GGGGTCTTGG CCCTGTGCCA AGTCCGCCAT
3481 ATTGAATTGG CATGGTGCCA ATAATGGCGG CCATATTGGC TATATGCCAG GATCAATATA
3541 TAGGCAATAT CCAATATGGC CCTATGCCAA TATGGCTATT GGCCAGGTTC AATACTATGT
3601 ATTGGCCCTA TGCCATATAG TATTCCATAT ATGGGTTTTC CTATTGACGT AGATAGCCCC
3661 TCCCAATGGG CGGTCCCATA TACCATATAT GGGGCTTCCT AATACCGCCC ATAGCCACTC
3721 CCCCATTGAC GTCAATGGTC TCTATATATG GTCTTTCCTA TTGACGTCAT ATGGGCGGTC
3781 CTATTGACGT ATATGGCGCC TCCCCCATTG ACGTCAATTA CGGTAAATGG CCCGCCTGGC
3841 TCAATGCCCA TTGACGTCAA TAGGACCACC CACCATTGAC GTCAATGGGA TGGCTCATTG
3901 CCCATTCATA TCCGTTCTCA CGCCCCCTAT TGACGTCAAT GACGGTAAAT GGCCCACTTG
3961 GCAGTACATC AATATCTATT AATAGTAACT TGGCAAGTAC ATTACTATTG GAAGTACGCC
4021 AGGGTACATT GGCAGTACTC CCATTGACGT CAATGGCGGT AAATGGCCCG CGATGGCTGC
4081 CAAGTACATC CCCATTGACG TCAATGGGGA GGGGCAATGA CGCAAATGGG CGTTCCATTG
4141 ACGTAAATGG GCGGTAGGCG TGCCTAATGG GAGGTCTATA TAAGCAATGC TCGTTTAGGG
4201 AACCGCCATT CTGCCTGGGG ACGTCGGAGC AAGCTTGATT TAGGTGACAC TATAGAAAGT
4261 TTGTACAAAA AAGCAGGCTT GGTGAGCAAG GGCGAGGAGG TCATCAAAGA GTTCATGCGC
4321 TTCAAGGTGC GCATGGAGGG CTCCATGAAC GGCCACGAGT TCGAGATCGA GGGCGAGGGC
4381 GAGGGCCGCC CCTACGAGGG CACCCAGACC GCCAAGCTGA AGGTGACCAA GGGCGGCCCC
4441 CTGCCCTTCG CCTGGGACAT CCTGTCCCCC CAGTTCATGT ACGGCTCCAA GGCGTACGTG
4501 AAGCACCCCG CCGACATCCC CGATTACAAG AAGCTGTCCT TCCCCGAGGG CTTCAAGTGG
4561 GAGCGCGTGA TGAACTTCGA GGACGGCGGT CTGGTGACCG TGACCCAGGA CTCCTCCCTG
4621 CAGGACGGCA CGCTGATCTA CAAGGTGAAG ATGCGCGGCA CCAACTTCCC CCCCGACGGC
4681 CCCGTAATGC AGAAGAAGAC CATGGGCTGG GAGGCCTCCA CCGAGCGCCT GTACCCCCGC
4741 GACGGCGTGC TGAAGGGCGA GATCCACCAG GCCCTGAAGC TGAAGGACGG CGGCCACTAC
4801 CTGGTGGAGT TCAAGACCAT CTACATGGCC AAGAAGCCCG TGCAACTGCC CGGCTACTAC
4861 TACGTGGACA CCAAGCTGGA CATCACCTCC CACAACGAGG ACTACACCAT CGTGGAACAG
4921 TACGAGCGCT CCGAGGGCCG CCACCACCTG TTCCTGGGGC ATGGCACCGG CAGCACCGGC
4981 AGCGGCAGCT CCGGCACCGC CTCCTCCGAG GACAACAACA TGGCCGTCAT CAAAGAGTTC
5041 ATGCGCTTCA AGGTGCGCAT GGAGGGCTCC ATGAACGGCC ACGAGTTCGA GATCGAGGGC
5101 GAGGGCGAGG GCCGCCCCTA CGAGGGCACC CAGACCGCCA AGCTGAAGGT GACCAAGGGC
5161 GGCCCCCTGC CCTTCGCCTG GGACATCCTG TCCCCCCAGT TCATGTACGG CTCCAAGGCG
5221 TACGTGAAGC ACCCCGCCGA CATCCCCGAT TACAAGAAGC TGTCCTTCCC CGAGGGCTTC
5281 AAGTGGGAGC GCGTGATGAA CTTCGAGGAC GGCGGTCTGG TGACCGTGAC CCAGGACTCC
5341 TCCCTGCAGG ACGGCACGCT GATCTACAAG GTGAAGATGC GCGGCACCAA CTTCCCCCCC
5401 GACGGCCCCG TAATGCAGAA GAAGACCATG GGCTGGGAGG CCTCCACCGA GCGCCTGTAC
5461 CCCCGCGACG GCGTGCTGAA GGGCGAGATC CACCAGGCCC TGAAGCTGAA GGACGGCGGC
5521 CACTACCTGG TGGAGTTCAA GACCATCTAC ATGGCCAAGA AGCCCGTGCA ACTGCCCGGC
5581 TACTACTACG TGGACACCAA GCTGGACATC ACCTCCCACA ACGAGGACTA CACCATCGTG

-continued

```
5641 GAACAGTACG AGCGCTCCGA GGGCCGCCAC CACCTGTTCC TGTACGGCAT GGACGAGCTG
5701 TACAAGTAAC ACCCAGCTTT CTTGTACAAA GTGGTGTACC ATCGATGATG ATCCAGACAT
5761 GATAAGATAC ATTGATGAGT TTGGACAAAC CACAACTAGA ATGCAGTGAA AAAAATGCTT
5821 TATTTGTGAA ATTTGTGATG CTATTGCTTT ATTTGTAACC ATTATAAGCT GCAATAAACA
5881 AGTTAACAAC AACAATTGCA TTCATTTTAT GTTTCAGGTT CAGGGGGAGG TGTGGGAGGT
5941 TTTTTAAAGC AAGTAAAACC TCTACAAATG TGGTATGGCT GATTATGATC CTCTAGATCG
6001 TGCATGCTTC CGCGGATTAC CCTGTTATCC CTATGGAAGG GCTAATTCAC TCCCAACGAA
6061 GACAAGATCT GCTTTTTGCT TGTACTGGGT CTCTCTGGTT AGACCAGATC TGAGCCTGGG
6121 AGCTCTCTGG CTAACTAGGG AACCCACTGC TTAAGCCTCA ATAAAGCTTG CCTTGAGTGC
6181 TTCAAGTAGT GTGTGCCCGT CTGTTGTGTG ACTCTGGTAA CTAGAGATCC CTCAGACCCT
6241 TTTAGTCAGT GTGGAAAATC TCTAGCAGTA TACGGGCCCA ATTCGCCC
```

Underlined segments of the sequence are as follows:

714-1679: β-lactamase promoter and coding sequence
2928-3107: truncated HIV-1 LTR containing R and U5 sequences (SEQ ID NO:4)
3175-3195: attR4 sequences
3226-4203: CMV IE94 promoter
4238-4254: SP6 promoter
4257-4279: attB1 sequences
4280-5706: td-Tomato
5710-5734: attB2 sequences
5750-5884: SV40 polyadenylation signal
6034-6267: truncated HIV-1 LTR containing dU3, R and U5 sequences (SEQ ID NO:5).

A map of this vector is shown in FIG. 25.

Example 10: Targeted Integration in Zebrafish Embryos

This example describes targeted integration of a td-Tomato transgene in zebrafish. Transgenic zebrafish embryos (pTol2-CMV:EGFP-pA) that contained an integrated EGFP gene were constructed by Tol2-mediated transgenesis as described in Example 4. One-cell embryos obtained from adult zebrafish containing an exogenous EGFP gene that had been introduced by Tol2-mediated transgenesis of embryos (as described in Example 4) were used as target organisms. For each experiment, approximately 200 embryos were injected with a mixture of:

(a) 6.25 pg/embryo of a transgene cassette containing a td-Tomato coding region (as described in Example 9),
(b) 6.25 pg/embryo of integrase-encoding RNA (prepared as described in Example 3),
(c) 6.25 pg/embryo of RNA encoding the psip1a-Cas9 fusion protein (as described in Example 8), prepared by in vitro transcription with SP6 RNA polymerase, and
(d) 6.25 pg/embryo of guide RNA complementary to a portion of the EGFP coding region having the sequence:

(SEQ ID NO: 11)
5'-GTAGGTCAGGGTGGTCACGAGGG-3' in which the GGG sequence at the 3' end is the protospacer adjacent motif (PAM) sequence.

Because the target embryos are transgenic for EGFP, they exhibit green fluorescence. However, if the td-Tomato-encoding transgene cassette is integrated at the target sequence, the EGFP gene will be disrupted and the cell will exhibit red fluorescence, due to the integrated td-Tomato transgene.

Injected embryos were cultured in egg water (60 μg/ml Instant Ocean® sea salt) at 28.5° C. Five hours after injection, embryos were analyzed by confocal fluorescence microscopy. The results, shown in FIG. 26, indicate that several cells emitted red fluorescence, indicative of targeted integration of the td-Tomato transgene into the target site in the EGFP gene in those cells.

Example 11: Test System

Transgenic zebrafish (made, e.g., by I-SceI-mediated methods, Tol2-mediated methods, or the methods disclosed herein) containing an integrated EGFP gene (or any other gene providing a fluorescent readout) are selected in which a single exogenous EGFP gene is integrated at a locus that does not contain a coding region or regulatory element. This is achieved, for example, by outcrossing transgenic fish until a strain is obtained that contains a single EGFP insertion in a non-coding, non-regulatory region (confirmed, e.g., by determining the DNA sequence of the insertion site). Such a strain is used as a test system, e.g., for optimizing the methods and compositions disclosed herein. For example, targeted integration, into the EGFP sequences of such strains, of transgene cassettes containing sequences encoding a non-green fluorescent molecule, such as td-Tomato, results in loss of green fluorescence and acquisition of red fluorescence.

Example 12: Integrase Proteins with Additional Nuclear Localization Signals

This example provides results of an experiment to determine the effect of additional NLS sequences, in the integrase protein, on the efficiency of integration. The pFLi1ep:EGFP-pA transgene cassette (see Example 5) was co-injected into one-cell embryos with mRNA encoding one of three different integrase proteins: wild-type HIV-1 integrase, HIV-1 integrase with a c-myc NLS attached to the N-terminus, and HIV-1 integrase with a c-myc NLS attached to the C-terminus.

Six days post-fertilization, embryos were analyzed by confocal fluorescence microscopy and sorted into Groups (0 through 4) as described in Examples 3 and 5. The results, shown in FIG. 27, indicate that the presence of the c-myc NLS at the N-terminus of the integrase protein increases the efficiency of integration.

What is claimed is:

1. A polynucleotide comprising:

(a) one or more selection markers, wherein the selection markers are flanked by (b) first and second att sites, wherein the att sites are flanked by (c) first and second truncated retroviral long terminal repeats (LTRs), wherein the first truncated LTR is upstream of the first att site, the second truncated LTR is downstream of the second att site, and the first and second truncated retroviral LTRs are flanked by (d) recognition sites for a restriction enzyme, wherein cleavage of the recognition sites generates blunt ends; and (e) first and second 5'-ACTG-3' sequences, present at or near the termini of the polynucleotide, wherein the second truncated LTR sequence comprises:

```
                                            (SEQ. ID NO. 5)
TGGAAGGGCTAATTCACTCCCAACGAAGACAAGATCTGCTTTTTGCTTGT

ACTGGGTCTCTCTGGTTAGACCAGATCTGAGCCTGGGAGCTCTCTGGCTA

ACTAGGGAACCCACTGCTTAAGCCTCAATAAAGCTTGCCTTGAGTGCTTC

AAGTAGTGTGTGCCCGTCTGTTGTGTGACTCTGGTAACTAGAGATCCCTC

AGACCCTTTTAGTCAGTGTGGAAAATCTCTAGCA.
```

2. The polynucleotide of claim 1, wherein the retroviral LTRs are LTRs from a lentivirus comprising a human immunodeficiency virus (HIV).

3. The polynucleotide of claim 1, wherein the first truncated LTR sequence comprises:

```
                                            (SEQ. ID NO. 4)
GGTCTCTssCTGGTTAGACCAGATCTGsAGCCTGGGAGCTCTCTGGCTAA

CTAGGGAACCCACTGCTTAAGCCTCAATAAAGCTTGCCTTGAGTGCTTCA

AGTAGTGTGTGCCCGTCTGTTGTGTGACTCTGGTAACTAGAGATCCCTCA

GACCCTTTTAGTCAGTGTGGAAAATCTCTAGCA.
```

4. The polynucleotide of claim 1, wherein the first and second 5'-ACTG-3' sequences are present at the termini of the polynucleotide.

5. The polynucleotide of claim 1, wherein the first and second 5'-ACTG-3' sequences are present one base pair inside the termini of the polynucleotide.

6. The polynucleotide of claim 1, wherein the first and second 5'-ACTG-3' sequences are present two base pairs inside the termini of the polynucleotide.

7. The polynucleotide of claim 1, wherein:

the polynucleotide further comprises a transgene disposed between the first and second truncated retroviral LTRs.

8. A polynucleotide comprising:

(a) one or more selection markers, wherein the selection markers are flanked by (b) first and second att sites, wherein the att sites are flanked by (c) first and second truncated retroviral long terminal repeats (LTRs), wherein the first truncated LTR is upstream of the first att site, the second truncated LTR is downstream of the second att site, and the first and second truncated retroviral LTRs are flanked by (d) recognition sites for a restriction enzyme, wherein cleavage of the recognition sites generates blunt ends; and (e) first and second 5'-ACTG-3' sequences, present at or near the termini of the polynucleotide, wherein the second truncated LTR sequence comprises: TGGAAGGGCTAATTCACTCCCAACGAA-GACAAGATCTGCTTTTTGCTTGTACT GGGTCTCTCTGGTTAGACCAGATCT-GAGCCTGGGAGCTCTCTGGCTAACTAGG GAACCCACTGCTTAAGCCT-CAATAAAGCTTGCCTTGAGTGCTT-CAAGTAGTGT GTGCCCGTCTGTTGTGTGACTCTGGTAACTA-GAGATCCCTCAGACCCTTTTAG TCAGTGTG-GAAAATCTCTAGCA (SEQ. ID NO. 5), and wherein the polynucleotide further comprises a transgene disposed between the first and second truncated retroviral LTRs.

9. The polynucleotide of claim 8, wherein the retroviral LTRs are LTRs from a lentivirus comprising a human immunodeficiency virus (HIV).

10. The polynucleotide of claim 8, wherein the first and second 5'-ACTG-3' sequences are present at the termini of the polynucleotide.

11. The polynucleotide of claim 8, wherein the first and second 5'-ACTG-3' sequences are present one base pair inside the termini of the polynucleotide.

12. The polynucleotide of claim 8, wherein the first and second 5'-ACTG-3' sequences are present two base pairs inside the termini of the polynucleotide.

* * * * *

SEQUENCE LISTING

```
<160> NUMBER OF SEQ ID NOS: 19

<210> SEQ ID NO 1
<211> LENGTH: 634
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

tggaagggct aattcactcc caacgaagac aagatatcct tgatctgtgg atctaccaca     60

cacaaggcta cttccctgat tggcagaact acacaccagg gccaggggtc agatatccac    120

tgacctttgg atggtgctac aagctagtac cagttgagcc agataaggta gaagaggcca    180

ataaaggaga gaacaccagc ttgttacacc ctgtgagcct gcatggaatg gatgaccctg    240

agagagaagt gttagagtgg aggtttgaca gccgcctagc atttcatcac gtggcccgag    300

agctgcatcc ggagtacttc aagaactgct gacatcgagc ttgctacaag ggactttccg    360

ctggggactt tccagggagg cgtggcctgg gcgggactgg ggagtggcga gccctcagat    420

gctgcatata agcagctgct ttttgcctgt actgggtctc tctggttaga ccagatttga    480

gcctgggagc tctctggcta actagggaac ccactgctta agcctcaata aagcttgcct    540

tgagtgcttc aagtagtgtg tgcccgtctg ttgtgtgact ctggtaacta gagatccctc    600

agaccctttt agtcagtgtg gaaaatctct agca                                634


<210> SEQ ID NO 2
<211> LENGTH: 454
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

tggaagggct aattcactcc caacgaagac aagatatcct tgatctgtgg atctaccaca     60

cacaaggcta cttccctgat tggcagaact acacaccagg gccaggggtc agatatccac    120

tgacctttgg atggtgctac aagctagtac cagttgagcc agataaggta gaagaggcca    180

ataaaggaga gaacaccagc ttgttacacc ctgtgagcct gcatggaatg gatgaccctg    240

agagagaagt gttagagtgg aggtttgaca gccgcctagc atttcatcac gtggcccgag    300

agctgcatcc ggagtacttc aagaactgct gacatcgagc ttgctacaag ggactttccg    360

ctggggactt tccagggagg cgtggcctgg gcgggactgg ggagtggcga gccctcagat    420

gctgcatata agcagctgct ttttgcctgt actg                                454


<210> SEQ ID NO 3
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

tggaagggct aattcactcc caacgaagac aagatctgct ttttgcctgt actg          54
```

-continued

<210> SEQ ID NO 4
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ggtctctctg gttagaccag atttgagcct gggagctctc tggctaacta gggaacccac     60
tgcttaagcc tcaataaagc ttgccttgag tgcttcaagt agtgtgtgcc cgtctgttgt    120
gtgactctgg taactagaga tccctcagac ccttttagtc agtgtggaaa atctctagca    180

<210> SEQ ID NO 5
<211> LENGTH: 234
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
tggaagggct aattcactcc caacgaagac aagatctgct ttttgcctgt actgggtctc     60
tctggttaga ccagatttga gcctgggagc tctctggcta actagggaac ccactgctta    120
agcctcaata aagcttgcct tgagtgcttc aagtagtgtg tgcccgtctg ttgtgtgact    180
ctggtaacta gagatccctc agaccctttt agtcagtgtg gaaaatctct agca          234

<210> SEQ ID NO 6
<211> LENGTH: 1368
<212> TYPE: PRT
<213> ORGANISM: Streptococcus pyogenes

<400> SEQUENCE: 6

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

-continued

```
Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590
```

```
Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005
```

-continued

```
Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 7
<211> LENGTH: 413
<212> TYPE: PRT
<213> ORGANISM: Danio rerio

-continued

<400> SEQUENCE: 7

```
Met Ala Gln Asp Phe Lys Ala Gly Asp Leu Ile Phe Ala Lys Met Lys
1               5                   10                  15

Gly Tyr Pro His Trp Pro Ala Arg Ile Asp Glu Ile Pro Asp Gly Ala
            20                  25                  30

Val Lys Pro Ser Asn Ile Lys Phe Pro Ile Phe Phe Phe Gly Thr His
        35                  40                  45

Glu Thr Ala Phe Leu Gly Pro Lys Asp Ile Phe Pro Tyr Leu Thr Asn
    50                  55                  60

Lys Asp Lys Tyr Gly Lys Pro Asn Lys Arg Lys Gly Phe Asn Glu Gly
65                  70                  75                  80

Leu Trp Glu Ile Glu Asn Asn Pro Lys Val Glu Leu Asn Gly His Lys
                85                  90                  95

Val Lys Lys Val Gly Glu Val Ser Ile Lys Asp Leu Ser Ser Asn Glu
            100                 105                 110

Glu Gly Asp Asp Glu Lys Arg Thr Lys Ser Ala Gln Ile Ala His Ser
        115                 120                 125

Glu Gly Leu Glu Asp Glu Val Asp Ile Glu Lys Glu Asp Gly Gly Asp
    130                 135                 140

Met Asp Val Ser Asp Gln Arg Leu Val Lys Asp Glu Asp Leu Ser Gln
145                 150                 155                 160

Lys Asp Ser Thr Asn Val Thr Ala Lys Ala Lys Arg Gly Arg Lys Arg
                165                 170                 175

Lys Ser Asp Ala Glu Gln Asp Ser Asp Thr Glu Asn Ser Ser Pro Thr
            180                 185                 190

Ala Gly Gly Ser Gly Leu Asp Phe Leu Ser Thr Gly Thr Ser Ile Met
        195                 200                 205

Leu Leu Lys Arg Arg Gly Arg Lys Ser Lys Thr Glu Lys Ser Ile Ile
    210                 215                 220

Leu Gln Gln Gln Ala Ser Lys Glu Leu Pro Arg Ser Gly Lys Asp Gly
225                 230                 235                 240

Lys Arg Asp Glu Arg Lys Gly Asp Lys Arg Lys Glu Ser Thr Leu Gln
                245                 250                 255

Lys Leu His Gly Glu Ile Lys Thr Ser Leu Lys Ile Gly Asn Leu Asp
            260                 265                 270

Val Arg Lys Cys Val His Ala Leu Asp Glu Leu Ser Ser Leu His Val
        275                 280                 285

Thr Thr Gln His Leu Gln Arg His Ser Glu Leu Ile Ala Thr Leu Lys
    290                 295                 300

Lys Ile Cys Arg Phe Lys Ser Ser Gln Asp Val Met Asp Lys Ala Ile
305                 310                 315                 320

Met Leu Tyr Asn Lys Phe Lys Ser Met Phe Leu Met Gly Glu Gly Glu
                325                 330                 335

Ser Val Leu Ser Gln Val Leu Asn Lys Ser Leu Thr Glu Gln Lys Leu
            340                 345                 350

Phe Glu Glu Ala Lys Arg Gly Val Leu Lys Asn Thr Glu Gln Thr Lys
        355                 360                 365

Glu Gln Lys Asp Thr Lys Ile Leu Asn Glu Asp Phe Asn Ser Glu Glu
    370                 375                 380

Asp Ala Glu Thr Glu Lys Asp Lys Leu Gly Gly Asn Ile Leu Ser Met
385                 390                 395                 400

Val Lys Asn Asn Met Thr Asp Pro Ala Glu Glu Ser Val
                405                 410
```

-continued

<210> SEQ ID NO 8
<211> LENGTH: 9524
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8
cgccattctg cctggggacg tcggagcaag cttgatttag gtgacactat agaatacaag 60
ctacttgttc tttttgcagg atccgccacc atgcccaaga agaagaggaa ggtgggtggt 120
tccggaggaa gccggccaat ggacaagaag tactccattg ggctcgctat cggcacaaac 180
agcgtcggct gggccgtcat tacggacgag tacaaggtgc cgagcaaaaa attcaaagtt 240
ctgggcaata ccgatcgcca cagcataaag aagaacctca ttggcgccct cctgttcgac 300
tccggggaga cggccgaagc cacgcggctc aaaagaacag cacggcgcag atatacccgc 360
agaaagaatc ggatctgcta cctgcaggag atctttagta atgagatggc taaggtggat 420
gactctttct tccataggct ggaggagtcc tttttggtgg aggaggataa aaagcacgag 480
cgccacccaa tctttggcaa tatcgtggac gaggtggcgt accatgaaaa gtacccaacc 540
atatatcatc tgaggaagaa gcttgtagac agtactgata aggctgactt gcggttgatc 600
tatctcgcgc tggcgcatat gatcaaattt cggggacact tcctcatcga gggggacctg 660
aacccagaca acagcgatgt cgacaaactc tttatccaac tggttcagac ttacaatcag 720
cttttcgaag agaacccgat caacgcatcc ggagttgacg ccaaagcaat cctgagcgct 780
aggctgtcca aatcccggcg gctcgaaaac ctcatcgcac agctccctgg ggagaagaag 840
aacggcctgt ttggtaatct tatcgccctg tcactcgggc tgacccccaa ctttaaatct 900
aacttcgacc tggccgaaga tgccaagctt caactgagca aagacaccta cgatgatgat 960
ctcgacaatc tgctggccca gatcggcgac cagtacgcag accttttttt ggcggcaaag 1020
aacctgtcag acgccattct gctgagtgat attctgcgag tgaacacgga gatcaccaaa 1080
gctccgctga gcgctagtat gatcaagcgc tatgatgagc accaccaaga cttgactttg 1140
ctgaaggccc ttgtcagaca gcaactgcct gagaagtaca aggaaatttt cttcgatcag 1200
tctaaaaatg gctacgccgg atacattgac ggcggagcaa gccaggagga attttacaaa 1260
tttattaagc ccatcttgga aaaaatggac ggcaccgagg agctgctggt aaagcttaac 1320
agagaagatc tgttgcgcaa acagcgcact ttcgacaatg gaagcatccc ccaccagatt 1380
cacctgggcg aactgcacgc tatcctcagg cggcaagagg atttctaccc ctttttgaaa 1440
gataacaggg aaaagattga gaaaatcctc acatttcgga taccctacta tgtaggcccc 1500
ctcgcccggg gaaattccag attcgcgtgg atgactcgca aatcagaaga gaccatcact 1560
ccctggaact tcgaggaagt cgtggataag ggggcctctg cccagtcctt catcgaaagg 1620
atgactaact ttgataaaaa tctgcctaac gaaaaggtgc ttcctaaaca ctctctgctg 1680
tacgagtact tcacagttta taacgagctc accaaggtca aatacgtcac agaagggatg 1740
agaaagccag cattcctgtc tggagagcag aagaaagcta tcgtggacct cctcttcaag 1800
acgaaccgga aagttaccgt gaaacagctc aaagaagact atttcaaaaa gattgaatgt 1860
ttcgactctg ttgaaatcag cggagtggag gatcgcttca acgcatccct gggaacgtat 1920
cacgatctcc tgaaaatcat taaagacaag gacttcctgg acaatgagga gaacgaggac 1980
attcttgagg acattgtcct caccctacg ttgtttgaag atagggagat gattgaagaa 2040

-continued

```
cgcttgaaaa cttacgctca tctcttcgac gacaaagtca tgaaacagct caagaggcgc   2100
cgatatacag gatgggggcg gctgtcaaga aaactgatca atgggatccg agacaagcag   2160
agtggaaaga caatcctgga ttttcttaag tccgatggat ttgccaacag gaacttcatg   2220
cagttgatcc atgatgactc tctcaccttt aaggaggaca tccagaaagc acaagtttct   2280
ggccaggggg acagtcttca cgagcacatc gctaatcttg caggtagccc agctatcaaa   2340
aagggaatac tgcagaccgt taaggtcgtg gatgaactcg tcaaagtaat gggaaggcat   2400
aagcccgaga atatcgttat cgagatggcc cgagagaacc aaactaccca gaagggacag   2460
aagaacagta gggaaaggat gaagaggatt gaagagggta taaaagaact ggggtcccaa   2520
atccttaagg aacacccagt tgaaaacacc cagcttcaga atgagaagct ctacctgtac   2580
tacctgcaga acggcaggga catgtacgtg gatcaggaac tggacatcaa tcggctctcc   2640
gactacgacg tggatgctat cgtgccccag tcttttctca aagatgattc tattgataat   2700
aaagtgttga caagatccga taaaaataga gggaagagtg ataacgtccc ctcagaagaa   2760
gttgtcaaga aaatgaaaaa ttattggcgg cagctgctga acgccaaact gatcacacaa   2820
cggaagttcg ataatctgac taaggctgaa cgaggtggcc tgtctgagtt ggataaagcc   2880
ggcttcatca aaaggcagct tgttgagaca cgccagatca ccaagcacgt ggcccaaatt   2940
ctcgattcac gcatgaacac caagtacgat gaaaatgaca aactgattcg agaggtgaaa   3000
gttattactc tgaagtctaa gctggtctca gatttcagaa aggactttca gttttataag   3060
gtgagagaga tcaacaatta ccaccatgcg catgatgcct acctgaatgc agtggtaggc   3120
actgcactta tcaaaaaata tcccaagctt gaatctgaat ttgtttacgg agactataaa   3180
gtgtacgatg ttaggaaaat gatcgcaaag tctgagcagg aaataggcaa ggccaccgct   3240
aagtacttct tttacagcaa tattatgaat tttttcaaga ccgagattac actggccaat   3300
ggagagattc ggaagcgacc acttatcgaa acaaacggag aaacaggaga aatcgtgtgg   3360
gacaagggta gggatttcgc gacagtccgg aaggtcctgt ccatgccgca ggtgaacatc   3420
gttaaaaaga ccgaagtaca gaccggaggc ttctccaagg aaagtatcct cccgaaaagg   3480
aacagcgaca agctgatcgc acgcaaaaaa gattgggacc ccaagaaata cggcggattc   3540
gattctccta cagtcgctta cagtgtactg gttgtggcca aagtggagaa agggaagtct   3600
aaaaaactca aaagcgtcaa ggaactgctg ggcatcacaa tcatggagcg atcaagcttc   3660
gaaaaaaacc ccatcgactt tctcgaggcg aaaggatata aagaggtcaa aaaagacctc   3720
atcattaagc ttcccaagta ctctctcttt gagcttgaaa acggccggaa acgaatgctc   3780
gctagtgcgg gcgagctgca gaaaggtaac gagctggcac tgccctctaa atacgttaat   3840
ttcttgtatc tggccagcca ctatgaaaag ctcaaagggt ctcccgaaga taatgagcag   3900
aagcagctgt tcgtggaaca acacaaacac taccttgatg agatcatcga gcaaataagc   3960
gaattctcca aaagagtgat cctcgccgac gctaacctcg ataaggtgct ttctgcttac   4020
aataagcaca gggataagcc catcagggag caggcagaaa acattatcca cttgtttact   4080
ctgaccaact tgggcgcgcc tgcagccttc aagtacttcg acaccaccat agacagaaag   4140
cggtacacct ctacaaagga ggtcctggac gccacactga ttcatcagtc aattacgggg   4200
ctctatgaaa caagaatcga cctctctcag ctcggtggag acggtggtag tggaggttca   4260
ggaggatccg gggggagcgg agggagcgct agcatggctc aggatttcaa agctggtgat   4320
ctgatttttg ctaagatgaa gggttatcca cactggcctg caaggattga tgagattcca   4380
```

-continued

```
gatggtgctg tcaaaccatc aaatataaaa tttcccatct tctttttttgg cactcatgaa   4440
acagcattcc tgggtcctaa agacatattc ccctatttga ccaataaaga caaatatggc   4500
aaacctaaca aaaggaaggg tttcaatgaa ggcttgtggg aaattgaaaa caatcctaaa   4560
gtggagctta atggacacaa ggtaaaaaag gttggagaag tttcaattaa agatttgagc   4620
agcaatgaag agggagatga tgagaagagg acaaagtcag ctcaaattgc tcacagtgag   4680
gggctggagg acgaggtgga cattgagaag gaagatggtg gtgacatgga cgtttctgat   4740
cagagacttg ttaaagatga agacctatca cagaaagatt cgacaaatgt cactgccaaa   4800
gctaaaagag gaaggaagag aaagagtgat gctgaacaag actctgatac agaaaattca   4860
agcccaactg caggcggttc cggtttagat ttcctatcaa caggtacatc aattatgtta   4920
ctgaagcgca gaggaaggaa atctaaaaca gagaagtcaa taatactaca acaacaggct   4980
tcaaaggaat taccaaggtc aggtaaagat ggaaagagag atgaaagaaa aggtgacaaa   5040
agaaaggagt ccacactgca gaagttgcac ggggagatta agacatcatt gaagattggt   5100
aatttagatg taaggaaatg tgtacatgca ttggatgagt taagctctct acatgttacc   5160
actcaacatc ttcagagaca tagtgaactc atagcaactc tgaaaaagat ctgcagattc   5220
aaatccagcc aggatgtgat ggacaaagct attatgctat ataataagtt taaaagtatg   5280
tttttaatgg gagaaggaga atcagtgcta agtcaggtgc tcaataaaag tctgactgaa   5340
cagaaactat ttgaagaagc caagagggga gtcctaaaaa acacagaaca aactaaagag   5400
cagaaagata ccaagatttt gaatgaagac ttcaactccg aagaggacgc tgagacagag   5460
aaggacaaat taggaggaaa catcttatct atggtgaaaa acaacatgac tgatcctgca   5520
gaagagtctg tctgactcga gcctctagaa ctatagtgag tcgtattacg tagatccaga   5580
catgataaga tacattgatg agtttggaca aaccacaact agaatgcagt gaaaaaaatg   5640
ctttatttgt gaaatttgtg atgctattgc tttatttgta accattataa gctgcaataa   5700
acaagttaac aacaacaatt gcattcattt tatgtttcag gttcaggggg aggtgtggga   5760
ggttttttaa ttcgcggccg cggcgccaat gcattgggcc cggtacccag cttttgttcc   5820
ctttagtgag ggttaattgc gcgcttggcg taatcatggt catagctgtt tcctgtgtga   5880
aattgttatc cgctcacaat tccacacaac atacgagccg gaagcataaa gtgtaaagcc   5940
tggggtgcct aatgagtgag ctaactcaca ttaattgcgt tgcgctcact gcccgctttc   6000
cagtcgggaa acctgtcgtg ccagctgcat taatgaatcg gccaacgcgc ggggagaggc   6060
ggtttgcgta ttgggcgctc ttccgcttcc tcgctcactg actcgctgcg ctcggtcgtt   6120
cggctgcggc gagcggtatc agctcactca aaggcggtaa tacggttatc cacagaatca   6180
ggggataacg caggaaagaa catgtgagca aaaggccagc aaaaggccag gaaccgtaaa   6240
aaggccgcgt tgctggcgtt tttccatagg ctccgccccc ctgacgagca tcacaaaaat   6300
cgacgctcaa gtcagaggtg gcgaaacccg acaggactat aaagatacca ggcgtttccc   6360
cctggaagct ccctcgtgcg ctctcctgtt ccgaccctgc cgcttaccgg atacctgtcc   6420
gcctttctcc cttcgggaag cgtggcgctt tctcatagct cacgctgtag gtatctcagt   6480
tcggtgtagg tcgttcgctc caagctgggc tgtgtgcacg aaccccccgt tcagcccgac   6540
cgctgcgcct tatccggtaa ctatcgtctt gagtccaacc cggtaagaca cgacttatcg   6600
ccactggcag cagccactgg taacaggatt agcagagcga ggtatgtagg cggtgctaca   6660
gagttcttga agtggtggcc taactacggc tacactagaa ggacagtatt tggtatctgc   6720
gctctgctga agccagttac cttcggaaaa agagttggta gctcttgatc cggcaaacaa   6780
```

-continued

```
accaccgctg gtagcggtgg tttttttgtt tgcaagcagc agattacgcg cagaaaaaaa   6840
ggatctcaag aagatccttt gatcttttct acggggtctg acgctcagtg gaacgaaaac   6900
tcacgttaag ggattttggt catgagatta tcaaaaagga tcttcaccta gatcctttta   6960
aattaaaaat gaagttttaa atcaatctaa agtatatatg agtaaacttg gtctgacagt   7020
taccaatgct taatcagtga ggcacctatc tcagcgatct gtctatttcg ttcatccata   7080
gttgcctgac tccccgtcgt gtagataact acgatacggg agggcttacc atctggcccc   7140
agtgctgcaa tgataccgcg agacccacgc tcaccggctc cagatttatc agcaataaac   7200
cagccagccg gaagggccga gcgcagaagt ggtcctgcaa ctttatccgc ctccatccag   7260
tctattaatt gttgccggga agctagagta agtagttcgc cagttaatag tttgcgcaac   7320
gttgttgcca ttgctacagg catcgtggtg tcacgctcgt cgtttggtat ggcttcattc   7380
agctccggtt cccaacgatc aaggcgagtt acatgatccc ccatgttgtg caaaaaagcg   7440
gttagctcct tcggtcctcc gatcgttgtc agaagtaagt tggccgcagt gttatcactc   7500
atggttatgg cagcactgca taattctctt actgtcatgc catccgtaag atgcttttct   7560
gtgactggtg agtactcaac caagtcattc tgagaatagt gtatgcggcg accgagttgc   7620
tcttgcccgg cgtcaatacg ggataatacc gcgccacata gcagaacttt aaaagtgctc   7680
atcattggaa aacgttcttc ggggcgaaaa ctctcaagga tcttaccgct gttgagatcc   7740
agttcgatgt aacccactcg tgcacccaac tgatcttcag catcttttac tttcaccagc   7800
gtttctgggt gagcaaaaac aggaaggcaa aatgccgcaa aaaagggaat aagggcgaca   7860
cggaaatgtt gaatactcat actcttcctt tttcaatatt attgaagcat ttatcagggt   7920
tattgtctca tgagcggata catatttgaa tgtatttaga aaaataaaca aataggggtt   7980
ccgcgcacat ttccccgaaa agtgccacct aaattgtaag cgttaatatt ttgttaaaat   8040
tcgcgttaaa tttttgttaa atcagctcat tttttaacca ataggccgaa atcggcaaaa   8100
tcccttataa atcaaaagaa tagaccgaga tagggttgag tgttgttcca gtttggaaca   8160
agagtccact attaaagaac gtggactcca acgtcaaagg gcgaaaaacc gtctatcagg   8220
gcgatggccc actacgtgaa ccatcaccct aatcaagttt tttggggtcg aggtgccgta   8280
aagcactaaa tcggaaccct aaagggagcc cccgatttag agcttgacgg ggaaagccgg   8340
cgaacgtggc gagaaaggaa gggaagaaag cgaaaggagc gggcgctagg gcgctggcaa   8400
gtgtagcggt cacgctgcgc gtaaccacca cacccgccgc gcttaatgcg ccgctacagg   8460
gcgcgtccca ttcgccattc aggctgcgca actgttggga agggcgatcg gtgcgggcct   8520
cttcgctatt acgccagtcg accatagcca attcaatatg gcgtatatgg actcatgcca   8580
attcaatatg gtggatctgg acctgtgcca attcaatatg gcgtatatgg actcgtgcca   8640
attcaatatg gtggatctgg accccagcca attcaatatg gcggacttgg caccatgcca   8700
attcaatatg gcggacttgg cactgtgcca actggggagg ggtctacttg gcacggtgcc   8760
aagtttgagg aggggtcttg gccctgtgcc aagtccgcca tattgaattg gcatggtgcc   8820
aataatggcg gccatattgg ctatatgcca ggatcaatat ataggcaata tccaatatgg   8880
ccctatgcca atatggctat tggccaggtt caatactatg tattggccct atgccatata   8940
gtattccata tatgggtttt cctattgacg tagatagccc ctcccaatgg gcggtcccat   9000
ataccatata tggggcttcc taataccgcc catagccact cccccattga cgtcaatggt   9060
ctctatatat ggtctttcct attgacgtca tatgggcggt cctattgacg tatatggcgc   9120
```

ctcccccatt gacgtcaatt acggtaaatg gcccgcctgg ctcaatgccc attgacgtca 9180
ataggaccac ccaccattga cgtcaatggg atggctcatt gcccattcat atccgttctc 9240
acgcccccta ttgacgtcaa tgacggtaaa tggcccactt ggcagtacat caatatctat 9300
taatagtaac ttggcaagta cattactatt ggaaggacgc cagggtacat tggcagtact 9360
cccattgacg tcaatggcgg taaatggccc gcgatggctg ccaagtacat ccccattgac 9420
gtcaatgggg aggggcaatg acgcaaatgg gcgttccatt gacgtaaatg ggcggtaggc 9480
gtgcctaatg ggaggtctat ataagcaatg ctcgtttagg gaac 9524

<210> SEQ ID NO 9
<211> LENGTH: 9560
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9
cgccattctg cctggggacg tcggagcaag cttgatttag gtgacactat agaatacaag 60
ctacttgttc tttttgcagg atccgccacc atggctcagg atttcaaagc tggtgatctg 120
atttttgcta agatgaaggg ttatccacac tggcctgcaa ggattgatga gattccagat 180
ggtgctgtca aaccatcaaa tataaaattt cccatcttct tttttggcac tcatgaaaca 240
gcattcctgg gtcctaaaga catattcccc tatttgacca ataaagacaa atatggcaaa 300
cctaacaaaa ggaagggttt caatgaaggc ttgtgggaaa ttgaaaacaa tcctaaagtg 360
gagcttaatg gacacaaggt aaaaaaggtt ggagaagttt caattaaaga tttgagcagc 420
aatgaagagg gagatgatga gaagaggaca aagtcagctc aaattgctca cagtgagggg 480
ctggaggacg aggtggacat tgagaaggaa gatggtggtg acatggacgt ttctgatcag 540
agacttgtta aagatgaaga cctatcacag aaagattcga caaatgtcac tgccaaagct 600
aaaagaggaa ggaagagaaa gagtgatgct gaacaagact ctgatacaga aaattcaagc 660
ccaactgcag gcggttccgg tttagatttc ctatcaacag gtacatcaat tatgttactg 720
aagcgcagag gaaggaaatc taaaacagag aagtcaataa tactacaaca acaggcttca 780
aaggaattac caaggtcagg taaagatgga aagagagatg aaagaaaagg tgacaaaaga 840
aaggagtcca cactgcagaa gttgcacggg gagattaaga catcattgaa gattggtaat 900
ttagatgtaa ggaaatgtgt acatgcattg gatgagttaa gctctctaca tgttaccact 960
caacatcttc agagacatag tgaactcata gcaactctga aaaagatctg cagattcaaa 1020
tccagccagg atgtgatgga caaagctatt atgctatata ataagtttaa aagtatgttt 1080
ttaatgggag aaggagaatc agtgctaagt caggtgctca ataaaagtct gactgaacag 1140
aaactatttg aagaagccaa gaggggagtc ctaaaaaaca cagaacaaac taaagagcag 1200
aaagatacca agattttgaa tgaagacttc aactccgaag aggacgctga gacagagaag 1260
gacaaattag gaggaaacat cttatctatg gtgaaaaaca acatgactaa tcctgcagaa 1320
gagtctgtcg gtggtagtgg aggttcagga ggatccgggg ggagcggagg gagccggcca 1380
atggacaaga agtactccat tgggctcgct atcggcacaa acagcgtcgg ctgggccgtc 1440
attacggacg agtacaaggt gccgagcaaa aaattcaaag ttctgggcaa taccgatcgc 1500
cacagcataa agaagaacct cattggcgcc ctcctgttcg actccgggga gacggccgaa 1560
gccacgcggc tcaaaagaac agcacggcgc agatataccc gcagaaagaa tcggatctgc 1620

-continued

```
tacctgcagg agatctttag taatgagatg gctaaggtgg atgactcttt cttccatagg   1680
ctggaggagt cctttttggt ggaggaggat aaaaagcacg agcgccaccc aatctttggc   1740
aatatcgtgg acgaggtggc gtaccatgaa aagtacccaa ccatatatca tctgaggaag   1800
aagcttgtag acagtactga taaggctgac ttgcggttga tctatctcgc gctggcgcat   1860
atgatcaaat ttcggggaca cttcctcatc gaggggggacc tgaacccaga caacagcgat   1920
gtcgacaaac tctttatcca actggttcag acttacaatc agcttttcga agagaacccg   1980
atcaacgcat ccggagttga cgccaaagca atcctgagcg ctaggctgtc caaatcccgg   2040
cggctcgaaa acctcatcgc acagctccct ggggagaaga agaacggcct gtttggtaat   2100
cttatcgccc tgtcactcgg gctgaccccc aactttaaat ctaacttcga cctggccgaa   2160
gatgccaagc ttcaactgag caaagacacc tacgatgatg atctcgacaa tctgctggcc   2220
cagatcggcg accagtacgc agaccttttt ttggcggcaa agaacctgtc agacgccatt   2280
ctgctgagtg atattctgcg agtgaacacg gagatcacca aagctccgct gagcgctagt   2340
atgatcaagc gctatgatga gcaccaccaa gacttgactt tgctgaaggc ccttgtcaga   2400
cagcaactgc ctgagaagta caaggaaatt ttcttcgatc agtctaaaaa tggctacgcc   2460
ggatacattg acggcggagc aagccaggag gaattttaca aatttattaa gcccatcttg   2520
gaaaaaatgg acggcaccga ggagctgctg gtaaagctta acagagaaga tctgttgcgc   2580
aaacagcgca ctttcgacaa tggaagcatc cccccaccaga ttcacctggg cgaactgcac   2640
gctatcctca ggcggcaaga ggatttctac cccttttttga aagataacag ggaaaagatt   2700
gagaaaatcc tcacatttcg gataccctac tatgtaggcc ccctcgcccg gggaaattcc   2760
agattcgcgt ggatgactcg caaatcagaa gagaccatca ctccctggaa cttcgaggaa   2820
gtcgtggata agggggcctc tgcccagtcc ttcatcgaaa ggatgactaa ctttgataaa   2880
aatctgccta acgaaaaggt gcttcctaaa cactctctgc tgtacgagta cttcacagtt   2940
tataacgagc tcaccaaggt caaatacgtc acagaaggga tgagaaagcc agcattcctg   3000
tctggagagc agaagaaagc tatcgtggac ctcctcttca agacgaaccg gaaagttacc   3060
gtgaaacagc tcaaagaaga ctatttcaaa aagattgaat gtttcgactc tgttgaaatc   3120
agcggagtgg aggatcgctt caacgcatcc ctgggaacgt atcacgatct cctgaaaatc   3180
attaaagaca aggacttcct ggacaatgag gagaacgagg acattcttga ggacattgtc   3240
ctcaccctta cgttgtttga agatagggag atgattgaag aacgcttgaa aacttacgct   3300
catctcttcg acgacaaagt catgaaacag ctcaagaggc gccgatatac aggatggggg   3360
cggctgtcaa gaaaactgat caatgggatc cgagacaagc agagtggaaa gacaatcctg   3420
gattttctta agtccgatgg atttgccaac aggaacttca tgcagttgat ccatgatgac   3480
tctctcacct ttaaggagga catccagaaa gcacaagttt ctggccaggg ggacagtctt   3540
cacgagcaca tcgctaatct tgcaggtagc ccagctatca aaaagggaat actgcagacc   3600
gttaaggtcg tggatgaact cgtcaaagta atgggaaggc ataagcccga gaatatcgtt   3660
atcgagatgg cccgagagaa ccaaactacc cagaagggac agaagaacag tagggaaagg   3720
atgaagagga ttgaagaggg tataaaagaa ctggggtccc aaatccttaa ggaacaccca   3780
gttgaaaaca cccagcttca gaatgagaag ctctacctgt actacctgca gaacggcagg   3840
gacatgtacg tggatcagga actggacatc aatcggctct ccgactacga cgtggatgct   3900
atcgtgcccc agtcttttct caaagatgat tctattgata ataaagtgtt gacaagatcc   3960
gataaaaata gagggaagag tgataacgtc ccctcagaag aagttgtcaa gaaaatgaaa   4020
```

-continued aattattggc ggcagctgct gaacgccaaa ctgatcacac aacggaagtt cgataatctg 4080
actaaggctg aacgaggtgg cctgtctgag ttggataaag ccggcttcat caaaaggcag 4140
cttgttgaga cacgccagat caccaagcac gtggcccaaa ttctcgattc acgcatgaac 4200
accaagtacg atgaaaatga caaactgatt cgagaggtga aagttattac tctgaagtct 4260
aagctggtct cagatttcag aaaggacttt cagttttata aggtgagaga gatcaacaat 4320
taccaccatg cgcatgatgc ctacctgaat gcagtggtag gcactgcact tatcaaaaaa 4380
tatcccaagc ttgaatctga atttgtttac ggagactata aagtgtacga tgttaggaaa 4440
atgatcgcaa agtctgagca ggaaataggc aaggccaccg ctaagtactt cttttacagc 4500
aatattatga atttttcaa gaccgagatt acactggcca atggagagat tcggaagcga 4560
ccacttatcg aaacaaacgg agaaacagga gaaatcgtgt gggacaaggg tagggatttc 4620
gcgacagtcc ggaaggtcct gtccatgccg caggtgaaca tcgttaaaaa gaccgaagta 4680
cagaccggag gcttctccaa ggaaagtatc ctcccgaaaa ggaacagcga caagctgatc 4740
gcacgcaaaa aagattggga ccccaagaaa tacggcggat tcgattctcc tacagtcgct 4800
tacagtgtac tggttgtggc caaagtggag aaagggaagt ctaaaaaact caaaagcgtc 4860
aaggaactgc tgggcatcac aatcatggag cgatcaagct tcgaaaaaaa ccccatcgac 4920
tttctcgagg cgaaaggata taaagaggtc aaaaaagacc tcatcattaa gcttcccaag 4980
tactctctct ttgagcttga aaacggccgg aaacgaatgc tcgctagtgc gggcgagctg 5040
cagaaaggta acgagctggc actgccctct aaatacgtta atttcttgta tctggccagc 5100
cactatgaaa agctcaaagg gtctcccgaa gataatgagc agaagcagct gttcgtggaa 5160
caacacaaac actaccttga tgagatcatc gagcaaataa gcgaattctc caaaagagtg 5220
atcctcgccg acgctaacct cgataaggtg ctttctgctt acaataagca cagggataag 5280
cccatcaggg agcaggcaga aaacattatc cacttgttta ctctgaccaa cttgggcgcg 5340
cctgcagcct tcaagtactt cgacaccacc atagacagaa agcggtacac ctctacaaag 5400
gaggtcctgg acgccacact gattcatcag tcaattacgg ggctctatga aacaagaatc 5460
gacctctctc agctcggtgg agacggtggt agtggaggtt caggaggatc cggggggagc 5520
ggagggagcg ctagcatgcc caagaagaag aggaaggtgg gtggttccta gctcgagcct 5580
ctagaactat agtgagtcgt attacgtaga tccagacatg ataagataca ttgatgagtt 5640
tggacaaacc acaactagaa tgcagtgaaa aaaatgcttt atttgtgaaa tttgtgatgc 5700
tattgcttta tttgtaacca ttataagctg caataaacaa gttaacaaca acaattgcat 5760
tcattttatg tttcaggttc agggggaggt gtgggaggtt ttttaattcg cggccgcggc 5820
gccaatgcat tgggcccggt acccagcttt tgttcccttt agtgagggtt aattgcgcgc 5880
ttggcgtaat catggtcata gctgtttcct gtgtgaaatt gttatccgct cacaattcca 5940
cacaacatac gagccggaag cataaagtgt aaagcctggg gtgcctaatg agtgagctaa 6000
ctcacattaa ttgcgttgcg ctcactgccc gctttccagt cgggaaacct gtcgtgccag 6060
ctgcattaat gaatcggcca acgcgcgggg agaggcggtt tgcgtattgg gcgctcttcc 6120
gcttcctcgc tcactgactc gctgcgctcg gtcgttcggc tgcggcgagc ggtatcagct 6180
cactcaaagg cggtaatacg gttatccaca gaatcagggg ataacgcagg aaagaacatg 6240
tgagcaaaag gccagcaaaa ggccaggaac cgtaaaaagg ccgcgttgct ggcgtttttc 6300
cataggctcc gcccccctga cgagcatcac aaaaatcgac gctcaagtca gaggtggcga 6360

-continued

```
aacccgacag gactataaag ataccaggcg tttccccctg gaagctccct cgtgcgctct   6420
cctgttccga ccctgccgct taccggatac ctgtccgcct ttctcccttc gggaagcgtg   6480
gcgctttctc atagctcacg ctgtaggtat ctcagttcgg tgtaggtcgt tcgctccaag   6540
ctgggctgtg tgcacgaacc ccccgttcag cccgaccgct gcgccttatc cggtaactat   6600
cgtcttgagt ccaacccggt aagacacgac ttatcgccac tggcagcagc cactggtaac   6660
aggattagca gagcgaggta tgtaggcggt gctacagagt tcttgaagtg gtggcctaac   6720
tacggctaca ctagaaggac agtatttggt atctgcgctc tgctgaagcc agttaccttc   6780
ggaaaaagag ttggtagctc ttgatccggc aaacaaacca ccgctggtag cggtggtttt   6840
tttgtttgca agcagcagat tacgcgcaga aaaaaaggat ctcaagaaga tcctttgatc   6900
ttttctacgg ggtctgacgc tcagtggaac gaaaactcac gttaagggat tttggtcatg   6960
agattatcaa aaaggatctt cacctagatc cttttaaatt aaaaatgaag ttttaaatca   7020
atctaaagta tatatgagta aacttggtct gacagttacc aatgcttaat cagtgaggca   7080
cctatctcag cgatctgtct atttcgttca tccatagttg cctgactccc cgtcgtgtag   7140
ataactacga tacgggaggg cttaccatct ggccccagtg ctgcaatgat accgcgagac   7200
ccacgctcac cggctccaga tttatcagca ataaaccagc cagccggaag ggccgagcgc   7260
agaagtggtc ctgcaacttt atccgcctcc atccagtcta ttaattgttg ccgggaagct   7320
agagtaagta gttcgccagt taatagtttg cgcaacgttg ttgccattgc tacaggcatc   7380
gtggtgtcac gctcgtcgtt tggtatggct tcattcagct ccggttccca acgatcaagg   7440
cgagttacat gatcccccat gttgtgcaaa aaagcggtta gctccttcgg tcctccgatc   7500
gttgtcagaa gtaagttggc cgcagtgtta tcactcatgg ttatggcagc actgcataat   7560
tctcttactg tcatgccatc cgtaagatgc ttttctgtga ctggtgagta ctcaaccaag   7620
tcattctgag aatagtgtat gcggcgaccg agttgctctt gcccggcgtc aatacgggat   7680
aataccgcgc cacatagcag aactttaaaa gtgctcatca ttggaaaacg ttcttcgggg   7740
cgaaaactct caaggatctt accgctgttg agatccagtt cgatgtaacc cactcgtgca   7800
cccaactgat cttcagcatc ttttactttc accagcgttt ctgggtgagc aaaaacagga   7860
aggcaaaatg ccgcaaaaaa gggaataagg gcgacacgga aatgttgaat actcatactc   7920
ttcctttttc aatattattg aagcatttat cagggttatt gtctcatgag cggatacata   7980
tttgaatgta tttagaaaaa taaacaaata ggggttccgc gcacatttcc ccgaaaagtg   8040
ccacctaaat tgtaagcgtt aatattttgt taaaattcgc gttaaatttt tgttaaatca   8100
gctcattttt taaccaatag gccgaaatcg gcaaaatccc ttataaatca aaagaataga   8160
ccgagatagg gttgagtgtt gttccagttt ggaacaagag tccactatta aagaacgtgg   8220
actccaacgt caaagggcga aaaaccgtct atcagggcga tggcccacta cgtgaaccat   8280
caccctaatc aagttttttg gggtcgaggt gccgtaaagc actaaatcgg aaccctaaag   8340
ggagcccccg atttagagct tgacggggaa agccggcgaa cgtggcgaga aaggaaggga   8400
agaaagcgaa aggagcgggc gctagggcgc tggcaagtgt agcggtcacg ctgcgcgtaa   8460
ccaccacacc cgccgcgctt aatgcgccgc tacagggcgc gtcccattcg ccattcaggc   8520
tgcgcaactg ttgggaaggg cgatcggtgc gggcctcttc gctattacgc cagtcgacca   8580
tagccaattc aatatggcgt atatggactc atgccaattc aatatggtgg atctggacct   8640
gtgccaattc aatatggcgt atatggactc gtgccaattc aatatggtgg atctggaccc   8700
cagccaattc aatatggcgg acttggcacc atgccaattc aatatggcgg acttggcact   8760
```

```
gtgccaactg gggaggggtc tacttggcac ggtgccaagt ttgaggaggg gtcttggccc   8820

tgtgccaagt ccgccatatt gaattggcat ggtgccaata atggcggcca tattggctat   8880

atgccaggat caatatatag gcaatatcca atatggccct atgccaatat ggctattggc   8940

caggttcaat actatgtatt ggccctatgc catatagtat tccatatatg ggttttccta   9000

ttgacgtaga tagcccctcc caatgggcgg tcccatatac catatatggg gcttcctaat   9060

accgcccata gccactcccc cattgacgtc aatggtctct atatatggtc tttcctattg   9120

acgtcatatg ggcggtccta ttgacgtata tggcgcctcc cccattgacg tcaattacgg   9180

taaatggccc gcctggctca atgcccattg acgtcaatag gaccacccac cattgacgtc   9240

aatgggatgg ctcattgccc attcatatcc gttctcacgc cccctattga cgtcaatgac   9300

ggtaaatggc ccacttggca gtacatcaat atctattaat agtaacttgg caagtacatt   9360

actattggaa ggacgccagg gtacattggc agtactccca ttgacgtcaa tggcggtaaa   9420

tggcccgcga tggctgccaa gtacatcccc attgacgtca atggggaggg gcaatgacgc   9480

aaatgggcgt tccattgacg taaatgggcg gtaggcgtgc ctaatgggag gtctatataa   9540

gcaatgctcg tttagggaac                                               9560
```

<210> SEQ ID NO 10
<211> LENGTH: 6288
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
tatagtgagt cgtattacaa ttcactggcc gtcgttttac aacgtcgtga ctgggaaaac     60

cctggcgtta cccaacttaa tcgccttgca gcacatcccc ctttcgccag ctggcgtaat    120

agcgaagagg cccgcaccga tcgcccttcc caacagttgc gcagcctgaa tggcgaatgg    180

acgcgccctg tagcggcgca ttaagcgcgg cgggtgtggt ggttacgcgc agcgtgaccg    240

ctacacttgc cagcgcccta gcgcccgctc ctttcgcttt cttcccttcc tttctcgcca    300

cgttcgccgg ctttccccgt caagctctaa atcgggggct ccctttaggg ttccgattta    360

gtgctttacg gcacctcgac cccaaaaaac ttgattaggg tgatggttca cgtagtgggc    420

catcgccctg atagacggtt tttcgccctt tgacgttgga gtccacgttc tttaatagtg    480

gactcttgtt ccaaactgga acaacactca accctatctc ggtctattct tttgatttat    540

aagggatttt gccgatttcg gcctattggt taaaaaatga gctgatttaa caaaaattta    600

acgcgaattt taacaaaata ttaacgctta caatttcctg atgcggtatt ttctccttac    660

gcatctgtgc ggtatttcac accgcatcag gtggcacttt tcggggaaat gtgcgcggaa    720

cccctatttg tttatttttc taaatacatt caaatatgta tccgctcatg agacaataac    780

cctgataaat gcttcaataa tattgaaaaa ggaagagtat gagtattcaa catttccgtg    840

tcgcccttat tccctttttt gcggcatttt gccttcctgt ttttgctcac ccagaaacgc    900

tggtgaaagt aaaagatgct gaagatcagt tgggtgcacg agtgggttac atcgaactgg    960

atctcaacag cggtaagatc cttgagagtt ttcgccccga agaacgtttt ccaatgatga   1020

gcacttttaa agttctgcta tgtggcgcgg tattatcccg tattgacgcc gggcaagagc   1080

aactcggtcg ccgcatacac tattctcaga atgacttggt tgagtactca ccagtcacag   1140

aaaagcatct tacggatggc atgacagtaa gagaattatg cagtgctgcc ataaccatga   1200
```

-continued

```
gtgataacac tgcggccaac ttacttctga caacgatcgg aggaccgaag gagctaaccg   1260
ctttttttgca caacatgggg gatcatgtaa ctcgccttga tcgttgggaa ccggagctga   1320
atgaagccat accaaacgac gagcgtgaca ccacgatgcc tgtagcaatg gcaacaacgt   1380
tgcgcaaact attaactggc gaactactta ctctagcttc ccggcaacaa ttaatagact   1440
ggatggaggc ggataaagtt gcaggaccac ttctgcgctc ggcccttccg gctggctggt   1500
ttattgctga taaatctgga gccggtgagc gtgggtctcg cggtatcatt gcagcactgg   1560
ggccagatgg taagccctcc cgtatcgtag ttatctacac gacggggagt caggcaacta   1620
tggatgaacg aaatagacag atcgctgaga taggtgcctc actgattaag cattggtaac   1680
tgtcagacca agtttactca tatatacttt agattgattt aaaacttcat ttttaattta   1740
aaaggatcta ggtgaagatc ctttttgata atctcatgac caaaatccct taacgtgagt   1800
tttcgttcca ctgagcgtca gaccccgtag aaaagatcaa aggatcttct tgagatcctt   1860
tttttctgcg cgtaatctgc tgcttgcaaa caaaaaaacc accgctacca gcggtggttt   1920
gtttgccgga tcaagagcta ccaactcttt ttccgaaggt aactggcttc agcagagcgc   1980
agataccaaa tactgttctt ctagtgtagc cgtagttagg ccaccacttc aagaactctg   2040
tagcaccgcc tacatacctc gctctgctaa tcctgttacc agtggctgct gccagtggcg   2100
ataagtcgtg tcttaccggg ttggactcaa gacgatagtt accggataag gcgcagcggt   2160
cgggctgaac ggggggttcg tgcacacagc ccagcttgga gcgaacgacc tacaccgaac   2220
tgagatacct acagcgtgag ctatgagaaa gcgccacgct tcccgaaggg agaaaggcgg   2280
acaggtatcc ggtaagcggc agggtcggaa caggagagcg cacgagggag cttccagggg   2340
gaaacgcctg gtatctttat agtcctgtcg ggtttcgcca cctctgactt gagcgtcgat   2400
ttttgtgatg ctcgtcaggg gggcggagcc tatggaaaaa cgccagcaac gcggcctttt   2460
tacggttcct ggccttttgc tggccttttg ctcacatgtt ctttcctgcg ttatcccctg   2520
attctgtgga taaccgtatt accgcctttg agtgagctga taccgctcgc cgcagccgaa   2580
cgaccgagcg cagcgagtca gtgagcgagg aagcggaaga gcgcccaata cgcaaaccgc   2640
ctctccccgc gcgttggccg attcattaat gcagctggca cgacaggttt cccgactgga   2700
aagcgggcag tgagcgcaac gcaattaatg tgagttagct cactcattag gcaccccagg   2760
ctttacactt tatgcttccg gctcgtatgt tgtgtggaat tgtgagcgga taacaatttc   2820
acacaggaaa cagctatgac catgattacg ccaagctatt taggtgacac tatagaatac   2880
tcaagctatg catccaacgc gttgggagct ctcccatatg tatactgggt ctctctggtt   2940
agaccagatc tgagcctggg agctctctgg ctaactaggg aacccactgc ttaagcctca   3000
ataaagcttg ccttgagtgc ttcaagtagt gtgtgcccgt ctgttgtgtg actctggtaa   3060
ctagagatcc ctcagaccct tttagtcagt gtggaaaatc tctagcatag ggataacagg   3120
gtaatctcga gttgacgtca ggaaacagct atgaccatga ttacgccaag ctatcaactt   3180
tgtatagaaa agttgaaggc ctcttcgcta ttacgccagt cgaccgccaa ttcaatatgg   3240
cgtatatgga ctcatgccaa ttcaatatgg tggatctgga cctgtgccaa ttcaatatgg   3300
cgtatatgga ctcgtgccaa ttcaatatgg tggatctgga ccccagccaa ttcaatatgg   3360
cggacttggc accatgccaa ttcaatatgg cggacctggc actgtgccaa ctggggaggg   3420
gtctacttgg cacggtgcca agtttgagga ggggtcttgg ccctgtgcca agtccgccat   3480
attgaattgg catggtgcca ataatggcgg ccatattggc tatatgccag gatcaatata   3540
```

-continued

```
taggcaatat ccaatatggc cctatgccaa tatggctatt ggccaggttc aatactatgt   3600

attggcccta tgccatatag tattccatat atgggttttc ctattgacgt agatagcccc   3660

tcccaatggg cggtcccata taccatatat ggggcttcct aataccgccc atagccactc   3720

ccccattgac gtcaatggtc tctatatatg gtctttccta ttgacgtcat atgggcggtc   3780

ctattgacgt atatggcgcc tcccccattg acgtcaatta cggtaaatgg cccgcctggc   3840

tcaatgccca ttgacgtcaa taggaccacc caccattgac gtcaatggga tggctcattg   3900

cccattcata tccgttctca cgccccctat tgacgtcaat gacggtaaat ggcccacttg   3960

gcagtacatc aatatctatt aatagtaact tggcaagtac attactattg gaagtacgcc   4020

agggtacatt ggcagtactc ccattgacgt caatggcggt aaatggcccg cgatggctgc   4080

caagtacatc cccattgacg tcaatgggga ggggcaatga cgcaaatggg cgttccattg   4140

acgtaaatgg gcggtaggcg tgcctaatgg gaggtctata taagcaatgc tcgtttaggg   4200

aaccgccatt ctgcctgggg acgtcggagc aagcttgatt taggtgacac tatagaaagt   4260

ttgtacaaaa aagcaggctt ggtgagcaag ggcgaggagg tcatcaaaga gttcatgcgc   4320

ttcaaggtgc gcatggaggg ctccatgaac ggccacgagt tcgagatcga gggcgagggc   4380

gagggccgcc cctacgaggg cacccagacc gccaagctga aggtgaccaa gggcggcccc   4440

ctgcccttcg cctgggacat cctgtccccc cagttcatgt acggctccaa ggcgtacgtg   4500

aagcaccccg ccgacatccc cgattacaag aagctgtcct tccccgaggg cttcaagtgg   4560

gagcgcgtga tgaacttcga ggacggcggt ctggtgaccg tgacccagga ctcctccctg   4620

caggacggca cgctgatcta caaggtgaag atgcgcggca ccaacttccc ccccgacggc   4680

cccgtaatgc agaagaagac catgggctgg gaggcctcca ccgagcgcct gtaccccccgc  4740

gacggcgtgc tgaagggcga gatccaccag gccctgaagc tgaaggacgg cggccactac   4800

ctggtggagt tcaagaccat ctacatggcc aagaagcccg tgcaactgcc cggctactac   4860

tacgtggaca ccaagctgga catcacctcc cacaacgagg actacaccat cgtggaacag   4920

tacgagcgct ccgagggccg ccaccacctg ttcctggggc atggcaccgg cagcaccggc   4980

agcggcagct ccggcaccgc ctcctccgag gacaacaaca tggccgtcat caaagagttc   5040

atgcgcttca aggtgcgcat ggagggctcc atgaacggcc acgagttcga gatcgagggc   5100

gagggcgagg gccgccccta cgagggcacc cagaccgcca agctgaaggt gaccaagggc   5160

ggcccccctgc ccttcgcctg ggacatcctg tccccccagt tcatgtacgg ctccaaggcg  5220

tacgtgaagc accccgccga catccccgat tacaagaagc tgtccttccc cgagggcttc   5280

aagtgggagc gcgtgatgaa cttcgaggac ggcggtctgg tgaccgtgac ccaggactcc   5340

tccctgcagg acggcacgct gatctacaag gtgaagatgc gcggcaccaa cttccccccc   5400

gacggccccg taatgcagaa gaagaccatg ggctgggagg cctccaccga gcgcctgtac   5460

ccccgcgacg gcgtgctgaa gggcgagatc caccaggccc tgaagctgaa ggacggcggc   5520

cactacctgg tggagttcaa gaccatctac atggccaaga agcccgtgca actgcccggc   5580

tactactacg tggacaccaa gctggacatc acctcccaca acgaggacta caccatcgtg   5640

gaacagtacg agcgctccga gggccgccac cacctgttcc tgtacggcat ggacgagctg   5700

tacaagtaac acccagcttt cttgtacaaa gtggtgtacc atcgatgatg atccagacat   5760

gataagatac attgatgagt ttggacaaac cacaactaga atgcagtgaa aaaaatgctt   5820

tatttgtgaa atttgtgatg ctattgcttt atttgtaacc attataagct gcaataaaca   5880

agttaacaac aacaattgca ttcattttat gtttcaggtt cagggggagg tgtgggaggt   5940
```

tttttaaagc aagtaaaacc tctacaaatg tggtatggct gattatgatc ctctagatcg 6000
tgcatgcttc cgcggattac cctgttatcc ctatggaagg gctaattcac tcccaacgaa 6060
gacaagatct gctttttgct tgtactgggt ctctctggtt agaccagatc tgagcctggg 6120
agctctctgg ctaactaggg aacccactgc ttaagcctca ataaagcttg ccttgagtgc 6180
ttcaagtagt gtgtgcccgt ctgttgtgtg actctggtaa ctagagatcc ctcagaccct 6240
tttagtcagt gtggaaaatc tctagcagta tacgggccca attcgccc 6288

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 11
gtaggtcagg gtggtcacga ggg 23

<210> SEQ ID NO 12
<211> LENGTH: 13
<212> TYPE: PRT
<213> ORGANISM: Human immunodeficiency virus 1

<400> SEQUENCE: 12

Ile Ile Gly Gln Val Arg Asp Gln Ala Glu His Leu Lys
1 5 10

<210> SEQ ID NO 13
<211> LENGTH: 7
<212> TYPE: PRT
<213> ORGANISM: Simian virus 40

<400> SEQUENCE: 13

Pro Lys Lys Lys Arg Lys Val
1 5

<210> SEQ ID NO 14
<211> LENGTH: 9
<212> TYPE: PRT
<213> ORGANISM: Unknown
<220> FEATURE:
<223> OTHER INFORMATION: Description of Unknown: c-myc nuclear localization signal sequence

<400> SEQUENCE: 14

Pro Ala Ala Lys Arg Val Lys Leu Asp
1 5

<210> SEQ ID NO 15
<211> LENGTH: 10
<212> TYPE: PRT
<213> ORGANISM: Unknown
<220> FEATURE:
<223> OTHER INFORMATION: Description of Unknown: HIV Vpr protein nuclear localization signal sequence

<400> SEQUENCE: 15

Arg Arg Thr Arg Asn Gly Ala Ser Lys Ser
1 5 10

<210> SEQ ID NO 16
<211> LENGTH: 19

```
<212> TYPE: PRT
<213> ORGANISM: Unknown
<220> FEATURE:
<223> OTHER INFORMATION: Description of Unknown:
      hnRNP A1 nuclear localization signal sequence

<400> SEQUENCE: 16

Ser Ser Asn Phe Gly Pro Met Leu Gly Gly Asn Arg Phe Phe Arg Ser
1               5                   10                  15

Ser Pro Tyr


<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Ser Gly Gly Ser Gly Gly Ser Gly Gly Ser Gly Gly Ser
1               5                   10                  15


<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 “Glu Ala Ala
      Ala Lys” repeating units

<400> SEQUENCE: 18

Glu Ala Ala Ala Lys Glu Ala Ala Ala Lys Glu Ala Ala Ala Lys Glu
1               5                   10                  15

Ala Ala Ala Lys
            20


<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 “Gly Gly Gly
      Gly Ser” repeating units

<400> SEQUENCE: 19

Gly Gly Gly Gly Ser Gly Gly Gly Gly Ser Gly Gly Gly Gly Ser Gly
1               5                   10                  15

Gly Gly Gly Ser
            20
```